United States Patent
Iyer et al.

(10) Patent No.: US 11,760,823 B2
(45) Date of Patent: Sep. 19, 2023

(54) BIOCOMPATIBLE DENDRONISED POLYMER AS A NON-VIRAL TRANSFECTION AGENT

(71) Applicant: The University of Western Australia, Crawley (AU)

(72) Inventors: Killugudi Swaminatha Iyer, Edgewater (AU); Marck Norret, Hovea (AU); Jessica Kretzmann, Bull Creek (AU); Diwei Ho, Northbridge (AU)

(73) Assignee: The University of Western Australia, Crawley (AU)

( * ) Notice: Subject to any disclaimer, the term of this patent is extended or adjusted under 35 U.S.C. 154(b) by 1062 days.

(21) Appl. No.: 16/128,936

(22) Filed: Sep. 12, 2018

(65) Prior Publication Data

US 2019/0077897 A1   Mar. 14, 2019

(30) Foreign Application Priority Data

Sep. 13, 2017  (AU) ................................ 2017903723

(51) Int. Cl.
| | | |
|---|---|---|
| *A61K 48/00* | (2006.01) | |
| *A61P 35/00* | (2006.01) | |
| *C08F 220/20* | (2006.01) | |
| *C08F 220/56* | (2006.01) | |
| *C08F 220/06* | (2006.01) | |

(52) U.S. Cl.
CPC .......... *C08F 220/20* (2013.01); *A61K 48/005* (2013.01); *A61K 48/0041* (2013.01); *A61P 35/00* (2018.01); *C08F 220/06* (2013.01); *C08F 220/56* (2013.01)

(58) Field of Classification Search
CPC .... C08F 220/56; C08F 220/06; C08F 220/20; A61P 35/00; A61K 48/0041; A61K 48/005
See application file for complete search history.

(56) References Cited

U.S. PATENT DOCUMENTS

| | | | |
|---|---|---|---|
| 2002/0098176 A1* | 7/2002 | Hembrough et al. | |
| 2009/0001802 A1* | 1/2009 | Daillo | |
| 2013/0022538 A1* | 1/2013 | Rossi | A61P 35/00 424/1.11 |

OTHER PUBLICATIONS

Kretzmann et al. (Chem. Sci. 2017, 8, 2923-2930) (Year: 2017).*
Gao et al. (J. Am. Chem. Soc. 2007, 129, 6633-6639). (Year: 2007).*
Weaver et al. (Macromolecules: 2004, 37, 2395-2403). (Year: 2004).*
Lee et al. (Bioconjugate Chem. 2007, 18, 579-584). (Year: 2007).*
Wang et al. (Nature Communications, published online Jan. 10, 2014, p. 1-8). (Year: 2014).*
Nelson et al. (Annu. Rev. Chem. Biomol. Eng. 2016, 7:637-62, published online on Apr. 21, 2016). (Year: 2016).*
Zhao et al. (Polymer, 53 (2012): 1992-2000). (Year: 2012).*
Kretzmann et al., "Synthetically controlling dendrimer flexibility improves delivery of large plasmid DNA," Chemical Science, 8:2923-2930 (2017).
Presentation made at the 36th Australian Polymer Symposium in Nov. 2016.
Presentation made at the Emerging Polymer Technologies Summit on Sep. 14, 2016.

* cited by examiner

*Primary Examiner* — Alma Pipic
(74) *Attorney, Agent, or Firm* — Foley Hoag LLP; Alexander Akhiezer; Laura A. Wzorek

(57) ABSTRACT

The invention relates in general to hydrophilic, biocompatible dendronised polymers, to complexes comprising the dendronised polymers, to methods of preparing the dendronised polymer and to uses of the dendronised polymer as a non-viral transfection agent for the delivery of biomolecules, in particular, genome editing tools, into a cell.

19 Claims, 15 Drawing Sheets a b

BIOCOMPATIBLE DENDRONISED POLYMER AS A NON-VIRAL TRANSFECTION AGENT

RELATED APPLICATION

This Application claims priority to Australian Patent Application No. 2017903723, filed on Sep. 13, 2017, which is hereby incorporated by reference in its entirety.

TECHNICAL FIELD

The present invention relates in general to biocompatible dendronised polymers, to complexes comprising the dendronised polymers, to methods of preparing the dendronised polymer and to uses of the dendronised polymer as a non-viral transfection agent for delivering a biomolecule into a cell.

BACKGROUND

Emerging genome and epigenome editing technologies have the potential to correct mutations associated with disease, introduce genes for therapy, and remove deleterious genes or sequences, but achieving efficient and reliable delivery of these tools remains a challenge.

Modulation of gene expression can be achieved using three major classes of genomic editing tools: zinc finger proteins (ZFs), transcription activator-like effectors (TALEs), and clustered regularly interspaced short palindromic repeat (CRISPR) proteins together with CRISPR-associated (Cas) proteins (CRISPR/Cas). The successful implementation of gene therapies will depend upon high specificity for the target gene. Zinc finger proteins can be easily packaged and delivered due to their small size, but have demonstrated high off-target effects. TALEs can be programmed to almost any given DNA sequence with high specificity, but large plasmid size hinders successful delivery. The current state-of-the-art CRISPR/Cas9 system has potential for altering gene expression with high targeting density, ease of engineering for multiple targets, and minimal off-target effects.

Success in gene therapy is currently largely reliant on the development of an effective delivery system that is capable of delivering genomic editing tools. Gene delivery agents (vectors) can be broadly categorised as viral or non-viral.

Liposomal and viral vectors have been used for the concurrent delivery of multiple components (for example, CRISPR and Cas9 plasmid, together with multiple guide RNAs) for effective or CRISPR-based genome editing. However, delivery systems based on lentiviral and adeno-associated viral vectors are limited by their intrinsic packaging capacity, whereas liposomes are limited by variability in forming DNA/liposome complexes, high toxicity, poor stability, and rapid clearance. Attempts to overcome these problems have involved the use of higher-capacity adenoviruses, smaller CRISPR constructs and hydrodynamic injection-based delivery strategies, albeit with lower editing efficiencies, restricted range of accessible targets and associated immunogenicity.

Non-viral vectors based on synthetic cationic polymers such as poly(ethylene imine) (PEI) have been investigated for gene delivery due to their ability to condense plasmid DNA (pDNA) and protect it from cellular and restriction nucleases. However, transfection efficiency for a number of cationic polymers is poor for large plasmids, and correlates with substantial cytotoxicity. Attempts to minimise toxicity while maximising transfection efficiency have involved comparisons of linear and randomly branched architectures to vary charge density with molecular weight, with little success.

Dendrimers are synthetic macromolecules of precisely regulated size and structure that are characterised by a highly branched architecture surrounding a central core. Poly(amido amine) (PAMAM) dendrimers are commercially available dendrimer-based non-viral vectors. PAMAM dendrimers can act as efficient delivery agents due to a high density of primary amines on their periphery, which can interact with anionic DNA molecules to form stable polyplexes, and a high density of tertiary amines in their interior, which provide sufficient buffering capacity to enable endosomal escape of delivered DNA. However, as dendrimer generation increases the macromolecules become conformationally restricted and are associated with significant intermolecular interactions, lowering their flexibility and their ability to form stable polyplexes with pDNA. Additionally, higher generation dendrimers are associated with significant cytotoxicity. These generation-dependent steric properties and toxicity impair the ability of dendrimers to deliver large genome editing DNA constructs.

There remains a need to provide a macromolecule that addresses or at least ameliorates one or more of the disadvantages discussed above. In particular, there remains a need to provide a macromolecule that is able to function as an effective carrier for the intracellular delivery of biomolecules, such as genome editing tools.

There also remains a need to provide a controlled synthetic strategy for preparing engineered macromolecular non-viral vectors that ameliorate or overcome the aforementioned biomolecule delivery challenges.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

SUMMARY OF THE INVENTION

The present invention provides for biocompatible dendronised polymers that can be used as a carrier for the intracellular delivery of biomolecules such as nucleic acids. The dendronised polymer disclosed herein combines the multi-valency of dendrimers with the conformational flexibility of linear polymers for optimal biomolecule binding.

In a broad aspect, the present invention provides a hydrophilic, biocompatible dendronised polymer comprising:
 a linear aliphatic copolymer backbone; and
 a plurality of dendrons pendant from and coupled to the copolymer backbone.

In one aspect, the present invention provides a hydrophilic, biocompatible dendronised polymer comprising:
 a linear aliphatic copolymer backbone; and
 a plurality of dendrons pendant from the copolymer backbone and coupled to the copolymer backbone via a reaction product of a click coupling reaction.

In one set of embodiments, each dendron is coupled to the copolymer backbone via a triazole moiety, which is a reaction product of an azide/alkyne cycloaddition.

The linear aliphatic copolymer backbone is generally formed through the copolymerisation of at least two hydrophilic ethylenically unsaturated co-monomers. Thus, the copolymer backbone comprises polymerised residues derived from at least two such co-monomers.

The linear aliphatic copolymer backbone may comprise polymerised residues derived from a range of suitable hydrophilic ethylenically unsaturated monomers. In particular embodiments, the copolymer backbone comprises polymerised residues derived from glycidyl methacrylate (GMA) and 2-hydroxyethyl acrylate (HEMA).

The plurality of dendrons may each be polyamino dendrons, in particular, poly(amido amine) (PAMAM) dendrons. The PAMAM dendrons may each be G2 to G5 PAMAM dendrons. In some embodiments, each PAMAM dendron is a G4 to G5 dendron.

In some embodiments, dendronised polymers described herein have a dendron density in a range of from about 3 to 30%, preferably approximately 17%.

In one set of embodiments, the dendronised polymer comprises:
  a linear aliphatic copolymer backbone; and
  a plurality of PAMAM dendrons pendant from the copolymer backbone and coupled to the copolymer backbone via a triazole moiety.

Dendronised polymers described herein may comprise dendrons comprising terminal fluoro groups. Such fluorinated dendrons may assist in enhancing the transfection capability of the dendronised polymer. Exemplary fluoro groups include fluoroalkyl groups, such as heptafluoropropyl groups.

The present invention also provides for methods for preparing hydrophilic, biocompatible dendronised polymers. The methods described herein enable the synthesis of dendronised polymers of controlled and versatile structures that can be tuned to allow for optimised biomolecule delivery.

In another aspect, the present invention provides a method of preparing a hydrophilic, biocompatible dendronised polymer comprising the steps of:
  providing a linear aliphatic copolymer backbone comprising a plurality of pendant functional groups;
  providing a plurality of dendrons, each dendron comprising a functional group at its focal point that is capable of reacting with a pendant functional group; and
  reacting the pendant functional groups on the copolymer backbone with the functional groups at the focal point of the dendrons to thereby couple each dendron to the copolymer backbone.

In one set of embodiments, hydrophilic, biocompatible dendronised polymers of the invention are prepared using methods involving click chemistry.

Thus in another aspect, the present invention provides a method of preparing a hydrophilic, biocompatible dendronised polymer comprising the steps of:
  providing a linear aliphatic copolymer backbone comprising a plurality of pendant functional groups capable of participating in a click coupling reaction;
  providing a plurality of dendrons, each dendron comprising a functional group at its focal point that is capable of reacting with a pendant functional group via a click coupling reaction; and
  reacting the pendant functional groups on the copolymer backbone with the functional groups at the focal point of the dendrons under click chemistry conditions to form a click reaction product that couples each dendron to the copolymer backbone.

In some embodiments of the above method, the click reaction product is a triazole moiety that is formed from an azide-alkyne cycloaddition under click chemistry conditions.

To enable a triazole moiety to be formed, the pendant functional groups on the copolymer backbone may be selected from the group consisting of an azide and alkyne functional group, while the functional group at the focal point of each dendron is the other selected from the group consisting of an azide and alkyne functional group. In particular embodiments, the linear copolymer backbone comprises a plurality of pendant azide functional groups, and each dendron comprises an alkyne functional group at its focal point.

In another aspect, the present invention provides a method of preparing a hydrophilic, biocompatible dendronised polymer comprising the steps of:
  (i) providing a linear aliphatic copolymer backbone comprising a plurality of pendant functional groups;
  (ii) coupling a pendant functional group with a plurality of functional compounds to generate a branch forming part of a dendron and a plurality of functional groups;
  (iii) coupling the plurality of functional groups with a polyfunctional compound to extend the branch and generate a plurality of further functional groups;
  (iv) coupling each further functional group formed in step (iii) with a plurality of functional compounds to thereby generate a further branch in the dendron and a plurality of functional groups;
  (v) optionally, repeating at least one of steps (iii) and (iv) at least once.

In yet another aspect the present invention provides a method of preparing a hydrophilic, biocompatible dendronised polymer comprising the steps of:
  (i) providing a linear aliphatic copolymer backbone comprising a plurality of pendant functional groups;
  (ii) coupling a pendant functional group with a polyfunctional compound to generate a branch forming part of a dendron and a plurality of functional groups;
  (iii) coupling the plurality of functional groups with a further polyfunctional compound to thereby generate a further branch in the dendron and a further plurality of functional groups; and
  (iv) optionally, repeating step (iii) at least once.

In some embodiments of the method of one or more aspects of the invention, the linear aliphatic copolymer backbone is provided by polymerising a monomer composition comprising at least two hydrophilic ethylenically unsaturated co-monomers under a controlled free radical polymerisation process, wherein at least one of the co-monomers comprises a functional group that is (i) able to provide a pendant functional group capable participating in a click coupling reaction, or (ii) able to be modified to provide a pendant functional group capable of participating in a click coupling reaction, and if (ii), then the method further comprises the step of modifying the functional group to provide a pendant functional group capable of participating in a click coupling reaction.

In particular embodiments of the method, the controlled free radical polymerisation process used for forming the linear aliphatic copolymer backbone is selected from the group consisting of atom transfer radical polymerisation (ATRP) and reversible addition-fragmentation transfer (RAFT) polymerisation.

In some embodiments, the method of the invention may further comprise the step of reacting at least one terminal functional group on each dendron with a fluorination agent to thereby from dendrons with at least one terminal fluoro group.

Dendronised polymers of the present invention are suitably able to form complexes with biomolecules and thus may act as carriers for the intracellular delivery of the biomolecules.

In another aspect, the present invention provides a complex comprising a biomolecule and dendronised polymer of any one of the embodiments described herein.

In a further aspect, the present invention also provides a method of delivering a biomolecule into a cell comprising exposing the cell to a complex comprising the biomolecule and a dendronised polymer of any one of the embodiments described herein.

In yet another aspect, the present invention also provides a method for the treatment of cancer comprising administering a complex comprising a biomolecule and dendronised polymer of any one of the embodiments described herein to a subject in need thereof.

Complexes described herein may comprise a biomolecule selected from the group consisting of a nucleic acid molecule, a protein molecule, a therapeutically active agent, and combinations thereof.

In particular embodiments, the complex comprises a biomolecule selected from the group consisting of a zinc finger (ZF) protein, a transcription activator-like effector (TALE) or a CRISPR-mediated gene editing system.

BRIEF DESCRIPTION OF THE FIGURES

Embodiments of the invention will now be described with reference to the following non-limiting drawings in which.

DETAILED DESCRIPTION OF THE INVENTION

Figure 1:
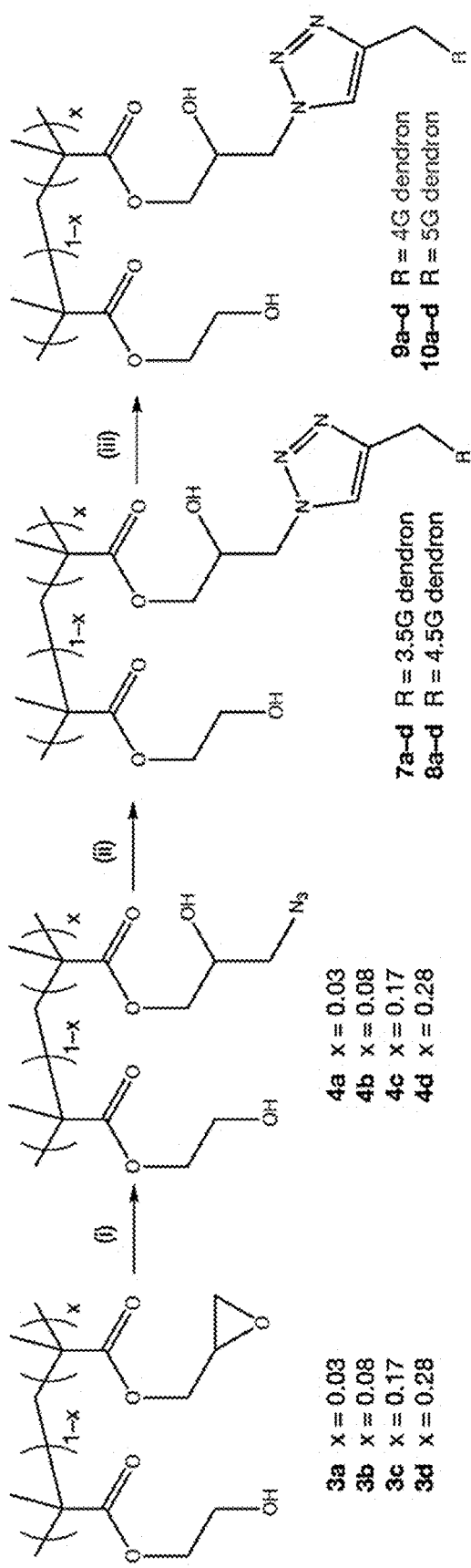
FIG. 1 is a scheme illustrating a synthetic protocol for the preparation of dendronised polymers of the invention under reaction conditions: (i) NaN$_3$, NH$_4$Cl, DMF, 60° C., 72 h; (ii) PMDETA, CuBr, DMF, r.t., 72 h; (iii) ethylene diamine, MeOH, 0° C., where copolymer backbones that are random statistical copolymers of HEMA and GMA where x=mol % GMA, and poly(amido amine) dendrons of different generation are clicked onto the linear polymer backbone. Reaction conditions: (i) NaN$_3$, NH$_4$Cl, DMF, 60° C., 72 h; (ii) PMDETA, CuBr, DMF, r.t., 72 h; (iii) ethylene diamine, MeOH, 0° C.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

Percentages (%) referred to herein are based on weight percent (w/w or w/v) unless otherwise indicated.

As used herein the terms "treating" and "treatment" refer to any and all uses which remedy a condition or symptom, or otherwise hinder, retard, suppress or reverse the progression of a condition or disease or other undesirable symptoms in any way whatsoever. Thus, the terms "treating" and "treatment" and the like are to be considered in their broadest context. For example, treatment does not necessarily imply that a patient is treated until total recovery. In the context of the present disclosure "treatment" may involve reducing or ameliorating the occurrence of a symptom or highly undesirable event associated with the disorder or an irreversible outcome of the progression of the disorder but may not of itself prevent the initial occurrence of the event or outcome. Accordingly, treatment includes the amelioration of one or more symptoms of a particular disorder or preventing or otherwise reducing the risk of developing a particular disorder.

The present invention relates to hydrophilic, biocompatible dendronised polymers that are useful as non-viral vectors for the intracellular delivery of biomolecules, such as proteins and nucleic acids employed as gene editing tools.

In a broad aspect, there is provided a hydrophilic, biocompatible dendronised polymer comprising:
 a linear aliphatic copolymer backbone; and
 a plurality of dendrons pendant from and coupled to the copolymer backbone.

The dendronised polymer of the present invention is biocompatible and hydrophilic and is amenable for use in biomedical applications.

By "biocompatible" is meant that the dendronised polymer is minimally toxic or non-toxic to a biological environment, such as a cell, living tissue or a living organism. The term "biocompatible" is also used herein to refer to dendronised polymers that are selectively biocompatible. By selectively biocompatible is meant that the dendronised polymer is minimally toxic or non-toxic to one cell type, tissue type or organism, but may be toxic to a different cell type, tissue type or organism.

By "hydrophilic" is meant that the dendronised polymer has an affinity for water and is thus compatible with an aqueous solvent and may be soluble in an aqueous solvent. Preferably, the dendronised polymer is soluble in water. In some embodiments, the dendronised polymer may have a solubility in water of at least 10 g of polymer per 100 g of water at 25° C.

The copolymer backbone of the dendronised polymer is a linear, aliphatic molecule. By "aliphatic" is meant that the copolymer backbone is a straight chain hydrocarbon moiety that may be branched or unbranched, and which comprises carbon atoms that are linked together via carbon-carbon bonds. The hydrocarbon moiety may be completely saturated or may contain one or more units of unsaturation, but which is not aromatic. In general, the chain of carbon atoms forming the backbone of the dendronised polymer is not interrupted by heteroatoms, such as oxygen, nitrogen or sulfur atoms. In one embodiment, the copolymer backbone is a saturated, straight-chain hydrocarbon moiety.

The copolymer backbone of the dendronised polymer is preferably formed through the polymerisation of at least two different ethylenically unsaturated co-monomers. The polymerisation of the co-monomers generally occurs under free radical polymerisation conditions and thus the linear copolymer backbone of the dendronised polymer is produced when the unsaturated moieties of the co-monomers are polymerised and linked together by covalent bonds. The copolymer backbone is therefore a synthetic molecule that contains polymerised residues derived from the co-monomers. A skilled person would understand that a polymerised residue is formed when a monomer is incorporated into the structure of the linear polymer chain. Polymerised residues may be regarded as monomeric units of the linear polymer. In some embodiments the copolymer may be formed through the polymerisation of three or more different co-monomers.

Ethylenically unsaturated co-monomers employed for formation of the linear aliphatic copolymer backbone can be hydrophilic. However, a person skilled in the art would appreciate that it is not essential for the linear copolymer backbone to be prepared from hydrophilic co-monomers. Rather, provided that the dendronised polymer per se is hydrophilic, then the requirements of the invention will be met.

In one set of embodiments, the linear copolymer backbone comprises polymerised residues of at least two different hydrophilic ethylenically unsaturated monomers. The hydrophilic monomers assist to confer hydrophilic properties to the dendronised polymer.

Ethylenically unsaturated moieties referred to herein may be carbon-carbon double bonds or carbon-carbon triple bonds. The ethylenically unsaturated moiety may be a part of a ring structure or a terminal group. A range of suitable ethylenically unsaturated hydrophilic monomers would be known to a skilled person.

In one set of embodiments, the linear copolymer backbone comprises polymerised residues derived from an ethylenically unsaturated monomer selected from the group consisting of 2-hydroxyethyl acrylate, 2-methoxyethyl acrylate, N-acryloylamido-ethoxyethanol, N,N-dimethylacrylamide, N,N-diethylacrylamide, N-(2-hydroxyethyl)acrylamide, N-(hydroxymethyl)acrylamide, acrylamide, N-isopropyl acrylamide, methacrylamide, 2-hydroxyethyl methacrylate, 2-(dimethylamino)ethyl acrylate, 3-(dimethylamino)propyl acrylate, acrylic acid, methacrylic acid, 2-(dimethylamino)ethyl methacrylate, glycidyl methacrylate, 2-azido-1-hydroxyethyl methacrylate, and combinations thereof.

In one set of embodiments, the linear aliphatic copolymer backbone is a statistical copolymer that comprises statistically distributed polymerised residues of at least two different ethylenically unsaturated monomers. In one preference, the co-monomers forming polymerised residues in the linear copolymer are hydrophilic monomers. The hydrophilic polymerised residues can assist to confer hydrophilic properties to the dendronised polymer.

A skilled person would understand that a "statistical copolymer" is a macromolecule in which the sequential distribution of the monomeric units obeys known statistical laws. An example of a statistical copolymer is a macromolecule in which the sequential distribution of monomeric units follows Markovian statistics. Co-monomers of selected reactivity ratios may chosen to ensure a statistical distribution of polymerised residues in the resultant copolymer. A statistical copolymer may also be known as a "random copolymer".

In some embodiments, the linear copolymer backbone comprises polymerised residues derived from at least two ethylenically unsaturated co-monomers, wherein at least one of the co-monomers comprises a functional group that is:
(i) able to provide a pendant functional group capable participating in a coupling reaction, or
(ii) able to be modified to provide a pendant functional group capable of participating in a coupling reaction.

In some particular embodiments, the coupling reaction is a covalent coupling reaction. An exemplary coupling reaction may be a click coupling reaction.

Thus in some particular embodiments, the linear copolymer backbone comprises polymerised residues derived from at least two ethylenically unsaturated co-monomers, wherein at least one of the co-monomers comprises a functional group that is:
(i) able to provide a pendant functional group capable participating in a click coupling reaction, or
(ii) able to be modified to provide a pendant functional group capable of participating in a click coupling reaction.

In one set of embodiments, the copolymer backbone comprises polymerised residues of a co-monomer comprising a functional group that is able to be modified to provide a functional group capable of participating in a click coupling reaction. An example of a modifiable functional group is an epoxy functional group. Epoxy functional groups that are pendant from the copolymer backbone may conveniently be modified to facilitate the introduction of a pendant functional group that is capable of participating in a click coupling reaction.

In one set of embodiments, the copolymer backbone comprises polymerised residues derived from glycidyl methacrylate and at least one other ethylenically unsaturated monomer.

As an example, the epoxy moiety of glycidyl methacrylate may be readily modified by reaction with an appropriate reagent to provide a functional group that is capable of participating in a click coupling reaction. For example, a linear copolymer comprising polymerised residues derived from glycidyl methacrylate will have pendant epoxy functional groups that may be ring opened by sodium azide ($NaN_3$) via a nucleophilic substitution reaction under appropriate conditions. The ring opening reaction will then result in the introduction of a pendant azido functional group from the linear copolymer. In this manner, suitable pendant functional groups capable of participating in a click coupling reaction may be distributed at intervals along the linear copolymer chain.

In one embodiment, the copolymer backbone comprises polymerised residues of:
(a) a first monomer which is glycidyl methacrylate; and
(b) a second monomer which is selected from the group consisting of 2-hydroxyethyl acrylate, 2-methoxyethyl acrylate, N-acryloylamido-ethoxyethanol, N,N-dimethylacrylamide, N,N-diethylacrylamide, N-(2-hydroxyethyl)acrylamide, N-(hydroxymethyl)acrylamide, acrylamide, N-isopropyl acrylamide, methacrylamide, 2-hydroxyethyl methacrylate, 2-(dimethylamino)ethyl acrylate, 3-(dimethylamino)propyl acrylate, acrylic acid, methacrylic acid, 2-(dimethylamino)ethyl methacrylate, and 2-azido-1-hydroxyethyl methacrylate.

In one preference, the second monomer is 2-hydroxyethyl methacrylate (HEMA). In such embodiments, the copolymer backbone comprises polymerised residues derived from glycidyl methacrylate and 2-hydroxyethyl methacrylate.

The copolymer backbone may comprise polymerised residues derived from the first and second monomers in a suitable molar ratio. The molar ratio may influence the dendron density in the dendronised polymer. The "dendron density" reflects the number or quantity of dendrons coupled to the linear copolymer backbone.

In one embodiment, the molar ratio between the first and second co-monomers in the copolymer backbone may be in the range of from 3:97 to 30:70.

Thus in some embodiments, polymerised residues derived from glycidyl methacrylate may constitute from 3 to 30 mol % of the linear aliphatic copolymer backbone, with the remaining 97 to 70 mol % of polymerised residues being derived from the second co-monomer.

In some embodiments, the molar ratio between the first and second co-monomers in the copolymer backbone may be in a range of from about 5:95 to 25:75, or in a range of from about 10:90 to 20:80. In an exemplary embodiment, the molar ratio between the first and second co-monomers is approximately 17:83. In another exemplary embodiment, the molar ratio between the first and second co-monomers is approximately 25:75.

The linear aliphatic copolymer backbone may be of any suitable size or molecular weight. Suitably, the copolymer backbone is of a size that allows for the coupling a plurality of dendrons while retaining a degree of flexibility as this can aid in the binding of a biomolecule to the dendronised polymer. Preferably, the linear copolymer backbone is about 5 kDa or larger. The copolymer backbone may have a molecular weight of no more than about 40 kDa. In one preference, the linear copolymer backbone has a molecular weight in a range of from about 15 to 25 kDa.

Linear, aliphatic copolymer backbones described herein may be prepared in any suitable manner. A suitable synthetic method used to produce the copolymer backbones provided herein is free radical polymerisation.

In one set of embodiments, the copolymer backbone is formed using a controlled free radical polymerisation process. A number of controlled free radical polymerisation processes may be utilised. Exemplary controlled radical free radical polymerisation processes that may be used include atom transfer radical polymerisation (ATRP) and reversible addition-fragmentation transfer (RAFT) polymerisation.

Biocompatible dendronised polymers of the invention also comprise a plurality of dendrons that are pendant from the copolymer backbone. Furthermore, each of the plurality of dendrons is coupled to the copolymer backbone.

A "dendron" is a wedge-shaped and highly branched molecule that is characterised by a tree-like molecular architecture emanating from a focal point. Dendrons have interior layers (also called "generations") that consist of repeating units, and may further have an exterior surface of terminal functional groups attached to the outermost generation.

Dendron generation number (usually abbreviated to G #) is determined by the number of interior layers going from the focal point towards the surface or periphery of the dendron. The molecular weight of the dendron and the number of terminal functional groups can be determined by the generation.

Dendrons of various structure and composition may be prepared using a number of different synthetic schemes. Methods for preparing dendrons, including convergent and divergent methods, would be known by a skilled person.

The dendronised polymer of the present invention comprises a plurality of hydrophilic dendrons, which help to impart hydrophilicity to the resultant dendronised polymer.

In one embodiment, each dendron is a poly(amino) dendron. Such dendrons are generally hydrophilic and comprise a plurality of amino groups. The amino may be primary, secondary or tertiary amino, or a combination of such amino groups. The amino groups may be situated at the surface of the dendrons and/or in one or more internal layers of the dendrons.

Some specific examples of dendrons that may be coupled to the linear copolymer backbone include poly(amido amine) (PAMAM), poly(propylene imine) (PPI) and poly (lysine) dendrons. Derivatives based on these dendrons, i.e. with a variety of different amine containing functionalisations or surface groups, can also be used.

In a particular embodiment, the dendronised polymer comprises a plurality of PAMAM dendrons.

PAMAM dendrons useful for the present invention can be prepared by a synthetic protocol that involves first reacting an amino compound having at least one primary amine group (e.g. propargylamine) with methyl acrylate under conditions sufficient to cause the Michael addition of one molecule of the amino compound to molecules of the methyl acrylate to form an initial adduct. Following removal of unreacted methyl acrylate, this initial adduct is reacted with excess ethylenediamine under conditions such that one amine group of the ethylenediamine molecule reacts with the methyl carboxylate groups of the adduct to form a first generation (G1) adduct having multiple (e.g. two) amidoamine moieties. Following removal of unreacted ethylenediamine, this first generation adduct is then reacted with excess methyl acrylate under Michael addition conditions to form a second generation adduct having terminal methyl ester moieties. The second generation adduct is then reacted with excess ethylenediamine under amide forming conditions to produce a second generation (G2) poly(amidoamine) dendron having ordered branches with terminal amino moieties. Repeated and sequential reactions of the terminal amino moieties with methyl acrylate and ethylenediamine can then produce subsequent generations in the PAMAM dendron.

Dendronised polymers of the present invention may suitably comprise PAMAM dendrons as PAMAM dendrons fulfil the requirements of low cytotoxicity, controlled and quantifiable synthesis, and a known ratio of primary to tertiary amines.

The PAMAM dendrons further comprise a plurality of terminal primary amino functional groups that may participate in binding interactions with one or more biomolecules. For example, the primary amino groups may be cationic at physiological pH (pH approximately 7) and may interact electrostatically with anionic biomolecules such as DNA.

Alternatively, as discussed further below, the terminal amino functional groups on PAMAM dendrons may be modified to provide terminal functionalities, such as terminal fluoro groups, fluorescent groups, stealth groups or targeting ligands, at the periphery of the dendrons.

PAMAM dendrons utilised in the dendronised polymers may comprise at least 2 generations, and thus may be G2 or higher generation PAMAM dendons. In some embodiments, PAMAM dendrons may each be G2 to G5 or higher generation (i.e. >G5) PAMAM dendrons, including half generation dendrons. In some embodiments, the PAMAM dendrons may each be G3-G6, or G4-G5 dendrons, including half generation dendrons.

While PAMAM dendrons are described herein, it is contemplated that the dendronised polymer may comprise other types of dendrons of different size and/or composition. The selection of a dendron of a particular size and/or composition may be dependent on type of biomolecule desired to be delivered by the dendronised polymer.

Further, it will be appreciated that when dendrons of different size (i.e. generation number) are coupled to the linear copolymer backbone, the copolymer size (i.e. its molecular weight) may be adjusted to make accommodation for the dendron size. For example, a higher molecular weight copolymer backbone may be desired when higher generation dendrons (e.g. G4 and above) are employed.

Similarly, where a larger number of dendrons (i.e. high dendron density) are coupled to the linear copolymer backbone, a higher molecular weight copolymer backbone may be utilised to accommodate the quantity of dendrons.

A skilled person would appreciate that changing the density of dendrons along the copolymer backbone and/or changing dendron generation can alter the flexibility of the dendronised polymer can thus have an influence on transfection capability. For example, in some instances, high dendron density and/or high dendron generation can limit flexibility due to steric bulk imposed on the dendronised polymer by the dendrons.

Figure 15:
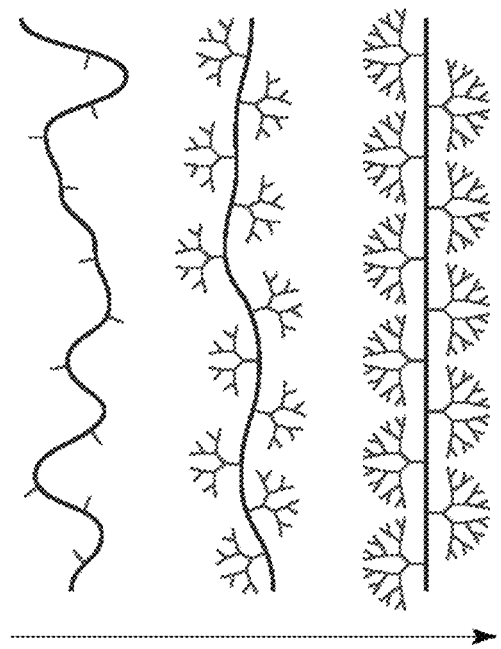
FIG. 15 is a scheme illustrating how the flexibility of a dendronised polymer in accordance with the present invention can be altered by independently varying dendron generation and dendron density.
Figure 15:
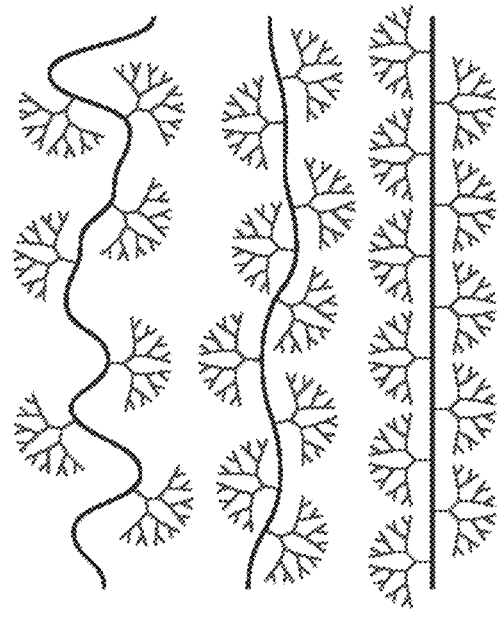

A schematic illustrating how the flexibility of the dendronised polymer can be altered by independently varying dendron generation and dendron density is shown in FIG. 15.

Each of the plurality of dendrons is coupled to the linear aliphatic copolymer backbone. The dendrons may be coupled to the copolymer backbone by a number of different ways, including via covalent coupling or oxidative coupling.

In some embodiments, each dendron is coupled to the copolymer backbone via a covalent reaction product generated from a covalent coupling reaction. Covalent reaction products may be functional groups formed after covalent reaction of complementary functional groups that are present in the linear aliphatic copolymer backbone and at the focal point of each dendron. Some non-limiting examples of covalent reaction products include esters (which can be formed from the reaction of acids and alcohols), amides (which can be formed from the reaction of acids and amines), urethanes (which can be formed from the reaction of isocyanates and amines), and ethers (which can be formed from the reaction of two alcohols).

In some embodiments, each dendron is coupled to the copolymer backbone via an oxidative coupling reaction product generated from an oxidative coupling reaction. An example of an oxidative coupling reaction product is a disulfide, which is formed from the reaction of two sulfhydryl (—SH) groups in the presence of an oxidant.

In some particular embodiments, each of the plurality of dendrons is coupled to the linear aliphatic copolymer backbone via a reaction product generated from a click coupling reaction.

Thus in one aspect, the present invention provides a hydrophilic, biocompatible dendronised polymer comprising:
a linear aliphatic copolymer backbone; and
a plurality of dendrons pendant from the copolymer backbone and coupled to the copolymer backbone via a reaction product of a click coupling reaction.

Click coupling reactions are performed under click chemistry conditions. The term 'click chemistry' was coined by Professor K. Barry Sharpless in 2001 to describe a series of chemical reactions defined by their modular nature, high yield, stability of products in vivo, stereospecificity, high atom economy and high thermodynamic driving force. A number of 'click' reactions exist, which can be classified into four main groups: (1) cycloadditions including 1,3-dipolar cycloadditions and hetero-Diels-Alder cycloadditions, (2) nucleophilic ring openings of strained heterocyclic electrophiles, (3) carbonyl chemistry of the non-aldol type, and (4) additions to carbon-carbon multiple bonds.

In one set of embodiments, dendronised polymers of the invention comprise a plurality of dendrons, with each dendron being coupled to the copolymer backbone via a product of a cycloaddition reaction performed under click conditions. The cycloaddition product generated from the click reaction is generally a stable cyclic structure.

Using click chemistry, functional groups that are pendant from the linear copolymer backbone may react with a complementary functional group that is located at the focal point of a dendron to generate a click reaction product.

The use of click chemistry for coupling of the dendrons to the copolymer backbone is advantageous as it allows for simple, controlled attachment of complete dendrons onto the copolymer backbone, thereby enabling the synthesis of a library of well-defined dendronised polymers.

In one set of embodiments, the click reaction product is a triazole moiety that is formed from an azide-alkyne cycloaddition under click chemistry conditions. To enable a triazole moiety to be formed, the pendant functional groups on the copolymer backbone may be selected from the group consisting of an azide and alkyne functional group, while the functional group at the focal point of each dendron is the other selected from the group consisting of an azide and alkyne functional group. The covalent coupling of the complementary azide and alkyne functional groups produces a triazole moiety.

The resulting dendronised polymer therefore comprises a plurality of triazole moieties that couple the plurality of dendrons to the copolymer backbone.

A skilled person would recognise that the triazole moieties are also pendant from the copolymer backbone.

In a particular embodiment, dendronised polymers of the invention comprise a plurality of dendrons that are each coupled to the copolymer backbone via a 1,2,3-triazole moiety.

An appropriate click reaction for the formation of 1,2,3-triazoles is the Huisgen 1,3-dipolar cycloaddition of azides and alkynes (thermal) which gives a mixture of the 1,4 and 1,5 regioisomers of the 1,2,3-triazole. Click reactions suitable for forming trizaole moieties may also metal catalysed. For example, a Copper(I)-catalyzed Azide-Alkyne Cycloaddition (CuAAC) variant of the Huisgen cycloaddition of azides and terminal alkynes forms 1,2,3-triazoles. Use of a copper catalyst in the Huisgen cycloaddition reaction results in formation of a 1,4-substituted 1,2,3-triazole from azides and terminal alkynes, while use of a ruthenium catalyst enables use of terminal or internal alkynes and results in the formation of the alternate 1,5-regiosiomer. The use of a silver catalyst also results in the 1,4-substituted 1,2,3-triazole. Other metals that can be used include, but are not limited to, Ni, Pt, Pd, Rh, and Ir; the regiochemistry of the 1,2,3-triazole resulting from the use of these metal catalysts is less well defined.

In one set of embodiments, the dendronised polymer comprises:
a linear aliphatic copolymer backbone; and
a plurality of PAMAM dendrons pendant from the copolymer backbone and coupled to the copolymer backbone via a triazole moiety.

In one example of the above embodiment, the PAMAM dendrons are each G4-G5 dendrons.

Further, in one example of the above embodiment, the dendronised polymer may have a copolymer backbone of molecular weight in the range of from about 15 to 25 kDa and a dendron density selected from the group consisting of from about 3 to 30%, 5 to 25%, 10 to 20%, and about 17%.

As discussed above, PAMAM dendrons are amine rich molecules that can comprise a plurality of terminal amino functional groups. The terminal amino functional groups may become protonated, giving a dendron a polycationic charge that can subsequently interact with a biomolecule.

However, the terminal amino functional groups are also reactive and can participate in nucleophilic substitution reactions with other molecules. This in turn, can enable the surface functionality and properties of the dendrons to be modified.

In some embodiments, dendrons present in the dendronised polymer of the invention may comprise terminal functionalities extending from an outermost generation of the dendrons.

The terminal functionalities may be selected from the group consisting of fluoro groups, fluorescent groups, stealth groups or targeting ligands, and combinations thereof.

In one form of the invention, each dendron of the dendronised polymers of embodiments described herein may comprise at least one terminal fluoro group. In some embodiments, each dendron of the dendronised polymer comprises a plurality of terminal fluoro groups. The presence of terminal fluoro groups may enhance the transfection efficiency of the dendronised polymer.

However, it is not essential for all terminal functional groups on the dendrons to be terminal fluoro groups. Rather, partial fluorination of the dendrons may be sufficient to confer enhanced transfection capabilities.

Fluorination enhances cellular uptake of polyplexes, facilitates their endosomal escape and provides excellent serum resistance. When dendronised polymers of the invention are fluorinated, it is preferred that the extent of fluorination is at a level that is not sufficient to induce unwanted cytotoxicity.

In one set of embodiments, the dendronised polymer comprises a plurality of PAMAM dendrons coupled to the linear copolymer backbone and said dendrons comprise from about 20 to 60 mol %, preferably about 40 mol %, terminal fluoro groups.

The terminal fluoro groups may be fluoroalkyl groups, and may be perfluoroalkyl groups.

Fluoroalkyl groups may comprise from 1 to 12 carbon atoms, from 2 to 8 carbon atoms, or from 3 to 6 carbon atoms.

Perfluoroalkyl groups may comprise from 1 to 12 carbon atoms, from 2 to 8 carbon atoms, or from 3 to 6 carbon atoms.

In one set of embodiments, the terminal fluoro groups are heptafluoropropyl groups.

The terminal fluoro groups may be introduced by reacting terminal functional groups present on the outermost generation of a dendron with an appropriate fluorination agent. For example, when the dendrons are PAMAM dendrons, terminal amino functional groups on the dendrons may react with a selected fluorination agent, such as heptafluorobutyric anhydride or glycidyl 2,2,3,3,4,4,5,5-octafluoropentyl ether, to introduce at least one, and preferably more than one, terminal fluoro group to the dendron and thus provide a fluorinated dendron.

In some embodiments, each dendron of the dendronised polymers of embodiments described herein may comprise a fluorescent group, a stealth group or a targeting ligand.

A fluorescent group may be a compound that fluoresces when exposed to particular wavelengths of light. A fluorescent group may therefore facilitate the imaging of cells and tissues in vitro or in vivo. A fluorescent group may operate in the visible, near infrared or ultraviolet parts of the electromagnetic spectrum. In one embodiment, the fluorescent group operates in the near infrared spectrum (wavelengths approximately 700-900 nm). An example of a fluorescent group is Cyanine-7 (Cy7) fluorescent dye.

A stealth group may be one that assists to shield charges (such as positive or negative charges) that may be present when the dendronised polymer is used in a complex with a biomolecule. Thus when attached to a dendron of the dendronised polymer, the group can confer stealth properties to the complexes, thereby allowing for longer circulation times in vivo and minimising non-specific cellular uptake of the complex. An example of a stealth group is poly(ethylene glycol) (PEG).

A targeting ligand may be one that increases the interaction or binding of a complex comprising the dendronised polymer to a target cell, thereby leading to a reduction in non-specific interactions and off-target effects. The targeting ligand may be selected from antibodies, aptamers, cholesterol and its derivatives, folate compounds or folate conjugates, transferrin, saccharides and cell-penetrating peptides. An example of a targeting ligand is cyclic RGD peptide.

In another aspect, the present invention provides a method of preparing a hydrophilic, biocompatible dendronised polymer comprising the steps of:
providing a linear aliphatic copolymer backbone comprising a plurality of pendant functional groups;
providing a plurality of dendrons, each dendron comprising a functional group at its focal point that is capable of reacting with a pendant functional group; and
reacting the pendant functional groups on the copolymer backbone with the functional groups at the focal point of the dendrons to thereby couple each dendron to the copolymer backbone.

The pendant functional group present on the linear aliphatic copolymer backbone may be selected from a wide variety of different types of functional groups. Examples of functional groups include, but are not limited to, acid functional groups (such as carboxylic acid), amino functional groups (such as primary, secondary or tertiary amino), amido functional groups, sulfhydryl functional groups, nitrile functional groups, epoxy functional groups, azido functional groups and alkynyl functional groups.

In some embodiments, the selection of a particular type of pendant functional group may, in part, be dependent on whether the pendant functional group is intended to be coupled to a pre-formed dendron to enable formation of a dendronised polymer via a convergent synthetic pathway, or whether the pendant functionality is intended to be reacted with a functional molecule to allow growth of a dendron from the copolymer backbone, thereby forming a dendronised polymer via a divergent synthetic pathway.

In one embodiment, each pendant functional group is selected to react with a functional group that is present at the focal point of a pre-formed dendron, thereby allowing the dendron to be coupled to the copolymer backbone. The pendant functional groups should be complementary to the functional group at the focal point of the dendron, such that the functional groups may react with one another under appropriate conditions, to result in coupling of the dendrons to the linear copolymer.

In one set of embodiments, reaction of the pendant functional groups on the copolymer backbone with the functional groups at the focal point of the dendrons proceeds under covalent reaction conditions and thereby forms a covalent reaction product. The covalent reaction product couples each of the dendrons to the copolymer backbone. Non-limiting covalent reaction products include amines (including secondary and tertiary amines), amides, esters, urethanes, and ethers, which are described herein above.

In another set of embodiments, reaction of the pendant functional groups on the copolymer backbone with the functional groups at the focal point of the dendrons proceeds under oxidative coupling conditions and thereby forms an oxidative coupling reaction product that couples each of the dendrons to the copolymer backbone. An example of an oxidative coupling reaction product is a disulfide.

In another set of embodiments, the reaction of the pendant functional groups on the copolymer backbone with the functional groups at the focal point of the dendrons is performed under click chemistry conditions. Such reactions form a click reaction product that couples each of the dendrons to the copolymer backbone.

In another aspect, the present invention provides a method of preparing a biocompatible, hydrophilic dendronised polymer comprising the steps of:
    providing a linear aliphatic copolymer backbone comprising a plurality of pendant functional groups capable of participating in a click coupling reaction;
    providing a plurality of dendrons, each dendron comprising a functional group at its focal point that is capable of reacting with a pendant functional group on the copolymer backbone via a click coupling reaction; and
    reacting the pendant functional groups on the copolymer backbone with the functional groups at the focal point of the dendrons under click chemistry conditions to form click reaction product that couples the dendrons to the copolymer backbone.

In some embodiments of the above method, the click reaction product is a triazole moiety that is formed from an azide-alkyne cycloaddition under click chemistry conditions.

To enable a triazole moiety to be formed, the pendant functional groups on the copolymer backbone may be selected from the group consisting of an azide and alkyne functional group, while the functional group at the focal point of each pre-formed dendron is the other selected from the group consisting of an azide and alkyne functional group.

Methods for synthesising dendronised polymers of the invention, which involve the coupling of a pre-formed copolymer backbone with pre-formed dendrons via an appropriate coupling moiety may be regarded as convergent methods of synthesis.

In particular embodiments, the linear copolymer backbone comprises a plurality of pendant azide functional groups, and each dendron comprises an alkyne functional group at its focal point.

However, a skilled person would appreciate that the order of the functional groups may be reversed. That is, the copolymer backbone may comprise a plurality of pendant alkyne functional groups and each dendron may comprise an azide functional group at its focal point.

In one embodiment, the linear aliphatic copolymer backbone may comprise from 3 to 30% pendant azide functional groups, preferably from 5 to 25% pendant azide functional groups, more preferably from 10 to 20% pendant azide functional groups, most preferably about 17% pendant azide functional groups.

The pendant azide functional groups may be distributed at intervals along the length of the linear copolymer chain.

In one form, the number and location of the pendant azide functional groups may be dictated by the number and location of polymerised glycidyl methacrylate residues in the copolymer backbone. For example, where the linear copolymer is a statistical copolymer, the polymerised glycidyl methacrylate residues may be statistically distributed along the length of the copolymer chain and the position of the residue may dictate the position of the pendant azide functionality.

In other embodiments, dendronised polymers of the invention may be prepared using divergent synthetic methods, which involve the growth of dendrons from the linear aliphatic copolymer backbone.

In another aspect, the present invention provides a method of preparing a hydrophilic, biocompatible dendronised polymer comprising the steps of:
    (i) providing a linear aliphatic copolymer backbone comprising a plurality of pendant functional groups;
    (ii) coupling a pendant functional group with a plurality of functional compounds to generate a branch forming part of a dendron and a plurality of functional groups;
    (iii) coupling the plurality of functional groups with a polyfunctional compound to extend the branch and generate a plurality of further functional groups;
    (iv) coupling each further functional group formed in step (iii) with a plurality of functional compounds to thereby generate a further branch in the dendron and a plurality of functional groups;
    (v) optionally, repeating at least one of steps (iii) and (iv) at least once.

In the above method, the repetition of steps (iii) and (iv) one or more times enables dendrons to be grown in sequential manner, to generate further dendron generations or half-generations that extend from the linear copolymer backbone.

Functional groups that are generated in each of steps (ii), (iii) and (iv) are generally terminal functional groups, which are capable of covalently reacting with functional compounds in order to extend the dendron branch.

In some embodiment of the divergent synthesis methods described herein, the linear aliphatic copolymer backbone can preferably comprise a plurality of pendant amino functional groups. The amino groups may be primary amino groups.

Where the linear aliphatic copolymer backbone comprises polymerised residues derived from glycidyl methacrylate (GMA), amino functionalisation of the copolymer backbone may be achieved by treating the copolymer with aqueous ammonium chloride and trimethylamine.

In one embodiment, the dendronised polymer of the invention comprises PAMAM dendrons and a method of preparing such a dendronised polymer may involve reacting pendant primary amino functional groups present on the linear aliphatic copolymer backbone with methyl acrylate under Michael addition under conditions sufficient to cause the Michael addition of the amino group to two molecules of the methyl acrylate. The reaction forms an initial adduct that is attached to the copolymer backbone via the pendant group. The initial adduct has terminal methyl ester moieties derived from the methyl acrylate. Following removal of unreacted methyl acrylate, this initial adduct is reacted with excess ethylenediamine (a polyfunctional compound) under conditions allowing one amine group of the ethylenediamine molecule to react with the methyl carboxylate groups of the adduct to form a first generation (G1) adduct having multiple amidoamine moieties. Following removal of unreacted ethylenediamine, this first generation adduct is then reacted with excess methyl acrylate under Michael addition conditions to form a second generation adduct having terminal methyl ester moieties. The second generation adduct is then reacted with excess ethylenediamine under amide forming conditions to produce a second generation (G2) poly(amidoamine) dendron extending from the linear copolymer backbone. Repeated and sequential reactions of the terminal amino moieties with methyl acrylate and ethylenediamine can then produce subsequent generations in the PAMAM dendron.

In one embodiment, where the dendronised polymer of the invention comprises PAMAM dendrons, the divergent synthesis method described herein employs methyl acrylate is a functional compound for reacting with amino functional groups, and ethylene diamine as a polyfunctional compound.

However, it would be appreciated that other functional molecules and polyfunctional compounds may be used if dendrons of different composition and/or functionality are desired.

In yet another aspect the present invention provides a method of preparing a hydrophilic, biocompatible dendronised polymer comprising the steps of:
(i) providing a linear aliphatic copolymer backbone comprising a plurality of pendant functional groups;
(ii) coupling a pendant functional group with a polyfunctional compound to generate a branch forming part of a dendron and a plurality of functional groups;
(iii) coupling the plurality of functional groups with a further polyfunctional compound to thereby generate a further branch in the dendron and a further plurality of functional groups; and
(iv) optionally, repeating step (iii) at least once.

In the above method, the repetition of step (iii) one or more times can enable a further full dendron generation to be produced in an iterative manner.

For example, where a poly(lysine) dendron is required, primary amino groups pendant from the linear copolymer backbone may react with the carboxylic acid functional group of lysine to attach the lysine to the copolymer, forming the first generation. Similarly, poly(propylene imine) (PPI) dendrons can synthesized in divergent manner by the reaction of pendant primary amino functional groups from the linear copolymer with acrylonitrile. Repetition of the coupling steps can then enable iterative growth of successive dendron generations from the copolymer backbone.

The linear aliphatic copolymer backbone described herein can be prepared by polymerising at least two ethylenically unsaturated co-monomers under a controlled free radical polymerisation process, wherein at least one of the co-monomers comprises a functional group that is (i) able to provide a pendant functional group capable participating in a click coupling reaction, or (ii) able to be modified to provide a pendant functional group capable of participating in a click coupling reaction, and if (ii), then the method further comprises the step of modifying the functional group to provide a pendant functional group capable of participating in a click coupling reaction.

The at least two ethylenically unsaturated co-monomers will generally be provided in a monomer composition in order to undergo reaction via free radical polymerisation.

In particular embodiments of the method, the controlled free radical polymerization process used for forming the linear aliphatic copolymer backbone is selected from the group consisting of atom transfer radical polymerisation (ATRP) and reversible addition-fragmentation transfer (RAFI) polymerisation, as described above.

Using a controlled free radical polymerisation process, suitable co-monomers and optionally, an initiator as a source of free radicals are combined and triggered to react under conditions of free radical polymerisation. In certain instances, the process for forming the copolymer backbone may involve forming a monomer composition comprising at least two hydrophilic ethylenically unsaturated monomers and subjecting the monomer composition to free radical polymerisation conditions.

One advantage associated with the use of a controlled free radical polymerisation process to synthesise the copolymer backbone is that a range of copolymers having controlled molecular weight and molecular weight distribution (i.e. polydispersity) can be prepared. Polymers from controlled polymerisation processes typically have molecular weight distributions, characterised by the polydispersity index ("PDI"), of less than or equal to 2. The PDI is defined by the ratio of the weight average molecular weight to the number average molecular weight, Mw/Mn. In some embodiments, the linear copolymer backbone of the dendronised polymer described herein has a polydispersity index (PDI) of no more than about 1.5, preferably no more than about 1.3.

In certain embodiments, atom transfer radical polymerisation (ATRP) is used to synthesise the linear aliphatic copolymer backbone of the dendronised polymer of the invention. ATRP is one of the most successful controlled or "living" radical processes developed for synthesising well-defined polymers. Conditions for performing a controlled free radical polymerisation process under ATRP would be known by a skilled person.

ATRP usually employs a transition metal complex as a catalyst with an alkyl halide as the initiator (R-X). Various transition metal complexes, namely those of Cu, Fe, Ru, Ni, Os, etc., have been employed as catalysts for ATRP. In an ATRP process, the dormant species is activated by the transition metal complex to generate radicals via a one electron transfer process. Simultaneously the transition metal is oxidized to higher oxidation state. This reversible process rapidly establishes an equilibrium that is predominately shifted to the side with very low radical concentrations. The number of polymer chains is determined by the number of initiators. Each growing chain has the same probability to propagate with monomers to form living/dormant polymer chains (R-Pn-X). As a result, polymers with similar molecular weights and narrow molecular weight distribution can be prepared. A discussion of ATRP may be found in *Chem. Rev.* 2001, 101, 2921-2990.

In one set of embodiments, the linear copolymer is provided by polymerising a monomer composition comprising at least two different hydrophilic ethylenically unsaturated monomers. The hydrophilic monomers can assist to confer hydrophilic properties to the dendronised polymer.

Ethylenically unsaturated monomers used to prepare the linear, aliphatic copolymer backbone may be dispersed or dissolved in appropriate solvent in the monomer composition.

In some embodiments, the solvent may be an aqueous solvent (including water and solvent mixtures comprising water) or an organic solvent. When an organic solvent is used, it is preferred that the solvent be compatible with the monomers. For example, it is preferred that the organic solvent be capable of solvating hydrophilic monomers.

In one set of embodiments, the monomer composition comprises a least one ethylenically unsaturated monomer selected from the group consisting of 2-hydroxyethyl acrylate, 2-methoxyethyl acrylate, N-acryloylamido-ethoxyethanol, N,N-dimethylacrylamide, N,N-diethylacrylamide, N-(2-hydroxyethyl)acrylamide, N-(hydroxymethyl)acrylamide, acrylamide, N-isopropyl acrylamide, methacrylamide, 2-hydroxyethyl methacrylate, 2-(dimethylamino)ethyl acrylate, 3-(dimethylamino)propyl acrylate, acrylic acid, methacrylic acid, 2-(dimethylamino)ethyl methacrylate, glycidyl methacrylate, 2-azido-1-hydroxyethyl methacrylate, and combinations thereof. These monomers are also generally hydrophilic monomers.

In one set of embodiments, the polymerisation of the monomer composition produce a linear statistical aliphatic copolymer that comprises statistically distributed polymerised residues of at least two different ethylenically unsaturated monomers.

In some embodiments, the monomer composition comprises at least two ethylenically unsaturated co-monomers, wherein at least one of the co-monomers comprises a functional group that is able to be modified to provide a pendant functional group that is capable of enabling dendron attachment to the copolymer.

In one embodiment, at least one of the co-monomers comprises a functional group that is able to be modified to provide a pendant functional group that is capable of participating in a coupling reaction, such as a covalent coupling reaction or an oxidative coupling reaction.

In some particular embodiments, the monomer composition comprises at least two ethylenically unsaturated co-monomers, wherein at least one of the co-monomers comprises a functional group that is able to be modified to provide a pendant functional group capable of participating in a click coupling reaction. In such embodiments, the method of the invention described herein further comprises the step of modifying the functional group of the formed linear copolymer to provide a pendant functional group capable of participating in a click coupling reaction.

In one preference, the monomer composition may comprise an ethylenically unsaturated monomer comprising a glycidyl functional group. In such embodiments, the method further comprises the step of modifying said glycidyl functional group to provide a pendant functional group capable of participating in a click coupling reaction. As an example, the glycidyl functional group may be modified by reacting with sodium azide ($NaN_3$), resulting in ring opening of the epoxy group and substitution of the monomer, or polymerised monomer residue, with an azido functionality.

A monomer comprising a glycidyl functional group may therefore provide a convenient avenue for introducing functional groups that are subsequently able to form click reaction products upon coupling with an appropriately functionalised dendron.

A skilled person would understand that the epoxy moiety of glycidyl methacrylate may be readily modified by reaction with an appropriate reagent to provide a functional group that is capable of participating in a click coupling reaction. For example, a linear copolymer comprising polymerised residues derived from glycidyl methacrylate will have pendant epoxy functional groups that may be ring opened by sodium azide ($NaN_3$) via a nucleophilic substitution reaction under appropriate conditions. The ring opening reaction will then result in the introduction of a pendant azido functional group from the linear copolymer. In this manner, suitable pendant functional groups capable of participating in a click coupling reaction may be distributed at intervals along the linear copolymer chain.

In one set of embodiments, the monomer composition comprises glycidyl methacrylate and at least one other ethylenically unsaturated monomer.

In one embodiment, the linear copolymer backbone is provided by polymerising:
(a) a first monomer which is glycidyl methacrylate; and
(b) a second monomer which is selected from the group consisting of 2-hydroxyethyl acrylate, 2-methoxyethyl acrylate, N-acryloylamido-ethoxyethanol, N,N-dimethylacrylamide, N,N-diethylacrylamide, N-(2-hydroxyethyl)acrylamide, N-(hydroxymethyl)acrylamide, acrylamide, N-isopropyl acrylamide, methacrylamide, 2-hydroxyethyl methacrylate, 2-(dimethylamino)ethyl acrylate, 3-(dimethylamino)propyl acrylate, acrylic acid, methacrylic acid, 2-(dimethylamino)ethyl methacrylate, and 2-azido-1-hydroxyethyl methacrylate.

In one preference, the second monomer is 2-hydroxyethyl methacrylate (HEMA). In such embodiments, the monomer composition comprises glycidyl methacrylate and 2-hydroxyethyl methacrylate.

2-hydroxyethyl methacrylate (HEMA) can advantageously provide a highly hydrophilic spacer between glycidyl methacrylate (GMA) monomeric units in the linear copolymer backbone to provide hydrophilicity, flexibility and biocompatibility.

The first and second monomers may be polymerised in a suitable molar ratio. The molar ratio can determine the quantity of glycidyl methacrylate residues in the linear copolymer and may ultimately influence the dendron density in the resultant dendronised polymer.

In one embodiment, the molar ratio between the first and second co-monomers may be in the range of from 3:97 to 30:70.

Thus in some embodiments, the monomer composition may comprise glycidyl methacrylate in an amount of from about 3 to 30 mol % of the total amount of monomer, with the second co-monomer being in amount of from about 97 to 70 mol % of the total amount of monomer in the composition.

In some embodiments, the molar ratio between the first and second co-monomers may be in a range of from about 5:95 to 25:75, or in a range of from about 10:90 to 20:80. In an exemplary embodiment, the molar ratio between the first and second co-monomers is approximately 17:83. In another exemplary embodiment, the molar ratio between the first and second co-monomers is approximately 25:75.

The linear aliphatic copolymer backbone produced by the method described herein may be of any suitable size or molecular weight and the controlled free radical polymerisation method employed allows the molecular weight of the copolymer to be controlled and tailored to suit particular dendrons of selected size or composition, dendron densities, biomolecules, and/or applications of use.

In one embodiment, the linear copolymer backbone is about 5 kDa or larger. The copolymer backbone may have a molecular weight of no more than about 40 kDa. In one preference, the linear copolymer backbone has a molecular weight in a range of from about 15 to 25 kDa.

Dendrons used in the method of the invention have been described above. The dendrons can be pre-formed and have a functional group at its focal point that is capable of reacting with a functional group that is pendant from the linear aliphatic copolymer chain.

In one form, where the linear copolymer comprises azide functional groups, each dendron comprises an alkyne functional group at its focal point.

In another form, where the linear copolymer comprises alkyne functional groups, each dendron comprises an azide functional group at its focal point.

The azide and alkyne functional groups are suitable where the click coupling reaction involves an azide-alkyne cycloaddition.

The dendrons utilised in the method of the invention may be of any appropriate size and composition. However, it is preferable that the dendrons be hydrophilic and biocompatible, with low toxicity to biological material.

In one form, the dendrons are PAMAM dendrons as described herein. The PAMAM dendrons may each be G2 to G5 PAMAM dendrons, including half generation dendrons. In some embodiments, the PAMAM dendrons may each be G4-G5 dendrons.

The PAMAM dendrons may each comprise a functional group at its focal point, the focal point functional group being capable of reacting with a functional group pendant from the copolymer backbone to form a click reaction product under click chemistry conditions.

In a particular embodiment, each PAMAM dendron comprises an alkyne functional group at its focal point.

The method of the invention also comprises the step of reacting the pendant functional groups on the copolymer backbone with the functional groups at the focal point of the dendrons under click chemistry conditions to form click reaction product that couples the dendrons to the copolymer backbone.

Click chemistry conditions suitable for forming click reaction products have been extensively described. For example, a number of click chemistry reactions have been described in *Pharm. Res.* 2008, 25(10): 2216-2230, the disclosure of which is incorporated herein by reference.

In some embodiments, the click reaction product is a triazole that is formed by reacting an azide and alkyne functional group via a copper catalysed 1,3-cycloaddition reaction.

Reaction between the copolymer backbone and the dendrons may be achieved by combining the copolymer backbone and the dendrons in a reaction mixture, then allowing the functional groups on the copolymer and dendrons to react and form a click reaction product that couples the dendrons to the copolymer. The click chemistry reaction can proceed with high specificity and high yield to thereby form a dendronised polymer of the invention.

Dendrons utilised in the method described herein may comprise terminal functional groups extending from an outermost generation of the dendrons. The terminal functional groups may be modified alter the functionality of the dendronised polymer, or to enhance the efficacy of the dendronised polymer for the delivery of biomolecules in vivo.

In some embodiments, the method of the invention may comprise the step of reacting at least one terminal functional group on each dendron with an agent to thereby functionalise the periphery of the dendrons. The dendrons may be coupled to the copolymer backbone when the terminal functional groups are modified with the agent.

In one form, one or more dendrons are functionalised with a group selected from the group consisting of a fluoro group, a stealth group, a targeting ligand, a fluorescent group, and combinations thereof, at its periphery.

In some embodiments, one or more dendrons are functionalised with a fluoro group. In such embodiments, terminal functional groups may be reacted with a fluorination agent in order to introduce fluoro groups to the dendron. Accordingly, the method of the invention may comprise the step of reacting at least one terminal functional group on each dendron with a fluorination agent to thereby from dendrons with at least terminal fluoro group.

Fluorination of one or more terminal functional groups on the dendrons may be desirable to form at least partially fluorinated dendrons. It has been found that fluorinated dendrons can assist to provide enhanced transfection ability.

In some embodiments, the dendrons are PAMAM dendrons. The PAMAM dendrons comprise a plurality of terminal amino functional groups. One or more of the terminal amino groups may be reacted with a fluorination agent to form terminal fluoro groups. For example, terminal amino groups may react with a fluorination agent such as heptafluorobutyric anhydride or glycidyl 2,2,3,3,4,4,5,5-octafluoropentyl ether.

An example of a reaction scheme for fluorination of terminal PAMAM primary amines using heptafluorobutyric anhydride is shown below.

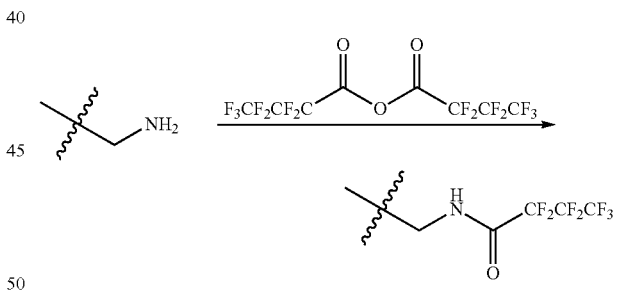

It will be appreciated that PAMAM dendrons will comprise primary amino functional groups as terminal functional groups at the periphery of the dendron and tertiary amino functional groups within their internal structure. The terminal amino functional groups are able to carry a positive charge at physiological pH, thereby allowing the dendronised polymer to bear a net positive charge and become cationic. The cationic dendronised polymer is thus capable of interacting with anionic biomolecules such as DNA.

In some embodiments, fluorination of the primary amino functional groups can allow for control of primary/tertiary amino content within the dendronised polymer, which can influence optimal transfection efficacy.

The terminal fluoro groups may be fluoroalkyl groups, preferably perfluoroalkyl groups. An exemplary fluoroalkyl group is a heptafluoropropyl group.

The fluorination agent for introducing terminal fluoro groups may be selected from a number of suitable agents capable of reacting with an amino functional group to result in substitution of the amino functionality with a fluoro group. In one embodiment, the fluorination agent is a perfluoro anhydride. An example of a perfluoro anhydride is heptafluoro butyric anhydride.

In some embodiments, one or more dendrons are functionalised with a fluorescent group, a stealth group or a targeting ligand. In such embodiments, terminal functional groups may be reacted with a fluorescent agent, a stealth agent or a targeting agent in order to introduce fluorescent groups, stealth groups and/or targeting ligands to the dendron.

Accordingly, the method of the invention may comprise the step of reacting at least one terminal functional group on each dendron with an agent selected from the group consisting of a fluorescent agent, a stealth agent and a targeting agent to thereby from dendrons functionalised with the agent.

Stealth agents and targeting agents may have complementary functional groups that are able to react with terminal functional groups (e.g. terminal amino groups) at the periphery of a dendron by covalent bonding reactions. In this way, a fluorescent agent, a stealth group or a targeting ligand may be attached to the dendron via a covalent bond.

An example of a fluorescent group is cyanine-7 (Cy7) fluorescent dye.

An example of a stealth group is poly(ethylene glycol) (PEG).

The targeting ligand may be selected from antibodies, aptamers, cholesterol and its derivatives, folate compounds or folate conjugates, transferrin, saccharides and cell-penetrating peptides. An example of a targeting ligand is cyclic RGD peptide.

Dendronised polymers of the present invention are suitably able to form complexes (also described herein as "polyplexes") with biomolecules and thus may act as carriers for the intracellular delivery of the biomolecules.

In another aspect, the present invention provides a complex comprising a biomolecule and a dendronised polymer of any one of the embodiments described herein.

Complexes described herein may comprise a biomolecule selected from the group consisting of a nucleic acid molecule, a protein molecule, a therapeutically active agent, and combinations thereof, which are capable of binding with the dendronised polymer through interactions such as electrostatic interactions.

In one set of embodiments the biomolecule is an agent capable of modulating gene expression in a cell (e.g., gene editing). Modulators of gene expression include molecules capable of activating or inhibiting the expression of endogenous genes, molecules capable of inducing or enhancing the expression of endogenous genes and molecules capable of introducing and expressing one or more exogenous genes in a cell. Suitable modulators of gene expression will be familiar to persons skilled in the art, illustrative examples of which include nucleic acid molecules such as RNA or DNA (including double-stranded or single-stranded) and peptides. In an embodiment, the biomolecule is a zinc finger or a transcription activator-like effectors (TALE), and/or a nucleic acid molecule encoding a zinc finger or TALE.

In an embodiment, the biomolecule comprises a nucleic acid sequence encoding an exogenous (recombinant) protein. Suitable nucleic acid sequences for recombinant protein expression will be familiar to persons skilled in the art, illustrative examples of which include viral proteins and immunogens. The nucleic acid sequence may be operably linked to a regulatory sequence such as a promoter that capable of driving the expression of the nucleic acid sequence. Alternatively, the expression of the recombinant protein may be driven by endogenous promoters in the transfected cell.

Suitable DNA molecules include antisense, as well as sense (e.g. coding and/or regulatory) DNA molecules. Antisense DNA molecules include short oligonucleotides. Persons skilled in the art are well equipped to design suitable inhibitory oligonucleotides. Other examples of inhibitory DNA molecules include those encoding interfering RNAs, such as shRNA and siRNA. Yet another illustrative example of an inhibitor of gene expression is catalytic DNA, also referred to as DNAzymes.

Illustrative examples of suitable RNA molecules capable of inhibiting gene expression in a cell, also referred to herein as RNA inference molecules, include siRNA, dsRNA, stRNA, shRNA and miRNA (e.g. short temporal RNAs and small modulatory RNAs), ribozymes, and guide or CRISPR RNAs used in combination with the Cas or other nucleases (van der Oost et al. 2014; *Nat Rev Microbiol;* 12(7):479-92).

In an embodiment, the biomolecule comprises an engineered Clustered Regularly Interspersed Short Palindromic Repeat-CRISPR associated gene editing system (CRISPR).

Clustered regularly interspaced short palindromic repeats (CRISPR) are segments of prokaryotic DNA containing short repetitions of base sequences. Each repetition is followed by short segments of "spacer DNA" from previous exposures to a bacteriophage virus or plasmid. For example, the "CRISPR-Cas9 system" is a prokaryotic immune system that confers resistance to foreign genetic elements such as those present within plasmids and phages, and provides a form of acquired immunity. CRISPR spacers recognize and cut these exogenous genetic elements in a manner analogous to RNA interference in eukaryotic organisms. CRISPRs are found in approximately 40% of sequenced bacterial genomes and 90% of sequenced archaea.

Alternatively, CRISPR-mediated gene editing systems can also be used to enable the precise transactivation of dormant genes, such as tumour suppressor genes. For example, CRISPR-mediated gene activation (CRISPRa) using deactivated Cas9 (dCas9) fusion proteins to recruit transcriptional activators to enable multiple fold enhanced activation of endogenous genes in vitro (see, for example, Perez-Pinera, P. et al. RNA-guided gene activation by CRISPR-Cas9-based transcription factors. *Nat. Methods* 10, 973-976 (2013)).

By delivering the Cas nuclease and appropriate guide RNAs into a cell, the cell's genome can be cut at a desired location, allowing existing genes to be removed and/or new ones added. CRISPRs have been used in concert with specific endonuclease enzymes for genome editing and gene regulation in various species. More recently, CRISPR-mediated gene editing systems have been developed with new enzyme systems, including C2c2, Cpf1, nickase, split, enhanced and other Cas9 variants, catalytically inactive Cas9 linked to various nuclease or gene-regulating domains. Further information regarding CRISPR can be found, for example, in WO 2013/188638, WO 2014/093622 and Doudna et al., (Methods Enzymol; 2014; 546).

In an embodiment, the biomolecule is a nucleic acid molecule operably linked to a promoter capable of driving the expression of a nucleic acid sequence, such as a nucleic acid sequence encoding the Cas9 polypeptide and/or single- or multiple-guide RNA molecules for the target sequence, or portions thereof. In another embodiment, the biomolecule is incorporated into an expression vector and/or plasmid that is suitable for replication and integration of nucleic acid into the genome of a cell. Suitable vectors and plasmids will be familiar to persons skilled in the art and may comprise transcription and translation terminators, initiation sequences and promoters useful for regulation of the expression of the target sequence.

In another embodiment, the biomolecule is a mediator of RNA interference. RNA interference (RNAi) is useful for specifically inhibiting gene expression and subsequent protein synthesis. Without being limited by theory or a particular mode of application, Waterhouse and collaborators have provided a model for the mechanism by which dsRNA can be used to reduce protein production (Waterhouse et al., 1998; *Proc Natl Acad Sci USA* 95:13959-13964). This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering WO 99/32619, WO 99/53050, WO 99/49029, WO 01/34815 and Waterhouse et al., 1998; supra.

Preferred small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the cell in which it is to be introduced, e.g., as determined by standard BLAST search.

The terms "double stranded RNA" or "dsRNA" refer to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA, comprises a dsRNA molecule.

Other suitable RNA interference molecules include unmodified and modified double stranded (ds) RNA molecules including, short-temporal RNA (stRNA), small interfering RNA (siRNA), short-hairpin RNA (shRNA), microRNA (miRNA) and double-stranded RNA (dsRNA). The dsRNA molecules (e.g. siRNA) also may contain 3' overhangs, such as 3'UU or 3'TT overhangs.

Suitable siRNAs also include small hairpin (also called stem loop) RNAs (shRNAs). In an embodiment, the shRNA comprises short, e.g. about 19 to about 25 nucleotide, antisense strand, followed by a nucleotide loop of about 5 to about 9 nucleotides, and the analogous sense strand. Alternatively, the sense strand may precede the nucleotide loop structure and the antisense strand may follow.

In an embodiment, the biomolecule is an siRNA, shRNA or miRNA molecule.

RNA interference molecules, such as siRNA, shRNA and miRNA molecules, can be readily designed by persons skilled in the art having regard to the nucleic acid sequence of the target gene.

The phrase "inhibition of gene expression" and the like typically refer to a decrease in the level of mRNA in a cell for a target gene. In some embodiments, the introduction of an inhibitory biomolecule in a cell will decrease the level of mRNA by at least about 5%, preferably by at least about 10%, preferably by at least about 20%, preferably by at least about 30%, preferably by at least about 40%, preferably by at least about 50%, preferably by at least about 60%, preferably by at least about 70%, preferably by at least about 80%, preferably by at least about 90%, preferably by at least about 95%, preferably by at least about 99%, or preferably by about 100% of the mRNA level found in the cell in the absence of the biomolecule.

Conversely, the phrase "Inducing or enhancing gene expression" and the like refer to an increase in the level of mRNA in a cell for an endogenous (i.e, homologous or native) target gene. In some embodiments, the introduction of the biomolecule in a cell will increase the level of endogenous mRNA by at least about 2-fold, preferably by at least about 5-fold, preferably by at least about 10-fold, preferably by at least about 50-fold, preferably by at least about 100-fold, preferably by at least about 50%, preferably by at least about 500-fold preferably by at least about 1000-fold, preferably by at least about 5000-fold, preferably by at least about 10,000-fold, preferably by at least about 15,000-fold, preferably by at least about 20,000-fold, or preferably by about 50,000-fold of the mRNA level found in the cell in the absence of the biomolecule.

In some embodiments, the biomolecule is has a molecular weight in a range of from about 1 to 15 kb.

In one set of embodiments the biomolecule comprises a nuclease.

In some embodiments, the biomolecule comprises a peptide or protein.

In some embodiments, the biomolecule is a ribonucleoprotein (RNP).

In particular embodiments, the complex comprises a biomolecule is selected from the group consisting of siRNA, a zinc finger (ZF) protein, a transcription activator-like effector (TALE), a protein molecule, a ribonucleoprotein (RNP), or a CRISPR mediated gene editing system.

In particular embodiments, the complex may comprise a plurality of biomolecules, such as for example, a plurality of plasmids. Thus the dendronised polymer of the invention and complexes comprising the dendronised polymer can enable multiple biomolecules to be delivered to a cell simultaneously.

In a further aspect, the present invention also provides a method of delivering a biomolecule into a cell or tissue comprising exposing the cell or tissue to a complex comprising the biomolecule and a dendronised polymer of any one of the embodiments described herein.

The complex may be delivered to a cell or tissue for exposure to the cell or tissue, whether the cell or tissue is healthy or in a diseased state. Contacting the cells or tissue with the complex described herein results in internalization of the complex. Contacting the cells or tissue in vitro or ex vivo may utilize any standard or well-known method that brings the complex into contact with the cell or tissue such that internalization of the complex is facilitated. In vitro or ex vivo this is achieved by exposing the cells or tissue to the complex in a suitable medium. For in vivo applications, any known method of administration is suitable as described herein. Without being limiting administration may be orally, intranasally or through intravenous (IV), intramuscular (IM) or intraperitoneal (IP) injection.

In yet another aspect, the present invention also provides a method for the treatment of cancer comprising the administration of an effective amount of a complex comprising the biomolecule and a dendronised polymer of any one of the embodiments described herein to a subject in need thereof.

The effective amount of the complex can be determined by the person skilled in the art, by routine experimentation. This may be determined on a case-by-case basis. For example, the effective amount or individual dose level of the administered complex will depend on a variety of factors including the type and severity of the condition being treated and the stage of the condition; the activity and nature of the specific biomolecule employed; the age, body weight, general health, sex and diet of the subject; the time of administration; the route of administration; the duration of the treatment; drugs used in combination or coincidental with the treatment, together with other related factors well known in medicine. It will also be apparent to one of ordinary skill in the art that the optimal course of treatment, such as, the number of doses administered per day, week (or other frequency) for a defined number of days, weeks (or other length of time) can be ascertained by those skilled in the art without undue experimentation.

Methods of the present invention are suitable for the treatment of any cancer. By way of example, suitable cancers include prostate cancer, breast cancer, colon cancer, lung cancer, pancreatic cancer, kidney cancer, bone cancer, ovarian cancer, testicular cancer, bowel cancer, stomach cancer, a head and neck cancer, a brain tumour, acute myeloid leukaemia, acute lymphoblastic leukaemia, a sarcoma such as osteosarcoma or ewings disease, non hodgkins lymphoma, chronic lymphatic leukaemia, hodgkins disease, or a myeloproliferative disorder such as essential thrombocythaemia, polycythaemia *rubera vera* or myelofibrosis. In particular embodiments, the cancer is breast cancer.

The method of the invention may be employed as an adjunct to other suitable cancer treatments such as, for example, chemotherapy, radiotherapy, monoclonal antibody therapy, hormone therapy, the administration of checkpoint inhibitors, T cell therapy such as chimeric antigen receptor (CAR) T cell therapy and stem cell transplantation, such as autologous stem cell transplantation.

The invention also provides a composition for altering the expression of at least one gene product in a subject, the composition comprising a complex of a nuclease and a dendronised polymer of any one of the embodiments described herein. In one set of embodiments the composition activates the expression of at least one gene product in a subject.

Dendronised polymers of the invention are fully synthetic and biocompatible macromolecular species with a high degree of flexibility and sufficient cationic charge to enable high DNA packing density for intracellular delivery, and sufficient tertiary amines to facilitate intracellular release of the cargo.

In particular, dendronised polymers of the invention are able to provide the flexibility and superior packing density and low cytotoxicity whist maintaining the key chemical characteristics of higher generation dendrimers.

The dendronised polymers of the invention are also biocompatible and non-toxic and are able to deliver a desired biomolecule to a target site.

The dendronised polymers can be prepared using a highly controlled synthetic strategy that involves controlled free radical polymerisation, and in some embodiments also click chemistry, to engineer a library of dendritic copolymers. The use of synthetic polymers prepared through controlled polymerisation of a variety of monomers provides the ability to control the polymer backbone in terms of size and number of functional groups available for substitution with dendrons. Thus, this allows one to control ultimate polymer size, flexibility and charge through the use of different generations of dendrons.

With the synthetic approach described herein it is possible to methodically tune and optimise the platform for transfection of both small and large plasmids.

Importantly the design strategy overcomes all the challenges associated with the traditional cationic macromolecules in the delivery of large genome editing tools with utmost efficiency.

For instance, the synthetic approach described herein enables dendronised polymers to be designed and synthesised to have an optimal conformation and level of flexibility that maximises the interaction between dendrons and (multiple) pDNAs, forming stable polyplexes. Additionally, through the selection of dendrons of suitable composition and size, a balance between charge density and buffering ability for plasmid binding and release can be achieved. Furthermore, fluorination of the dendronised polymer facilitates the internalisation and release of polyplexes. While previous studies have used higher generation (e.g. G4 to G7) PAMAM dendrimers to try to balance charge density and buffering ability, the restrictions imposed by spherical architectures (including branch flexibility) have not previously allowed each of these factors to be varied independently.

The present invention enables high transfection efficiencies and packaging capacity can be achieved for the delivery of zinc fingers, TALEs, protein molecules and CRISPR/dCas9 platforms.

Dendronised polymers of the invention are useful alternatives to present commercially available transfection agents and show improved transfection efficiency as compared to commercial agents, particularly with respect to transfection of combination of DNA strands of varying size. In particular, the dendronised polymers of the invention have advantageously been found to be capable of providing simultaneous delivery of DNA strands of varying size.

In particular, the linear dendronised polymers represent a controllable, synthetic platform that has enabled systematic engineering of highly efficient and nontoxic agents for the delivery of precise gene editing tools such as CRISPR/Cas9 and TALEs. Rapid advances are being made both in designing novel genome-editing tools with increased specificity whilst limiting off-target effects, and in the development of methods with increased sensitivity for assessing this specificity genome-wide. However, the development of delivery technologies that cater for large plasmid sizes associated with these technologies has been limited. This limitation has to be overcome for successful clinical translation of these technologies. Herein we have shown that by carefully redesigning the architecture of macromolecular non-viral vectors, it is possible to overcome both the packaging capacity and cytotoxicity issues associated with higher generation dendrimers, whilst maintaining the key attractive features of traditional dendrimers, such as highly controlled synthesis. The delivery platform of the present invention therefore offers the possibility of incorporating features of nanoscale therapeutic agents such as multimodality and targeted delivery for in vivo translation of the genome editing tools.

The invention will now be described with reference to the following examples. However, it is to be understood that the examples are provided by way of illustration of the invention and that they are in no way limiting to the scope of the invention.

EXAMPLES

Example 1

Materials and Methods
Chemical Synthesis and Characterisation

All chemicals were purchased from Sigma Aldrich and used without further purification unless otherwise stated. Poly(amido amine) G5.0 dendrimer with an ethylene diamine core was purchased (cat. 536709) as a 5 wt. % solution in methanol and so was dialysed against distilled water and lyophilised prior to being used in vitro. Cyanine7 NHS ester (Cy7-NHS) was purchased from Lumiprobe. Peptides (H-DfC(1230)RG-cyclic, 99% purity 14 and H-DfC(51)RG-cyclic, 97% purity 13) were custom designed and synthesized by Mimotopes (Melbourne, Australia). SM(PEG)12 (Thermo Scientific, 100 mg) was diluted by adding 360 µL of dry DMSO, as per manufacturer's protocol, and stored under argon at −20° C.

Instrumental Characterisation Methods 1H and 19F NMR spectra were measured using a Varian 400 MHz spectrometer and Bruker 500 MHz spectrometer, using CD3OD as the solvent for copolymers, aminated copolymers, dendronised polymers and fluorinated compounds. The chemical shifts were referenced to the solvent peak, $\delta=3.31$ ppm for CD3OD. For 19F spectra, hexafluorobenzene was used as a standard, with a chemical shift of $\delta=-164.9$ ppm. IR spectra were obtained using PerkinElmer Spectrum One FT-IR spectrometer. Gel permeation chromatography (GPC) was used to determine the molecular weight and polydispersity index of polymers (Waters Styragel HR 4 DMF 4.6×300 mm column, 5 µm). Agilent Technologies 1100 Series GPC and Agilent GPC software were utilized for measurements and data analysis respectively. Measurements were taken using DMF as the eluent at a flow rate of 0.3 mL/min at 50° C., and calibrated against poly(methyl methacrylate) (PMMA) standard. Elemental analysis was conducted at the Campbell Microanalytical Laboratory, University of Otago. The carbon, hydrogen and nitrogen content of each sample were determined via the 'flash combustion' method using a Carlo Erba Elemental Analyser EA1108. The fluorine content of fluorinated polymers was determined via the standard addition method using a fluoride selective ion electrode connected to a Eutech 2700 pH meter.

Molecular Dynamics

All MD simulations were performed using GROMACS (Groningen Machine for Chemical Simulations) package, version 4.6.5 with the GROMOS 54a7 forcefield updated for non-standard atom types. All simulations were performed under periodic boundary conditions in a square box, with solvent (water) described using the simple point charge (SPC) water model. The structures were drawn and converted to PDB (protein database) files using ChemDraw. Structures were uploaded to the ATb (Automated Topology Builder and Repository, atb.uq.edu.au), where MD files were generated for the optimised geometry using preliminary DFT Hessian QM calculations. The united atom representation for the topology was used in all cases, whereby forces acting on the hydrogens are projected onto the heavy atoms to which they were attached. Counterions (Cl⁻) were included to balance the charge. LINCS algorithm was used to constrain the lengths of the covalent bonds in the polymer. Simulations were conducted in the NPT-ensemble at T=300 K and P=1 bar, pressure coupling was isotropic. Three simulations were run for 100 ns, giving a total of 300 ns simulation time for each system, with data collected every 50 ps. Images were produced using VMD software, graphs produced in Xmgrace.

Plasmid Binding

Plasmids

The pcDNA3.1-dCas9-VP64 (Cat. No.: 47107, Addgene) plasmid, with a CMV promoter and VP64 at the C-terminal, was provided by Charles Gersbach (Duke University, Durham, USA). The pcDNA-dCas9-No Effector with HA tagged at the C-terminus was purchased from Addgene (Cat. No: 47106, Addgene). All dCas9 vectors co-transfected with four single guided RNAs (sgRNAs) with custom-designed modification against MASPIN target sequences in MASPIN proximal promoters, using the crispr.mit.edu website tool and cloned into BbsI sites in the pSP-gRNA (sgRNA) expression vector (Cat No: 47108, Addgene), following Gersbach's protocol (Kabadi A M, Gersbach C A. Engineering synthetic TALE and CRISPR/Cas9 transcription factors for regulating gene expression. *Methods* 2014, 69, 188-197). All dCas9 constructs used an inactivated form of *S. pyogenes* Cas9 protein harboring D10A and H840A mutation.

TALE was custom-designed by Genecopoeia TALE-TF service and fused with effector domain VP64 at -99 (TALE-99) and -128 (TALE-128). Each TALE targets two more nucleotides than its corresponding ZF (a total of 20 nt), designed to start at the nearest thymine nucleotide. Zinc finger (ZF) fused with effector domain VP64 at -97 (ZF-97) and -126 (ZP-126) were as described previously (Beltran A, Parikh S, Liu Y, Cuevas B D, Johnson G L, Futscher B W, Blancafort P. Re-activation of a dormant tumor suppressor gene maspin by designed transcription factors. *Oncogene* 2007, 26, 2791-2798).

All dCas9 constructs used an inactivated form of *S. pyogenes* Cas9 protein with two mutations in D10A and H840A. pcDNA-dCas9-No effector (Addgene plasmid #47106) was a gift from Charles Gersbach. pcDNA-dCas9-VPR with VP64, p65 and Rta fused to its C-terminus (Addgene plasmid #63798) was a gift from George Church. MS2-P65-HSF1_GFP (Addgene plasmid #61423), expressing the SAM helper complex with a 2A GFP, was a gift from Feng Zhang. The Benchling CRISPR design tool was used to select sgRNA target sequences in the MASPIN and CCN6 proximal promoters. Annealed oligonucleotides (Integrated DNA Technologies, Singapore) containing the sgRNA target sequences were cloned into BbsI sites in the sgRNA(MS2) cloning backbone (Plasmid #61424), which was a gift from Feng Zhang. Plasmids were prepared using the QIAGEN Plasmid Maxi Kit (QIAGEN)(Zinc Finger (ZF): 6.1 kb; TALE: 9.3 kb; CRISPR/dCas9: 9.8 kpb; guides: about 3.2 kb each).

Gel Retardation Assays

Polymer solutions were made up to a final concentration of 10 mM primary amine in filtered milli-Q water (calculations based on elemental results). Solutions were mixed with pDNA at various N/P ratios and incubated at room temperature for 30 min. Binding studies were conducted in water without the presence of additional buffers. The samples were electrophoresed on 1% w/v agarose gels in sodium borate (SB) buffer, stained with ethidium bromide (EtBr). Images were taken using ChemiDoc MP Imaging System.

DLS and Zeta Potential Optimisations

Polymer solutions were mixed with pDNA at appropriate N/P ratios and incubated at room temperature for 30 min. Size and zeta potential of the resulting polyplexes were characterised using dynamic light scattering (Zetasizer Nano ZS), using a 4 mW He—Ne laser operating at 633 nm with a scattering angle of 1730. Measurements were taken in triplicate after an initial equilibration period of 2 min. For calibration of the measurements 'material' was defined as PGMA (refractive index of 1.515 and absorbance of 0.05) and 'dispersant' was defined as water at 25° C. (refractive index at 1.330 and viscosity of 0.887). The intensity-weighted zeta potential and hydrodynamic radius of the polyplexes is presented as mean±standard deviation. All zeta potential measurements were taken at pH≈6.

N/P ratios were calculated based on elemental analysis data (for nitrogen content) and calculated pDNA phosphorus content. Polymer formulations were screened at two different N/P ratios, 5 and 10.

General Transfection Protocol Polymer stock solutions were made to a concentration of 10 mM primary amines in sterile Milli-Q water. Cells were seeded in standard 12-well plates 16-24 h prior to transfection, at concentrations resulting in 50-60% confluency at time of transfection. Polymer solution and pDNA were diluted to working concentrations in Opti-MEM reduced serum media (Gibco). For cotransfection experiments, pDNAs were mixed at 1:1 mass ratio. Polymer and pDNA solutions were thoroughly mixed to achieve desired N/P ratio for 1 mg DNA, and incubated at r.t. for 30 min. Cells were washed with PBS to remove serum, and media was replaced with 300 mL Opti-MEM (Gibco). Transfection cocktails were added and cells were incubated for 4 h before addition of 570 mL complete culture medium. Cells were incubated for a further 44 h. Commercial transfection agent Lipofectamine® 2000 (Thermo Fisher Scientific), was used according to the manufacturer's protocol at an optimised ratio of 1 µL·µg$^{-1}$ pDNA. Transfection efficiency was assessed using EGFP and mCherry reporter vectors, visualised with epifluorescence microscopy (Olympus IX-51, U-MGFPHQ and UMRFPHQ filters) and quantified with flow cytometry (BDFACSCanto H for EGFP experiments, BD LSRFortessa for cotransfections).

Cell Culture and Gene Transfection

HEK293T (human embryonic kidney cell line, ATCC) and HeLa (human cervical adenocarcinoma cell line) were cultured in Dulbecco's Modified Eagle's Medium (DMEM, Gibco) with 10% heat-inactivated Fetal Bovine Serum (FBS, Life Technologies). MCF-7 (human breast adenocarcinoma cell line, ATCC) were cultured in Minimum Essential Medium α (MEM α, Gibco) supplemented with 1% sodium bicarbonate, 10% PBS. Cell lines were seeded in 12-well plates (Corning Costar, Sigma Aldrich). Cell seeding densities are summarised in Table 1. No antibiotic/antimycotic was used.

TABLE 1

Seeding densities of cell lines used for transfected experiments.

| Cell line | Seeding Density (cells/well) |
|---|---|
| HEK293T | $2.0 \times 10^5$ |
| MCF-7 | $1.4 \times 10^5$ |
| HeLa | $1.8 \times 10^5$ |

For transfection, polymer solution and pDNA were diluted to the required concentration in Opti-MEM reduced serum media (Gibco). For cotransfection experiments, plasmid DNA was mixed at a 1:1 ratio based on mass. Polymer and DNA solutions were mixed so as to achieve the optimal N/P ratio for 1 µg DNA in total volume of 130 µL, and incubated at room temperature for 30 min. Commercial transfection agent Lipofectamine 2000 (Invitrogen) was used as a standard according to the manufacturer's protocol. 130 µL of polyplex solution was transferred to the appropriate well containing 300 µL of Opti-MEM. After a 4 h incubation period, an additional 570 µL of the appropriate complete culture medium was added and experiment was incubated for a further 44 h, giving a total transfection time of 48 h.

Transfection efficiency was observed using fluorescent microscopy and quantified via flow cytometry. Fluorescent and phase contrast images were taken using an Olympus IX-71 inverted microscope (U-MGFPHQ and U-MRFPHQ filters). Flow cytometry of EGFP transfections were conducted using BD FACSCantoII flow cytometer, cotransfection experiments were analysed using LSRII Fortessa flow cytometer. In preparation for flow cytometry cells were washed twice with phosphate buffered saline (PBS) and harvested with trypsin (Life Technologies). Cells were collected via centrifugation (300 g, 5 min) and washed in 500 µL FACS buffer (2% FBS, 4 mM EDTA in PBS). Cells were centrifuged again (300 g, 5 min) and resuspended in 200 µL of FACS buffer for flow analysis. Samples were acquired using BD FACS Diva software. EGFP was excited by 488 nm laser, and emission was measured with 502 nm long pass and 530/30 nm band pass filters; RFP was excited by 561 nm laser, and emission was measured with 600 nm long pass and 610/20 mm band pass filters. 30,000 single cell events, gated on forward scatter area vs height, were recorded for analysis. Post-acquisition analysis was performed on FlowJo vX software.

Cytotoxicity

Cytotoxicity was quantified by cell viability following 24 or 48 h incubation of cells with transfection cocktails. HEK293T, HeLa, or MCF-7 cells were seeded in poly-L-lysine (Sigma) treated 96-well opaque white plates (Corning) at densities as shown below, Table 2.

TABLE 2

Seeding density and mass of pDNA used for cytotoxicity experiments.

| Cell line | Seeding Density (cells/well) | pDNA (ng/well) |
|---|---|---|
| HEK293T | $1.65 \times 10^4$ | 84 |
| MCF-7 | $1.18 \times 10^4$ | 84 |
| HeLa | $1.35 \times 10^4$ | 84 |

Cells were allowed to settle for 24 h, the media was removed, cells were washed with PBS once, and Opti-MEM media containing transfection cocktails without serum were applied. After 4 h, media was replaced with complete media containing serum. Cells were left for a further 20 or 44 h, and CellTliter-Glo reagent (Promega, 10 µl per well) was added. Plates were shaken and incubated for times according to the manufacturer's protocol and then read on a luminescence plate reader (PericinElmer EnSpire series). Measured values were normalised to control wells, which were treated identically, but received Opti-MEM containing no transfection agents. All conditions were measured at least in triplicate. Additional controls (pDNA only, unwashed wells) were measured to confirm no toxicity of the plasmid alone, loss of viability owing to Opti-MEM treatment, or loss of cells due to washing.

Functional Outcome Transfection Study

MCF-7 cells were transfected with CRISPR/dCas9, TALEs and zinc fingers, using the transfection protocol above. The plasmids were delivered in mixtures as summarised in Table 3. Brightfield images were taken for all the conditions prior to RNA extraction. TALE plasmids incorporated an EGFP sequence and so were imaged with a fluorescent microscope as described previously. Messenger RNA (mRNA) was extracted using 1 ml Trizol reagent (Invitrogen) for approximately $1 \times 10^7$ cells, according to the manufacturers protocol. RNA levels were analysed by real time reverse transcriptase using the MultiScribe Reverse Transcriptase (Life Technologies) and TaqMan Universal PCR Master Mix (Life Technologies). Primers and probes used to detect Maspin and GAPDH mRNA level are a validated commercially available product (Life Technologies) and used according to the manufacturer's protocol. Differences in mRNA level variation among subgroups were analysed with Rotor Gene Q (QIAGEN).

TABLE 3

Plasmid constructs and mixture ratios used for transfection experiments.

| Construct 1 | Construct 2 | Mass Ratio (1:2) |
|---|---|---|
| CRISPR/dCas9-VP64 | pSP gRNA (mix of 4) | 2:1 |
| TALE-VP64_a | TALE-VP64_b | 1:1 |
| ZF26-VP64 | ZF38-VP64 | 1:1 |

Statistical Analysis

Statistical analyses were performed with Graphpad Prism (GraphPad Software Inc.) The data is illustrated as the average, error bars represent the standard deviation. For all tests, differences were considered significant at p<0.05 (*), p<0.01 (), p<0.001 (*), p<0.0001 (****). Unless otherwise specified, data are represented as the means of technical triplicate and biological duplicate independent experiments.

Synthesis of Dendronised Polymers
1. Copolymer Backbone Synthesis

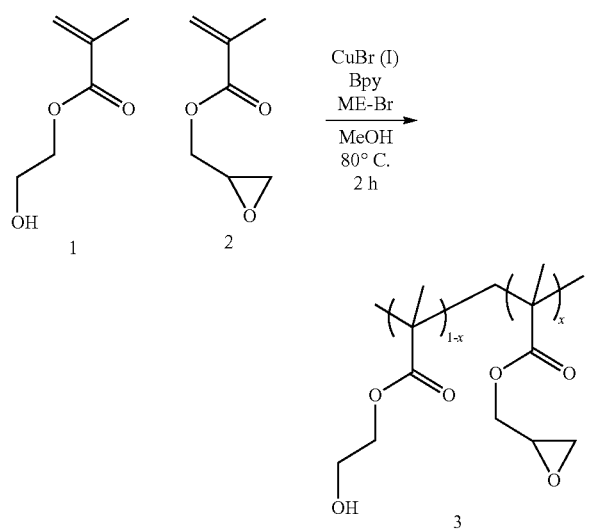

Statistical poly(HEMA-ran-GMA) were synthesised by ATRP of 1 and 2, adapted from reported methods (J. V. M. Weaver, I. B. Stimulus-Responsive Water-Soluble Polymers Based on 2-Hydroxyethyl Methacrylate. *Macromolecules* 37, (2004)). In a typical reaction, monomer inhibitors were removed using a basic alumina column. Monomers were dissolved in MeOH and degassed. Copper (I) bromide (0.70 mmol) was combined with 2,2'-bipyridine (2.5 mmol) and monomer solutions at various feed ratios (as detailed in Table 4, total monomer ~32 mmol). Morpholino)ethyl 2-bromoisobutyrate (ME-Br) (1 mmol) initiator was added and reaction was carried out at 80° C. in standard Schlenk conditions for 2 h. The product 3 was collected by repeated precipitation in diethyl ether and centrifuged; the solid product was dried overnight under vacuum.

Four different linear polymer backbones of poly[(2-hydroxyethyl methacrylate)-ran-(glycidyl methacrylate)] with varying GMA content (3a, x=0.03; 3b, x=0.08; 3c, x=0.17; and 3d, x=0.28) were prepared, as shown in FIG. 1. Copolymers were identified via $^1$H NMR (500 MHz, CD$_3$OD), where the appearance of peaks δH 2.70 (1H, br) and 2.87 (1H, br) correspond to the epoxide moiety, confirming presence of GMA. Molecular weight and PDI of polymers were measured using GPC (Table 5) (Adapted from M. Smallridge et aL "Stimulus-responsive water-soluble polymers based on 2-hydroxylethyl methacrylate".)

TABLE 4

Monomer feed ratios for ATRP reactions to produce poly(HEMA-ran-GMA) copolymers.

| Poly-mer | Feed ratios | | GMA mol % ($^1$H integration) |
|---|---|---|---|
| | GMA/MeOH | HEMA/MeOH | |
| 3a | 0.8 mL (1.5 mmol) | 15.2 mL (31.2 mmol) | 3 |
| 3b | 1.9 mL (3.6 mmol) | 14.1 mL (29.0 mol) | 9 |
| 3c | 4 mL (7.5 mmol) | 12 mL (24.7 mmol) | 16 |
| 3d | 6.4 mL (12 mmol) | 9.6 mL (19.7 mmol) | 28 |

TABLE 5

Copolymer molecular weight and PDI measurements from GPC.

| Polymer | Mw (kDa) | PDI |
|---|---|---|
| 3a | 13.6 | 1.25 |
| 3b | 15.7 | 1.21 |
| 3c | 21.5 | 1.30 |
| 3d | 17.5 | 1.30 |

2. Dendron Synthesis and Attachment

Dendrons of various generations were attached to the different copolymer backbones to produce a library of dendronised polymers (9a-10d) (FIG. 1).

Propargyl-poly(amido amine) dendron synthesis was adapted from published procedures (Lee, J. W. et al. Convergent Synthesis of Symmetrical and Unsymmetrical PAMAM Dendrimers. *Macromolecules* 39, 2418-2422 (2006)).

Azide functionalisation of poly(HEMA-ran-GMA) polymers was achieved by treating copolymer 3a with sodium azide and ammonium chloride in DMF. The reaction was allowed to proceed at 60° C. for 72 h. The solution was cooled, insoluble byproducts were removed by centrifugation, and the product 4a was purified by repetitive precipitation in ether and dried under vacuum. Other copolymers were treated the same way and reactions scaled accordingly.

PAMAM dendrons were attached to the azido-functionalised polymers by a copper-catalysed alkyne-azide click reaction, adapted from Zhao et al (Zhao, P. et al. Highly efficient synthesis of polymer brushes with PEO and PCL as side chains via click chemistry. *Polymer* 53, 1992-2000 (2012)). For reaction with 4a, 3.5 generation propargyl-PAMAM dendron (5) was dissolved in DMF before addition of 4a. Pentamethyldiethylene triamine was added and the solution was degassed. The reaction commenced at room temperature with the addition of copper (I) bromide and proceeded for 72 h. Product 7a was purified by dialysis against deionised water and collected via lyophilisation. Dendron generation was completed by reaction with ethylene diamine, before being purified by dialysis against deionised water and product 9a collected by lyophilisation.

3. Dendron Fluorination.

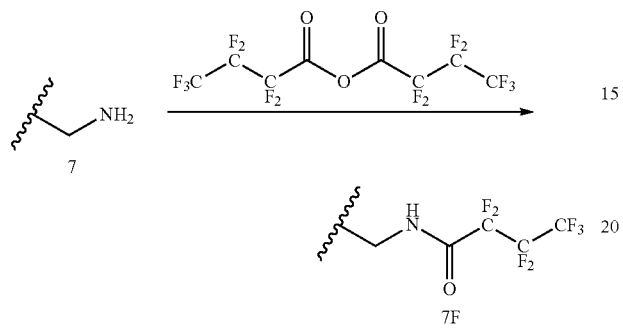

Fluorination of PAMAM dendrons was adapted from Wang et al (Wang, M., Liu, H., Li, L. & Cheng, Y. A fluorinated dendrimer achieves excellent gene transfection efficacy at extremely low nitrogen to phosphorus ratios. *Nat. Commu.* 5, 3053 (2014)). Fluorination of terminal PAMAM primary amines was achieved using heptafluorobutyric anhydride. Dendronised polymers 9a-10d were all treated to give fluorinated dendronised polymers 11a-12d using the same method.

Polyplex Characterisation

Polymer stock solutions were made to a final concentration of 10 mM primary amines in sterilised milli-Q water. For gel retardation assays, polymer solutions were mixed with pDNA (50 ng) at various N/P ratios and incubated at room temperature for 30 min. Samples were electrophoresed on 1% w/v agarose gels in sodium borate buffer (pH 9) and stained with ethidium bromide. For DLS and zeta potential measurements (Zetasizer Nano ZS, Malvern, UK), polymer solutions were incubated with pDNA (1 μg) at room temperature for 30 min. Solutions were diluted to 1 mL and measurements were taken in triplicate after equilibration for 2 min. The intensity-weighted zeta potential and hydrodynamic radius of polyplexes were measured; all zeta potential measurements were taken at pH=6.

Plasmid Binding

Gel retardation assays, and DLS and zeta potential measurements were used to determine optimal nitrogen-to-phosphorus (N/P) ratios for pDNA binding.

Gel retardation assays conducted with 5.3 kb sized pDNA plasmid demonstrated complete plasmid binding by N/P ratio of 1, 2 and 1.5 for a comparative G5 PAMAM dendrimer, 10c dendronised polymer and 12c dendronised polymer formulations, respectively.

DLS and Zeta polyplex optimisation for a comparative G5 poly(amido amine) (PAMAM) dendrimer and 10c polymer, using 5.3 kb EGFP plasmid. Binding was assessed in MilliQ water at pH≈6 without additional buffers. All plasmid is bound at N/P ratio of 1 in the case of the comparative PAMAM dendrimer, while the 10c polymer formulation only binds all pDNA at an N/P ratio of 2.

Cell Culture and Gene Transfection

HEK293T (human embryonic kidney cell line, ATCC) and HeLa (human cervical adenocarcinoma cell line) were cultured in Dulbecco's Modified Eagle's Medium (DMEM, Gibco) with 10% heat-inactivated Fetal Bovine Serum (FBS, Life Technologies). MCF-7 (human breast adenocarcinoma cell line, ATCC) were cultured in Minimum Essential Medium α (MEM α, Gibco) supplemented with 1% sodium bicarbonate, 10% FBS. Cell lines were seeded in 12-well plates (Corning Costar, Sigma Aldrich). Cell seeding densities are summarised in Table 6. No antibiotic/antimycotic was used.

TABLE 6

Seeding densities of cell lines used for transfected experiments.

| Cell line | Seeding Density (cells/well) |
|---|---|
| HEK293T | $2.0 \times 10^5$ |
| MCF-7 | $1.4 \times 10^5$ |
| HeLa | $1.8 \times 10^5$ |

For transfection, polymer solution and pDNA were diluted to the required concentration in Opti-MEM reduced serum media (Gibco). For cotransfection experiments, plasmid DNA was mixed at a 1:1 ratio based on mass. Polymer and DNA solutions were mixed so as to achieve the optimal N/P ratio for 1 μg DNA in total volume of 130 μL, and incubated at room temperature for 30 min. Commercial transfection agent Lipofectamine 2000 (Invitrogen) was used as a standard according to the manufacturer's protocol. 130 μL of polyplex solution was transferred to the appropriate well containing 300 μL of Opti-MEM. After a 4 h incubation period, an additional 570 μL of the appropriate complete culture medium was added and experiment was incubated for a further 44 h, giving a total transfection time of 48 h.

Transfection efficiency was observed using fluorescent microscopy and quantified via flow cytometry. Fluorescent and phase contrast images were taken using an Olympus IX-71 inverted microscope (U-MGFPHQ and U-MRFPHQ filters). Flow cytometry of EGFP transfections were conducted using BD FACSCantoII flow cytometer, cotransfection experiments were analysed using LSRII Fortessa flow cytometer. In preparation for flow cytometry cells were washed twice with phosphate buffered saline (PBS) and harvested with trypsin (Life Technologies). Cells were collected via centrifugation (300 g, 5 min) and washed in 500 μL FACS buffer (2% FBS, 4 mM EDTA in PBS). Cells were centrifuged again (300 g, 5 min) and resuspended in 200 μL of FACS buffer for flow analysis. Samples were acquired using BD FACS Diva software. EGFP was excited by 488 nm laser, and emission was measured with 502 nm long pass and 530/30 nm band pass filters; RFP was excited by 561 nm laser, and emission was measured with 600 nm long pass and 610/20 nm band pass filters. 30,000 single cell events, gated on forward scatter area vs height, were recorded for analysis. Post-acquisition analysis was performed on FlowJo vX software.

Figure 2:
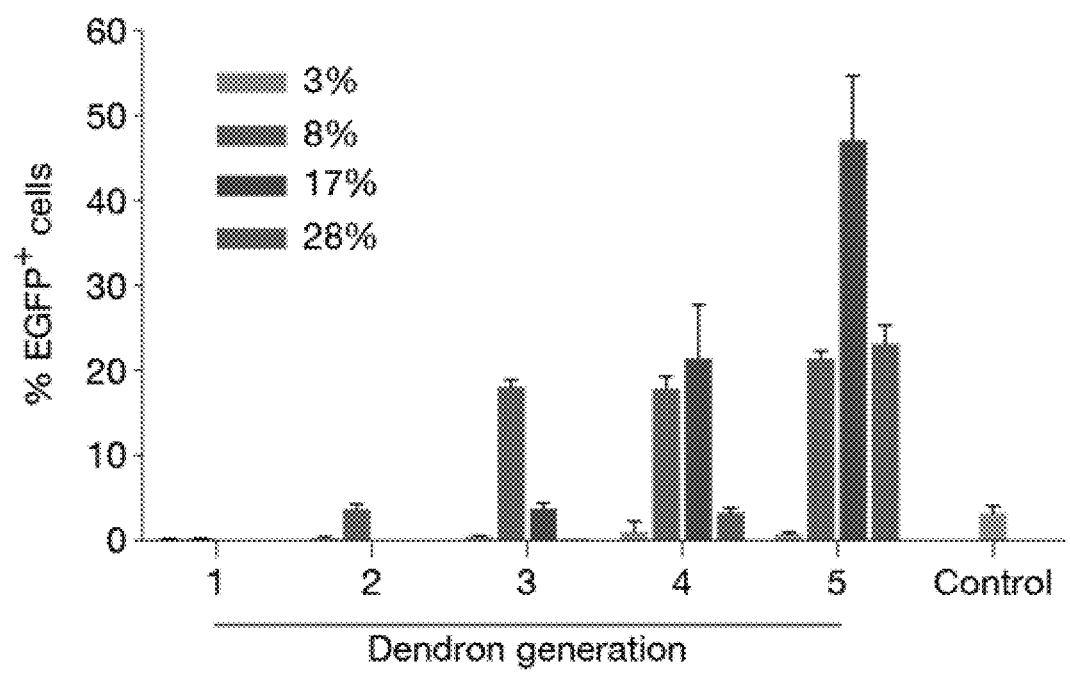
FIG. 2 is a graph illustrating the transfection efficiency of dendronised polymers of embodiments of the invention in delivering EGFP-encoding plasmid to MCF-7 cells at an N/P ratio of 10, compared to a traditional PAMAM G5 dendrimer ('control') also at N/P ratio of 10.

The ability of the dendronised polymers to transfect a small EGFP-encoding pDNA (5.3 kb) was first evaluated in the MCF-7 human breast adenocarcinoma cell line, which is regarded as difficult to transfect, against G5 PAMAM dendrimers as a control. The transfection efficiency was evaluated for all polyplexes at an optimised N/P ratio of 10 using fluorescent microscopy and quantified via flow cytometry. The results are shown in FIG. 2. The dendronised polymer architecture with G4 and G5 PAMAM dendrons demonstrated superior transfection compared to traditional G5 PAMAM dendrimers.

The study revealed strong relationships between transfection efficiency and dendron generation (G5 dendronised polymers 10a-d showed the highest transfection efficiencies) and between transfection efficiency and dendron density on the backbone (10c outperformed 10a, 10b, and 10d). To explain the observed drop in transfection efficiency between polymers 9c and 9d, and between 10c and 10d, we hypothesise that steric repulsion of highly substituted backbones limits the flexibility of the backbone, potentially interfering with electrostatic pDNA complexation. That is, when the distance between the dendrons is short, corresponding to a high degree of substitution, steric repulsion between dendrons limits the conformational flexibility of the system.

Cytotoxicity

Cells were seeded and transfected in poly(L-lysine)-coated 96-well plates under conditions and at densities proportional to those above ('General transfection protocol'), being adjusted for well growth area. After 48 h transfection, CellTliter-Glo® 2.0 (Promega) assay was used to quantify cell viability, in accordance with the manufacturer's instructions, except that only 10 µl reagent was added to each well. This was confirmed to still give a linear response with cell number (data not shown). Luminescence was recorded (PerkinElmer EnSpire) using 0.05 s measurement time averaged over 12 points per well and normalised to untreated controls.

Cells transfected with 5.3 kb EGFP plasmid using 10c polymer formulation at various N/P ratios (N/P ratios of 5, 7.5, 10 and 15) were assessed for cell viability at 24 and 48 h. Culture conditions were identical to those used in the transfection experiments. There was no significant difference ($p>0.05$) observed in cell viability up to the highest concentration tested (N/P 15).

Effect of Fluorination: Delivery of Large pDNA

Having established that G5-dendron-substituted polymers 10a-d performed better than conventional G5 PAMAM dendrimers and resulted in no detectable cytotoxicity we investigated the effect of fluorination on the transfection efficiency of G5-dendron substituted polymers.

MCF-7 cell line was transfected with 5.3 kb EGFP plasmid using 12c polymer various N/P ratios (N/P ratios of 2.5, 5, 7.5 and 10) and cell viability was assessed at 24 and 48 h. Culture conditions were identical to those used in the transfection experiments. There was no significant difference ($p>0.05$) observed in cell viability up to the highest concentration tested (N/P 10).

Cell Transfection

We compared the ability of unfluorinated (10a-d) and fluorinated (12a-d) G5 polymers to transfect EGFP-encoding pDNA (5.3 kb) in MCF-7 cells against Lipofectamine 2000 as a control. Optimal N/P ratios were again determined by gel retardation assays and DLS and zeta potential measurements and screened at three different N/P ratios. Lipofectamine 2000 was used as a positive control as it is one of the most widely used, commercially-available reagents with consistently high transfection efficiencies. Fluorination enhanced the transfection ability of G5 dendronised polymers for all polymer backbones, and polymer 12c displayed transfection efficiencies similar to Lipofectamine 2000.

Figure 3:
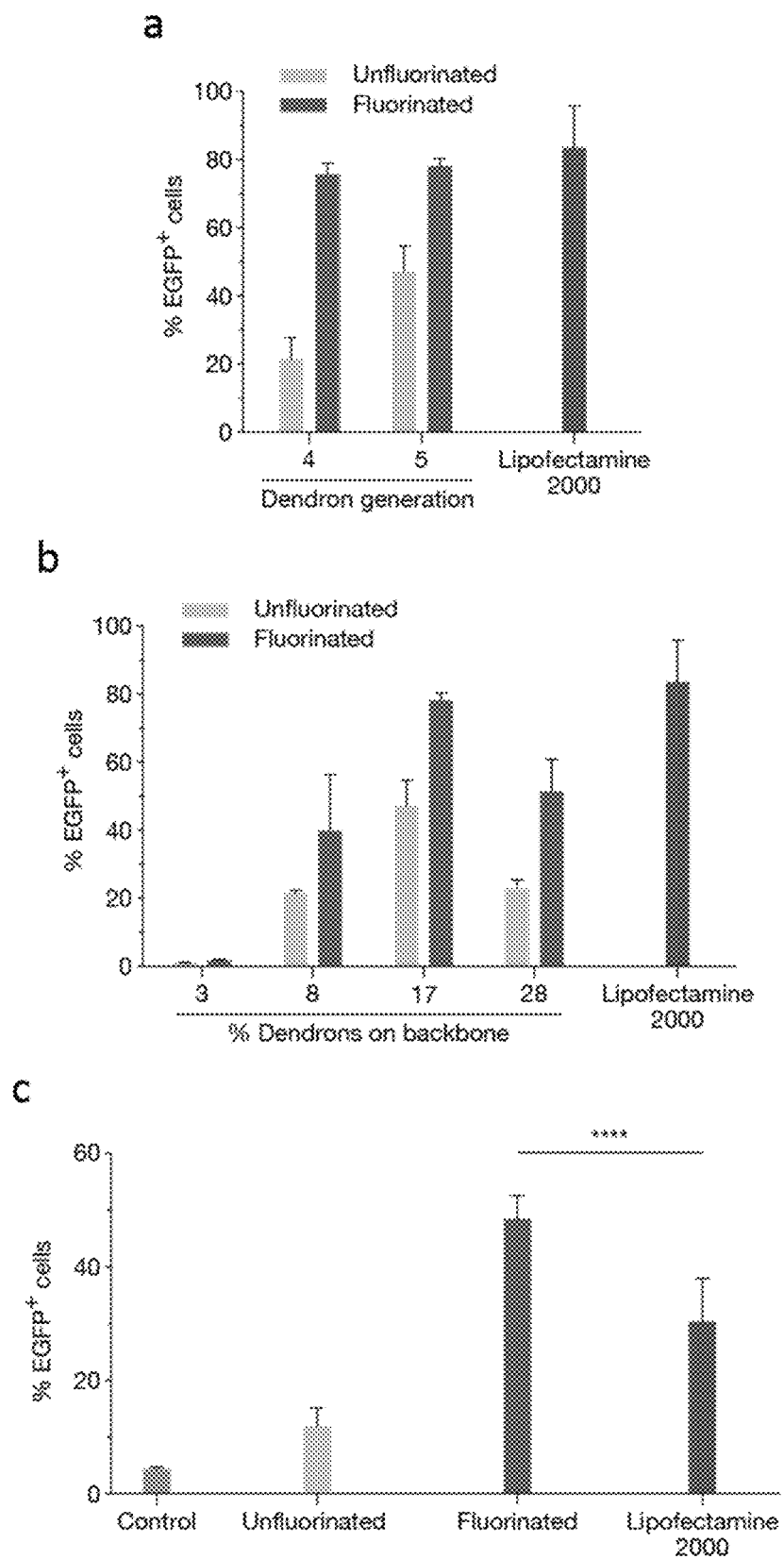
FIG. 3 shows graphs demonstrating that fluorinated dendronised polymers increased EGFP-encoding pDNA transfection efficiency significantly (a, p≤0.0001; b, p≤0.001) and fluorinated dendronised polymers of embodiments of the invention achieved transfection efficiencies similar to Lipofectamine 2000 (p>0.05), where the figure shows: in (a) G4 and G5 PAMAM dendronised polymers are compared, in (b) G5 PAMAM dendronised polymers are compared, and in (c) a fluorinated dendronised polymer of the invention was able to achieve significantly higher transfection efficiency than Lipofectamine 2000 (p≤0.0001) when MCF-7 cells were transfected with a large EGFP-expressing plasmid (10 kb).

We next evaluated delivery of a larger EGFP-encoding pDNA (10 kb). The fluorinated dendronised polymer 12c outperformed both control (5 PAMAM dendrimers and Lipofectamine 2000 for delivery of large pDNA (FIG. 3).

Delivery of Multiple Plasmids

We evaluated the ability of 12c (17%, 5G fluorinated) polymer to perform cotransfections in HEK293T human embryonic kidney, HeLa human cervical cell carcinoma, and MCF-7 cell lines with pDNAs of similar size, encoding EGFP (5.3 kb) and mCherry (5.3 kb), as well as with pDNAs of different size, encoding EGFP (10 kb) and mCherry (5.3 kb). HEK293T and HeLa cell lines were chosen as they are widely used model cell lines. Cotransfection efficiency was measured using flow cytometry. Additionally we confirmed the absence of cytotoxicity of the polymer in HEK293T and HeLa cell lines.

Figure 4:
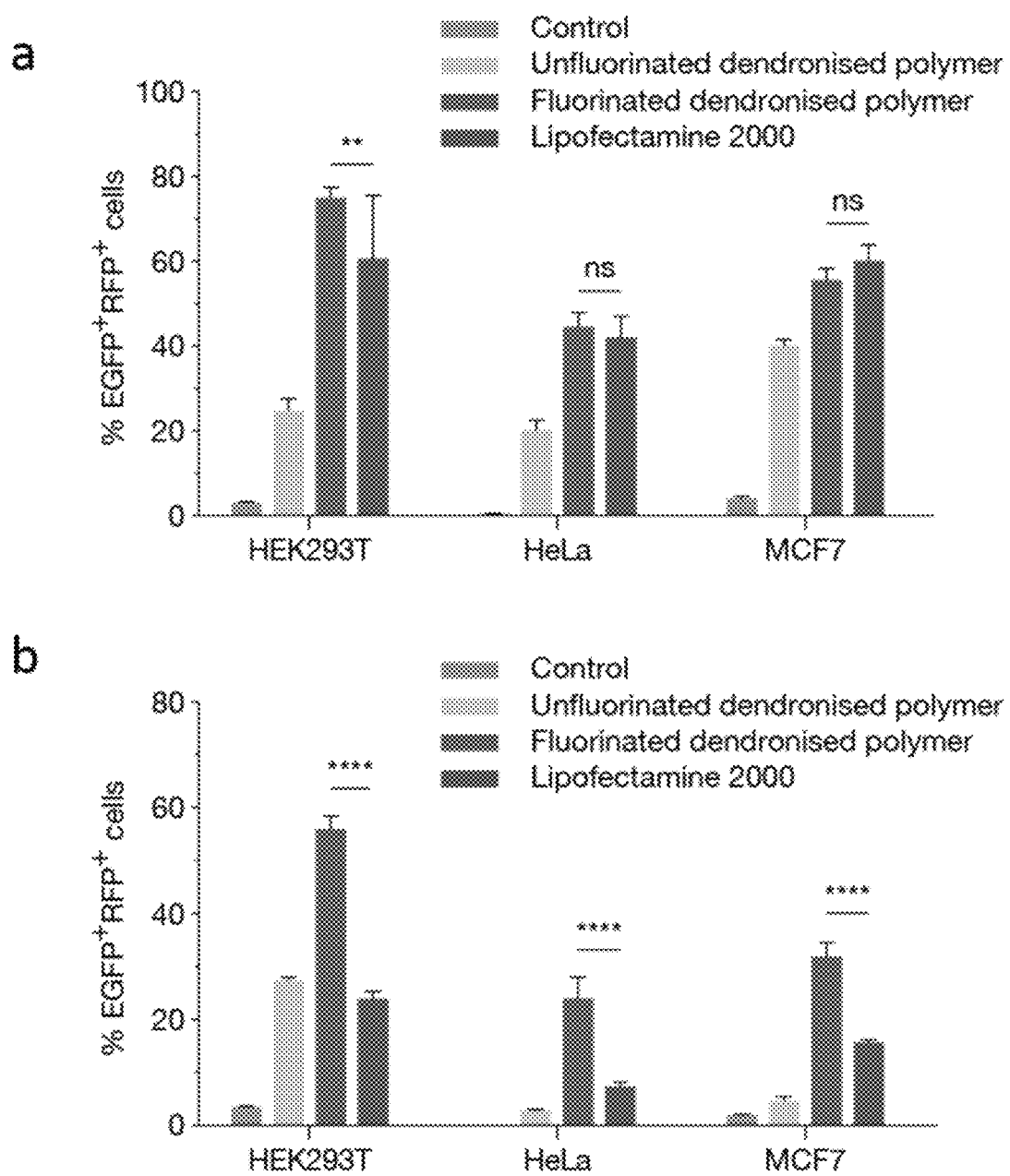
FIG. 4 shows graphs illustrating the results of cotransfection experiments in HEK293T, HeLa and MCF-7 cell lines, where the figure shows: (a) cell lines were cotransfected with two pDNAs of equal size encoding EGFP and mCherry (RFP$^+$) (both 5.3 kb), and (b) cell lines were cotransfected with plasmids of different size encoding EGFP (10 kb) and mCherry (5.3 kb).

The fluorinated dendronised polymer 12c formulation demonstrated significantly higher cotransfection levels of multiple-sized plasmids compared to Lipofectamine 2000 across all cell lines ($p \leq 0.0001$) (FIG. 4). This further consolidated the theory that while conventional liposomal transfection agents are capable of delivering pDNA of lower sizes, they are limited in their packaging capacity for delivering large expression cassettes. The dendronised polymers of the invention can overcome these limitations.

Delivery of Genome Editing Tools

Figure 5:
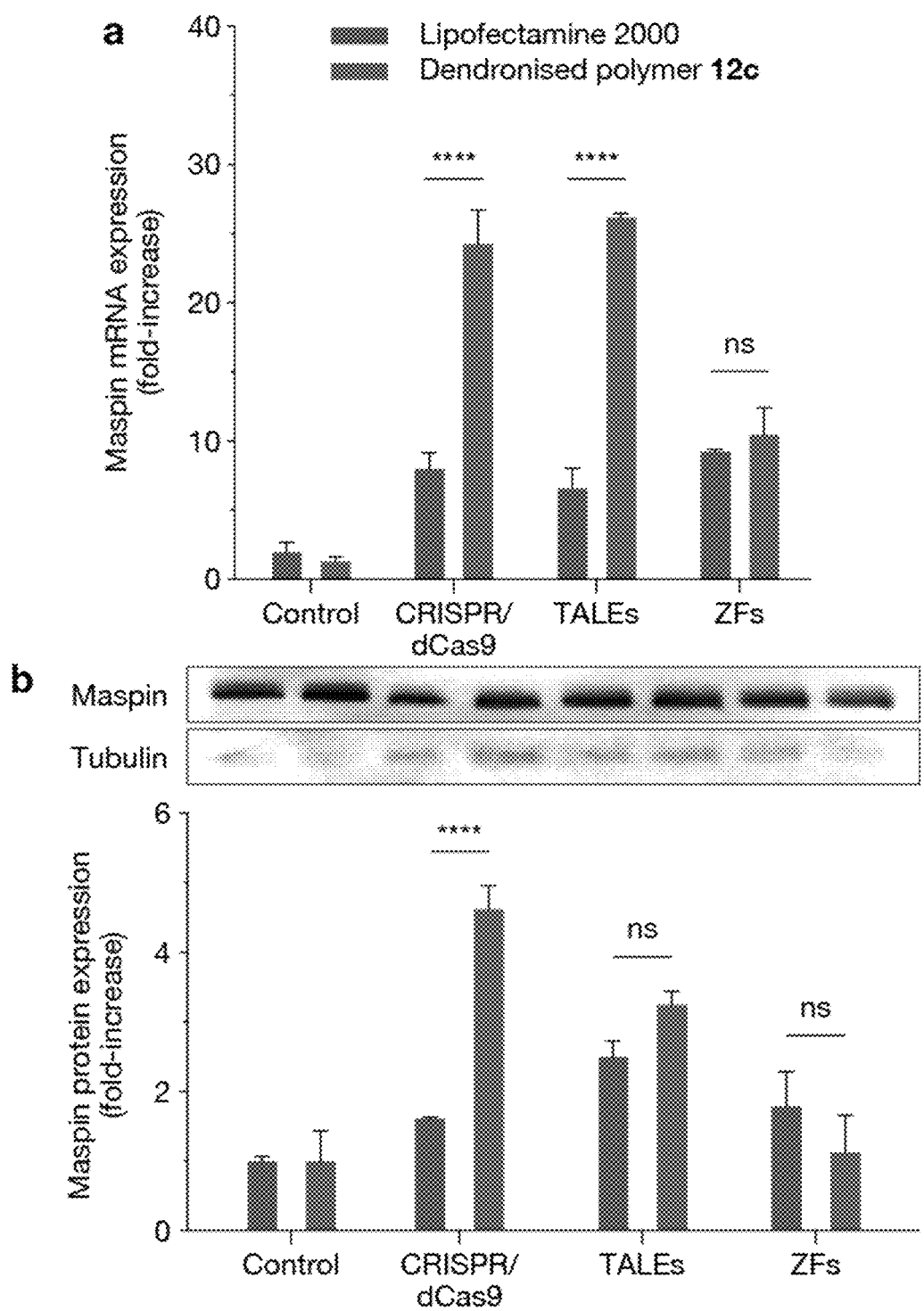
FIG. 5 shows graphs illustrating the results of transfection of MCF-7 cells with CRISPR/dCas9, TALEs and ZFs with VP64 for the activation of maspin, where a dendronised polymer of an embodiment of the invention achieved significantly increased maspin upregulation at both the mRNA (a) and protein (b) level compared to Lipofectamine 2000 when delivering the CRISPR/dCas9 and TALE platforms (**** p≤0.0001). Cells were transfected with an empty plasmid as a control.

The ability of the dendronised polymers to achieve a functional outcome by delivering three different genome engineering tools: CRISPR/dCas9-VP64 (9.8 and 3.2 kb), TALE-VP64 (9.3 kb) and ZF-VP64 (6.1 kb) for transcriptional activation of maspin (mammary serine protease inhibitor, SERPINB5) in the MCF-7 cell line was also investigated. Maspin was chosen as a model target in the present study as it is has been reported as an important tumour suppressor gene. Loss of maspin expression is associated with increased invasive potential and metastasis. The transcriptional activation of maspin using each of the aforementioned technologies were compared using the fluorinated dendronised polymer 12 against Lipofectamine 2000 as control. Significant activation was achieved for CRISPR/dCas9-VP64 and TALE-VP64 controls at both the mRNA ($p \leq 0.0001$) and protein ($p \leq 0.05$) levels. The results are shown in FIG. 5.

Our data shows that Lipofectamine 2000 can deliver small (~5 kb) pDNA well, but fails to deliver large (~10 kb) pDNA with similar efficiency. However, using our dendronised polymers, we achieved successful transfection of large pDNA. We observed that co-expression of plasmids in hard-to-transfect cells was higher when plasmids were mixed and co-delivered, in comparison to complexing and delivering the plasmids separately. Plasmids can be successfully delivered separately only when high transfection efficiency (~100%) is achievable. However, for less ideal systems in which the transfection efficiency is lower, we find that it is beneficial to mix gene editing tools with one vector, such as our polymer.

This reasoning is reflected in the results of our functional study where we demonstrated the delivery of ZF-VP64, TALE-VP64 and CRISPR/dCas9-VP64. Among the three major genome editing technologies, the sequence encoding the ZF proteins is relatively short and is therefore not likely to be limited by vector capacities. However, the greatest limitation of ZFs is their limited targeting density, and consequent off-target effects due to a short recognition motif, and the limited number of sites that they can effectively and selectively target. These limitations are overcome using the more flexible TALE and CRISPR/Cas9 technologies, but the increased size of these tools and the requirement for concurrent delivery of multiple components make their introduction into cells a greater challenge, and is currently a bottleneck in the development of gene therapies.

We used large plasmids and multiple plasmids encoding fluorescent proteins to model and address this issue, and demonstrated significantly improved efficiencies using our fluorinated dendronised polymer 12c, as compared to Lipofectamine 2000. Delivery of TALE-VP64 and CRISPR/dCas9-VP64 designed to upregulate tumour suppressor maspin, further validated these findings. Using our polymer design, we achieved significant upregulation of maspin at the mRNA and protein levels.

Example 2

Activation of Mammary Serine Protease Inhibitor (MASPIN, SERPINB5) and Cysteine-Rich 61/Connective Tissue Growth Factor/Nephroblastoma-Overexpressed 6 (CCN6, WISP3).

We became interested in whether a synthetic dendronised polymeric system delivering CRISPR/dCas9 fused with VP64 activator could be used to activate tumour suppressor genes to result in a functional change in cell fate. We were also interested in designing a dendronised polymeric system for targeted in vivo delivery.

Due to the versatility and simplicity of the CRISPR/dCas9 system, activation of two tumour suppressor genes were targeted—Mammary Serine Protease Inhibitor (MASPIN, SERPINB5) and Cysteine-rich 61/Connective tissue growth factor/Nephroblastoma-overexpressed 6 (CCN6, WISP3).

Materials and Methods
Dendronised Polymer Preparation

A non-toxic polymeric formulation composed of a linear random copolymer backbone of a hydroxyethyl methacrylate (HEMA, 1) and glycidyl methacrylate (GMA, 2), with polyamido amine (PAMAM) fifth-generation dendrons attached along the backbone via a copper-catalyzed click reaction was prepared in accordance with the following procedure:

Copolymer Backbone

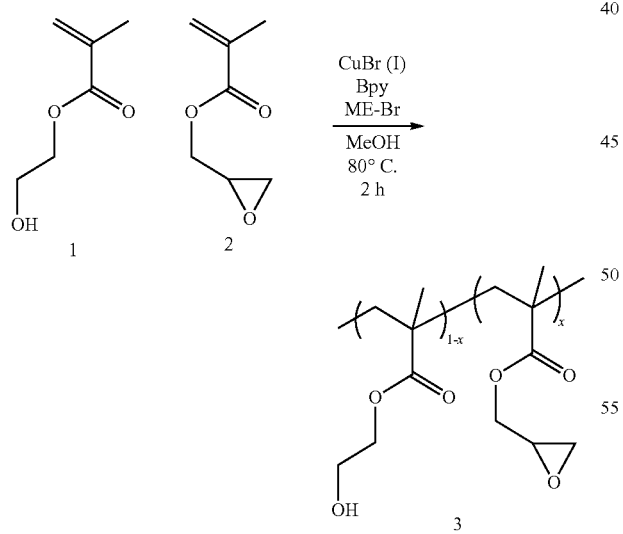

P(HEMA$_{0.84}$-ran-GMA$_{0.16}$) copolymer was synthesized using methodology adapted from Weaver et al. (J. V. M. Weaver, I. B. Stimulus-Responsive Water-Soluble Polymers Based on 2-Hydroxyethyl Methacrylate. *Macromolecules* 37, (2004)). Briefly, inhibitors for hydroxyethyl methacrylate (HEMA, 1, 7.5 mmol) and glycidyl methacrylate (GMA, 2, 24.7 mmol) were removed via passage through a plug of basic alumina and reacted using an atom-transfer radical polymerization method to afford copolymer 3. Copolymer composition was determined by $^1$H NMR (500 MHz, CD$_3$OD), where integration of peaks δH 2.70 (1H, br) and 2.87 (1H, br) corresponding to the epoxide moiety was used to determine copolymer consists of 16.3 mol % GMA 2. Polymer molecular weight (21.5 kDa) and PDI (1.30) of the polymer measured using GPC.

Click Reaction

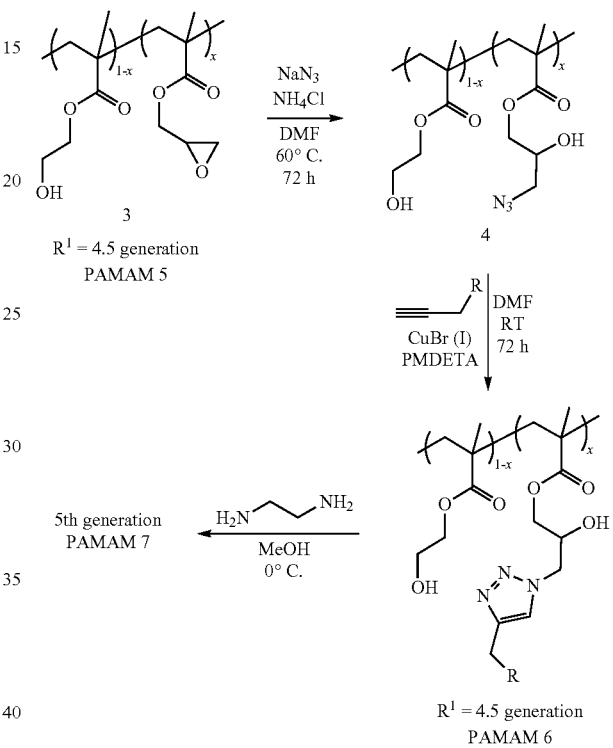

Azido functionalization: Copolymer 3 was functionalized with azido groups as described previously above in Example 1, to afford product 4.

Propargyl dendron synthesis: 4.5 generation (G4.5) propargyl PAMAM dendron 5 was synthesized as described above in Example 1.

Click reaction: Propargyl poly(amido amine) dendrons were attached via an azide-alkyne click reaction to afford product 6 and generation finalized to G5 by reaction with ethylene diamine, resulting in final product 7 as previously described above in Example 1.

Fluorination

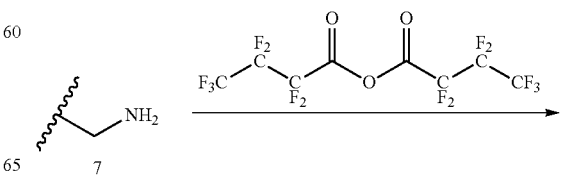

-continued

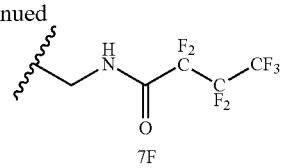

Polymer 7 (104 mg) was fluorinated by reaction with heptafluorobutyric anhydride (91.3 μL, 0.37 mmol), resulting in fluorinated polymer 7F, as per protocol described above in Example 1.

Functionalised Dendronised Polymer

Dendronised polymer formulations were modified by the attachment of polyethylene glycol (PEG) and either Cyanine-7 (Cy7) fluorescent dye (non-targeted), or cyclic RGD peptide with Cy7 attached (cRDG-Cy7, targeted) using the protocols described below.

Non-Targeted Dendronised Polymer Formulation

Polymer (7F 10.2 mg, 19.6 μmol primary amines) was dissolved in 0.5 mL PBS, and SM(PEG)$_{12}$ 10 DMSO solution (2.5 μL) was added to result in product 11. pH was adjusted to 7 and reaction was left to proceed at r.t. for 2 h. Separately, Cy7-NHS (8, 0.55 mg, 0.81 μmol) was dissolved in 50 μL of DMSO, and added to cysteamine solution in PBS (phosphate buffered saline solution, 62.2 μL, 1 mg/mL, $8.06 \times 10^{-7}$ mol). 200 uL of extra PBS was added and pH adjusted to 8. Reaction was left to proceed at r.t. for 2 h to give product 9. Then reaction mixtures were combined and left to react at pH 7 and r.t. overnight. Product 12 was purified by dialysis (membrane MW cutoff 12-14 kDa) in PBS followed by deionized water, and collected by lyophilization. Reaction was confirmed by spectral characterization (Varian Cary Eclipse fluorescence spectrophotometer).

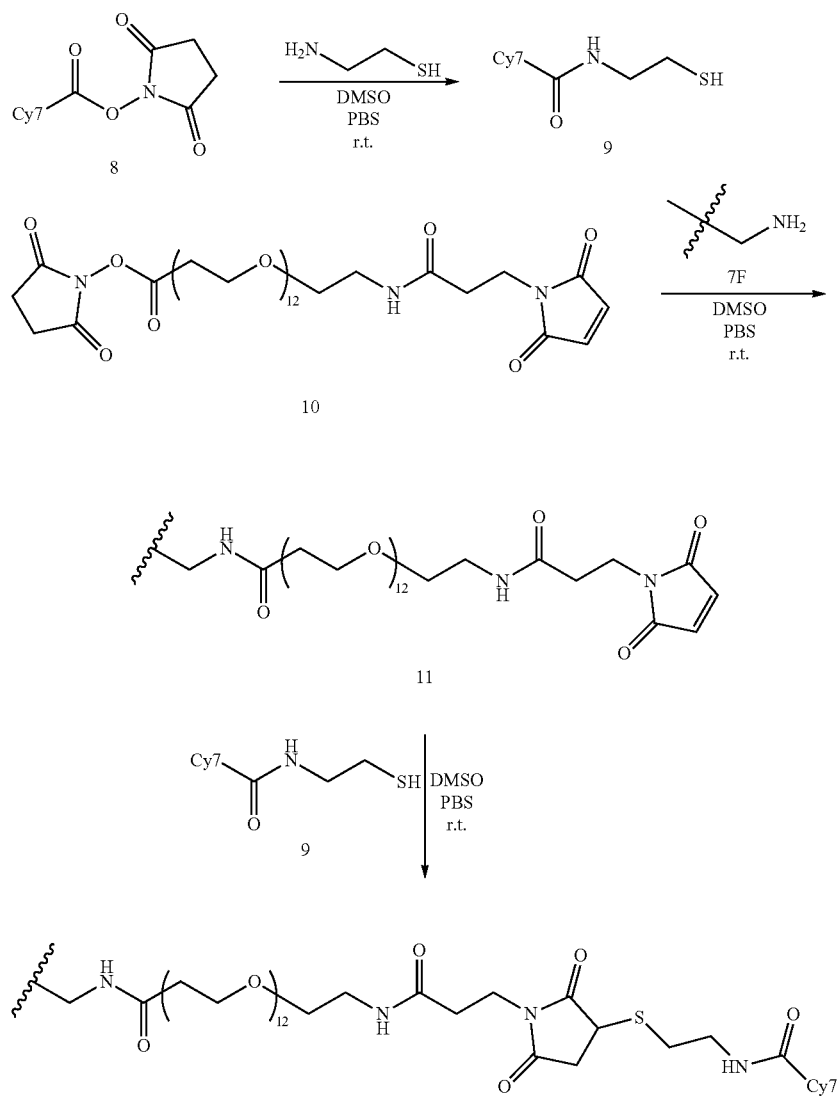

Targeted Dendronised Polymer Formulation

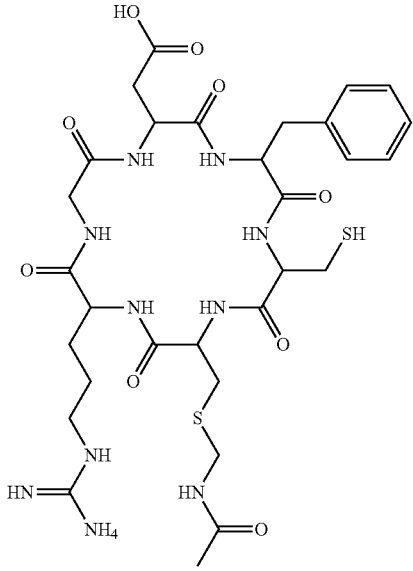

13

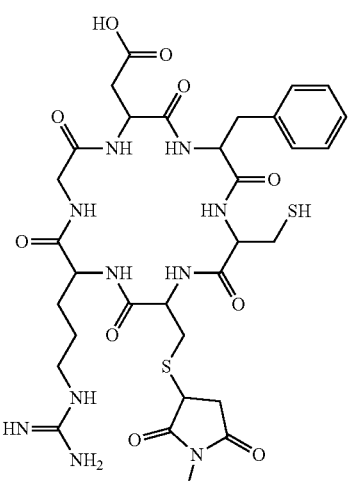

14

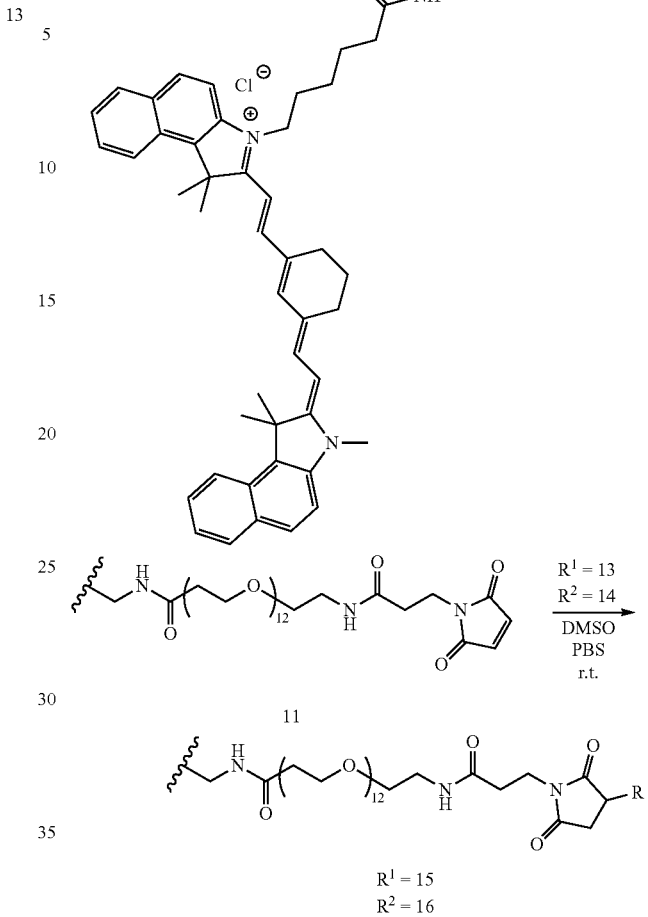

Polymer (7F, 8.7 mg, 16.7 μmol primary amines) was dissolved in 400 uL of PBS and reacted with SM(PEG)$_{12}$ 10 DMSO solution (2.19 μL) at r.t. for 2 h at pH 7 to give product 11. Peptide H-DfC(1230)RG-cyclic 14 (1.0 mg, 0.67 μmol) was dissolved in 300 μL of PBS and added to the stirring reaction mixture. Reaction was left to proceed overnight at r.t., pH 7, and product purified by dialysis (membrane MW cutoff 12-14 kDa) in PBS followed by deionized water, and collected by lyophilization. Product 16 was confirmed by spectral characterization. Formulation without Cy7 (product 15) was prepared by same protocol and reaction was confirmed by NMR.

General protocols used this study are described below:
DIS and Zeta

Polymer solutions were mixed with pDNA at appropriate N/P ratios and incubated at room temperature for 30 min in PBS. Size and zeta potential of the resulting polyplexes were characterized using dynamic light scattering (Zetasizer NanoZS), using a 4 mW He—Ne laser operating at 633 nm with a scattering angle of 173°. Measurements were taken in triplicate after an initial equilibration period of 2 min. For calibration of the measurements 'material' was defined as PGMA (refractive index of 1.515 and absorbance of 0.05) and 'dispersant' was defined as water at 25° C. (refractive index of 1.330 and viscosity of 0.887). The intensity-weighted zeta potential and hydrodynamic radius of the polyplexes is presented as mean ± standard deviation. All zeta potential measurements were taken at pH=7.4.

CRISPR Design and Preparation

All dCas9 constructs used an inactivated form of S. pyogenes Cas9 protein with two mutations in D10A and H840A. pcDNA-dCas9-No effector (Addgene plasmid #47106) was a gift from Charles Gersbach. pcDNA-dCas9-VPR with VP64, p65 and Rta fused to its C-terminus (Addgene plasmid #63798) was a gift from George Church. MS2-P65-HSF1_GFP (Addgene plasmid #61423), expressing the SAM helper complex with a 2A GFP, was a gift from Feng Zhang. The Benchling CRISPR design tool was used to select sgRNA target sequences in the MASPIN and CCN6 proximal promoters. Annealed oligonucleotides (Integrated DNA Technologies, Singapore) containing the sgRNA target sequences were cloned into BbsI sites in the sgRNA(MS2) cloning backbone (Plasmid #61424), which was a gift from Feng Zhang. Plasmids were prepared using the QIAGEN Plasmid Maxi Kit (QIAGEN).

In Vitro Experiments
Cell Culture (MCF-7, MCF-7-luci, H157)

MCF-7 and MCF-7 luciferase (human breast adenocarcinoma cell line, ATCC, and MCF-7 modified in-house to express luciferase) were cultured in Minimum Essential Medium α (MEM α, Gibco) supplemented with 1% sodium bicarbonate (is this right? We add 2% by volume, i.e., 1 ml in 50 ml, and stock concentration is 7.5%), 10% PBS and 1× GlutaMAX. H157 (human lung adenocarcinoma cell, ATCC) were cultured in RPMI1640 supplemented with 10% PBS and 1× GlutaMAX. All cell lines were grown in a humidified incubator at 37° C. with 5% $CO_2$. Cell lines were seeded in 12-well plates (Corning Costar, Sigma Aldrich) in media without antibiotic/antimycotic for in vitro experiments. Cell seeding densities are summarized in Table 7.

TABLE 7

Seeding densities for transfection experiments in a 12-well standard culture plate

| Cell line | Seeding density (cells/mL) |
| --- | --- |
| MCF-7 | $1.8 \times 10^5$ |
| H157 | $1.0 \times 10^5$ |

Transfection

Transfections were performed as described above. Briefly, polymer solution and pDNA were diluted to the required concentration in Opti-MEM reduced serum media (Gibco). For a 12-well standard plate format, polymer solution was prepared as 5 mM primary amines in filtered sterilised Milli-Q water, and 2.4 µL of polymer solution was diluted to a total 70 µL in Opti-MEM. 1 µg of pDNA (in 70 µL of Opti-MEM) was then mixed thoroughly with the polymer preparation, and then incubated for 30 min at r.t. 130 µL of the polyplex solution was then transferred to the appropriate well, which had been washed twice with phosphate buffered saline solution (PBS) and 300 µL of Opti-MEM added. After a 4 h incubation period, an additional 570 µL of the appropriate complete culture medium was added and the experiment incubated for a further 44-68 h, giving a total transfection time of either 48 h or 72 h, respectively.

RNA Extraction and PCR
In Vitro Experiments

Total RNA was extracted using 1 ml Trizol reagent (Invitrogen) for approximately $1 \times 10^7$ cells, according to the manufacturer's protocol. Extracted total RNA was converted to cDNA using the High Capacity cDNA Reverse Transcription Kit (4368813, Applied Biosystems). The expression levels of the gene of interest were analysed with real-time reverse transcription quantitative PCR (RT-qPCR) with GAPDH as housekeeping control. RT-qPCR was carried out using TaqMan Fast Universal PCR Master Mix (4352042, Applied Biosystems). Primer-probe sets sequences used to detect mRNA levels were commercially purchased as detailed in Table 8.

TABLE 8

Primer-probe set information for mRNA analysis.

| Target | Catalogue number | Supplier |
| --- | --- | --- |
| GAPDH | 4332649 | Applied Biosystems |
| MASPIN | Hs Hs00985285_m1 | Thermo Fisher |
| CCN6 | Hs00180236_m1 | Thermo Fisher |
| E-Cadherin | Hs01023895_m1 | Thermo Fisher |
| N-Cadherin | Hs00983056_m1 | Thermo Fisher |
| ZEB1 | Hs01566408_m1 | Thermo Fisher |
| ZEB2 | Hs00207691_m1 | Thermo Fisher |
| FN1 | Hs01549976_m1 | Thermo Fisher |
| SNAIL1 | Hs00195591_m1 | Thermo Fisher |
| SLUG | Hs00161904_m1 | Thermo Fisher |
| TWIST1 | Hs01675818_s1 | Thermo Fisher |
| TWIST2 | Hs02379973_s1 | Thermo Fisher |
| LMX1A | Hs00898455_m1, cat # 4331182 | Thermo Fisher |
| CFAP52 | Hs00376807_m1, cat # 4331182 | Thermo Fisher |
| CDC123 | Hs00990152_m1, cat # 4351372 | Thermo Fisher |
| NXNL2 | Hs00708156_s1, cat # 4331182 | Thermo Fisher |

Analysis was performed in the ViiA 7 Real-Time PCR System (Applied Biosystems) and analyzed using QuantStudio Real Time PCR Software (v1.1, Applied Biosystems). Data were analyzed according to MIQE guidelines and results are expressed as fold change compared to dCas9 No Effector transfected cells after normalization against GAPDH mRNA levels.

Cell Viability Assay

Cell viability assay was carried out in 96-well flat-bottom tissue culture plates at a seeding density of $2.5 \times 10^4$ cells/well and was added to each well. Plates were incubated at 37° C. in a 5% $CO_2$ atmosphere for 48-120 h and were quantified with CellTiter-Glo reagent (Promega) according to the manufacturer's protocol, except that only 10 µl reagent was added to each well. This has been previously confirmed to still give a linear response with cell density. Luminescence was measured using EnVision 2102 Multilabel reader (PerkinElmer).

Migration Assay

Comparative migration assay was performed as per manufacturer's protocol (CytoSelect Migration Assay, 8 µm, colorimetric format, Cell Biolabs, Inc.). Briefly, cells were transfected 48 h prior to being collected and resuspended in serum free media for counting and seeding. Cells were seeded at $0.75 \times 10^6$ cells (in 500 µL) in upper chamber without serum. Full growth media was added below the chamber to encourage cell migration through the polycarbonate membrane. After 24 h cells were stained as per protocol, lysed, and the lysate absorbance quantified using EnVision 2102 Multilabel reader (PerkinElmer).

Soft Agar Assay

For soft agar assay, cells were transfected for 48 h, then harvested and counted. 5000 cells per well were seeded on a 6 well plate with growth medium, plated on top of a solidified layer of 0.5% agarose in growth medium and below a 0.35% agarose in growth medium and fed every 3 days with growth medium. After 3 weeks, the colonies were imaged by digital camera (Olympus). Conditions were analyzed in triplicate, with 6 fields of view marked at day 1 and imaged at 3 weeks for growth assessment. ImageJ software was used to assess the number and diameters of colonies.

BALB/c Nude Mice In Vivo Experiment

Ethics Statement

All experiments were conducted in accordance with the Code of Practice for the Care and Use of Animals and were approved by the University of Western Australia Animal Ethics Committee (RA/3/100/1336).

Tumour Inoculation and Maintenance

MCF-7 cells were stably transfected using [virus] and sorted by flow cytometry, transfection was confirmed using bioluminescence. MCF-7-luciferase (MCF-7-luci) cells were cultured routinely as described above. For tumour inoculation, cells were collected and resuspended in 50:50 mixture of MEM α and Matrigel (Corning BD Bioscience 354248), with 1 μg estrogen (β-Estradiol 17-valerate, Sigma Aldrich E1631). Animals were injected in right flank with cell suspension ($5 \times 10^6$ cells/animal, 60 μL). Tumours were maintained by subcutaneous injections of estrogen (20 μL, 50 ng/μL in peanut oil) located near the periphery of the visible tumour every 48 h.

Biodistribution Experiment (Inj, In Vivo and Ex Vivo Imaging, Confocal)

Tumours were inoculated and maintained as above. 7 days after tumour inoculation mice were randomly divided into two groups (N=7 per group) and injected by a single intravenous injection containing either the targeted 16 or non-targeted polymer 12 formulation and mCherry plasmid (10 μg plasmid/injection, N/P=10 for each polymer formulation). Animals (N=3 per group) were anesthetized (isoflurane) and imaged using CRi Maestro 2 (wavelengths, conditions) at 24, 48 and 72 h timepoints, and culled at 72 h for ex vivo imaging of tissue. Additional animals (N=2 per group, per timepoint) were culled at 24 and 48 h timepoints for ex vivo tissue imaging.

Tissue for sectioning: Tissues were washed in PBS, snap frozen in OCT (Sakura Tissue-Tek) and stored at −80° C. prior to being sectioned at 8 μm thickness using a Leica cryostat. Samples were stained for mCherry as per the protocol below (sectioning and staining), with the additional steps of initial fixation in 2% paraformaldehyde (PFA) in PBS for 10 min, and hydration with mqH$_2$O for 5 min.

Flow cytometry: Flow cytometry was conducted using BD FACSCantoII flow cytometer and samples were acquired using BD FACS Diva software. 100,000 single cell events, gated on forward scatter area vs height were recorded for analysis. Viable cells (calcein-AM stained) were gated for using a 488 nm laser and emission measured using 505 nm long pass and 530/30 nm band pass filters; mCherry was excited by a 561 nm laser, and emission was measured with 595 nm long pass and 610/20 nm band pass filters; Cy7 was excited by a 640 nm laser and emission was collected with 750 nm long pass and 780/60 nm band pass filters. Cultured MCF-7 cells were used as positive controls for calcein-AM, mCherry and Cy7, and non-fluorescent tissue was used as a negative control.

Intravenous Experiment (Inj, Imaging)

MCF-7-luci tumours were inoculated and maintained as described previously. Intravenous injections were given to mice (N=11 per group) every 72 h, starting 7 days after tumour inoculation. Mice were injected with 'targeted' polymer formulation (14, 56.4 μg) and plasmid DNA (5 μg). Mice were treated with either pcDNA, dCas9 no effector, dCas9-VPR/SAM (MASPIN) or dCas9-VPR (CCN6) formulations. Mice received a total of 5 injections.

Tumour progression was followed by caliper measurements every 48 h. Mice were sacrificed at day 23, 39 and 46 (N=3 per timepoint) for tissue collection and analysis.

Bioluminescence Imaging

Mice received an intraperitoneal injection of D-luciferin (200 μL, 15 mg/mL in PBS) prior to being anesthetized (4% isoflurane initially, 2% to maintain state during imaging). Mice were imaged for bioluminescence using Caliper IVIS Lumina II imaging system 10-15 min after injection, once bioluminescence signal intensity had reached steady state.

Sectioning and Staining (H&E, Immunofluorescence)

Tissue was collected and preserved in 4% paraformaldehyde (PFA) in PBS. Prior to wax-embedding, tissue was washed and stored in 70% EtOH. 5 μm sections of collected tissue were cut using Leica wax microtome. Sections either underwent standard hematoxylin and eosin (H&E) staining, or were stained for immunofluorescence analysis.

Immunofluorescence staining: Tissue sections were dewaxed and hydrated as per standard protocol. Antigen retrieval was conducted using KOS Microwave Multifunctional Tissue Processer with samples in sodium citrate buffer (10 mM sodium citrate, 0.05% Tween-20, pH 6.0). Staining method was adapted from Abcam published ICC and IF protocol (http://www.abcam.com/tag/ihc%20protocols). Briefly, tissue was permeabilized by incubation in 0.2% Triton X-100 in TBST (TBS, 0.1% Tween 20) for 10 min and then washed three times for 5 min with TBST. Sections were blocked with 1% BSA and 10% normal goat serum in TBST for 90 min at room temperature. Blocking solution was removed and tissue sections were incubated with primary antibody in 1% BSA in TBST at 4° C. overnight in a humidified chamber. Primary antibody solution details can be found in Table 9.

Solution was decanted and sections washed three times in TBST for 5 min per wash, then incubated with secondary antibody (AF647-conjugated donkey anti-rabbit, 1:400, Abcam ab150075; or AF633-conjugated goat anti-rabbit, 1:400, Molecular Probes A-21070; or AF647-conjugated chicken anti-mouse, 1:400, Molecular Probes A-21463) in 1% BSA at r.t. for 1 h. Secondary antibody solution was removed, sections were washed three times in TBST for 5 min each and sections were incubated with Hoechst 34580 (Sigma Aldrich, 1:1000 dilution in TBST), washed three times in TBST for 5 min and mounted using Fluoromount-G aqueous mounting media (Southern Biotech).

TABLE 9

Primary antibody purchase and dilution details.

| Target | Supplier | Catalogue Number | Dilution |
|---|---|---|---|
| Ki67 | Cell Signaling Technology | 9449S | 1:400 |
| HA11 | Santa Cruz | sc-805 | 1:200 |
| Cleaved caspase 3 | Cell Signaling Technology | 9661S | 1:300 |
| MASPIN | BD Bioscience | 554292 | 1:300 |
| CCN6 | Santa Cruz | sc-25443 | 1:300 |
| mCherry | Abcam | ab167453 | 1:500 |

Imaging

Scanscope: H&E stained sections for histology were imaged at 20× magnification using a Leica (Aperio) Scanscope XT Digital Slide Scanner. Images were processed using Aperio ImageScope software.

Confocal: Sections were imaged using a Nikon Ti-E inverted confocal microscope. Images were collected using NIS-C Elements software and processed using ImageJ. Images were taken using a 20× air objective (NA0.75), and sequential excitation using wavelengths of 405 nm (Hoechst 34580), 488 nm (autofluorescence) and 638 nm (AlexaFluor 647 secondary antibody).

Statistical Analysis

Statistical analyses were performed with GraphPad Prism (GraphPad Software Inc.) The data is illustrated as the mean; error bars represent the standard deviation. For all tests, differences were considered significant at $p \leq 0.05$ (*), $p \leq 0.01$ (), $p \leq 0.001$ (*), $p \leq 0.0001$ (****).

Results:

In Vivo Activation of Tumour Suppressor Genes MASPIN and CCN6 Causes Subsequent Loss of Tumorigenic Properties.

Figure 6:
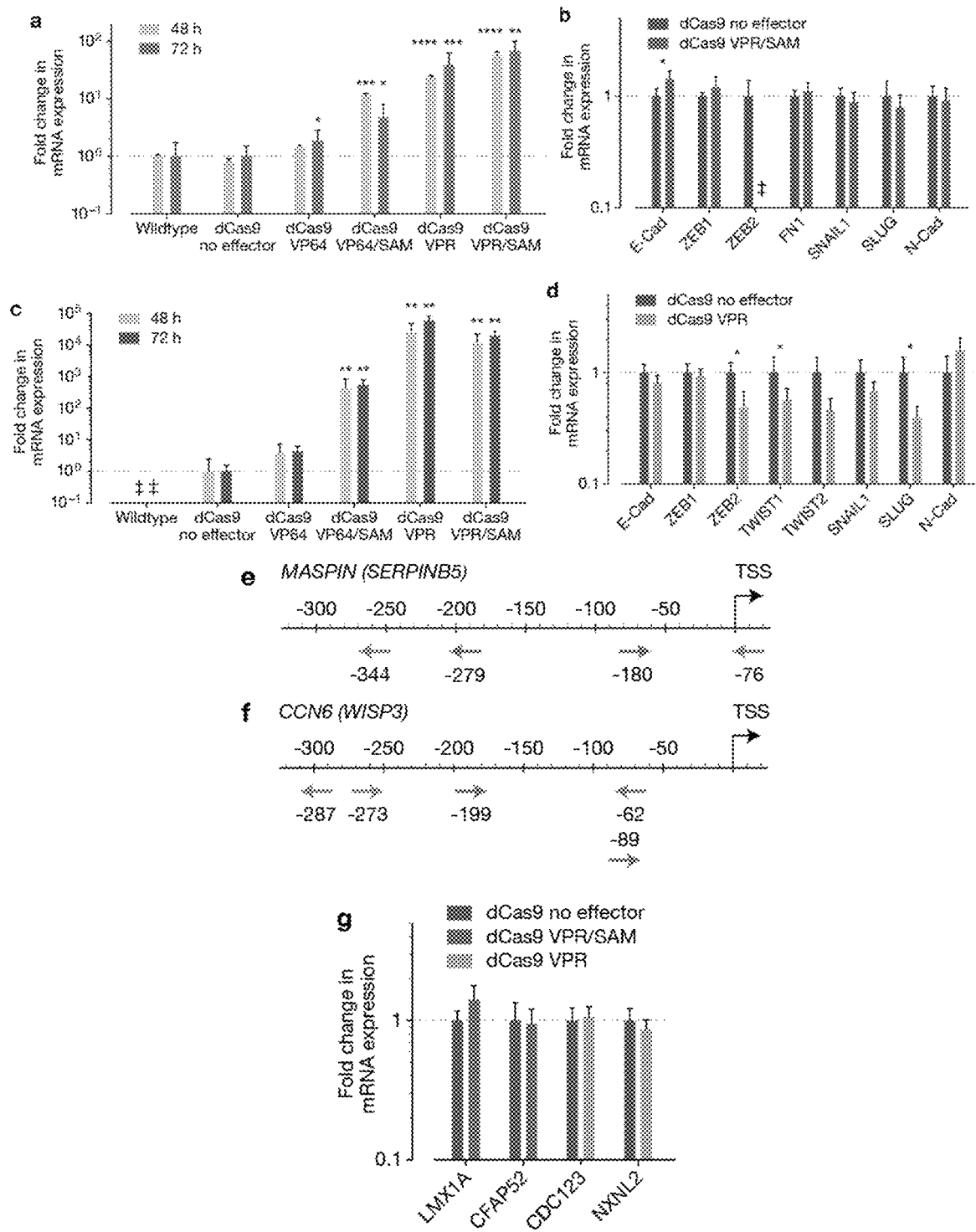
FIG. 6 shows graphs illustrating activation of tumour suppressor genes, MASPIN and CCN6, in vitro in MCF-7 cells. Activation of MASPIN and CCN6 in MCF-7 cells after one transfection demonstrated in (a) and (b) respectively, using various combinations of effectors fused to CRISPR/dCas9. Downstream effects on epithelial and mesenchymal marker genes were checked at 48 h after upregulation of MASPIN and CCN6 in (b) and (d) respectively. Guide design for each of the genes is demonstrated in (e) and (f) for MASPIN and CCN6 respectively. Analysis of potential off-target sites (g) demonstrated no significant alternation in expression. (* p≤0.05, **** p≤0.0001, ns p>0.05).
Figure 7:
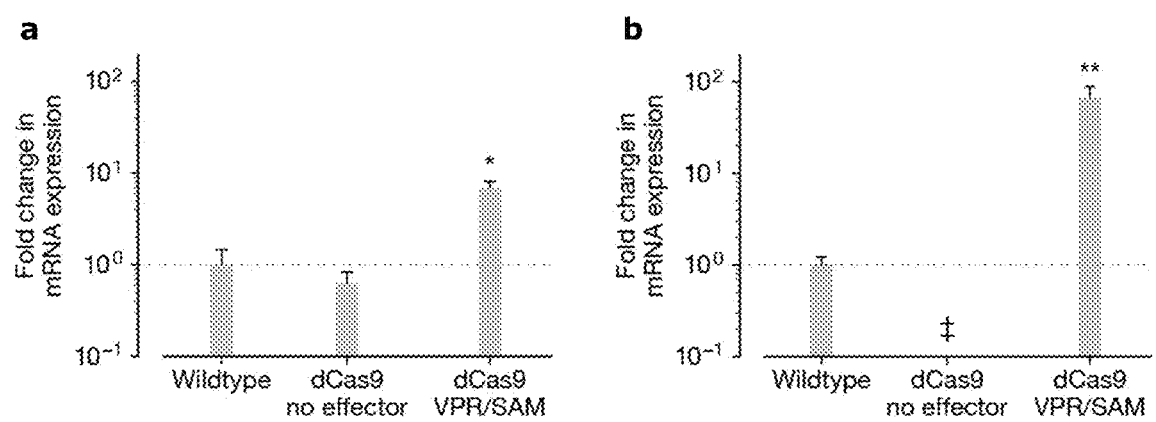
FIG. 7 shows graphs illustrating transfection of H157 cells with CRISPR/dCas9 using VPR/SAM effector for the activation of MASPIN (a) and CCN6 (b). Cells were transfected with CRISPR/dCas9 no effector as a control, and normalized against wildtype. (*p<0.05, **p<0.01.)

To explore whether the dendronised polymeric formulation could efficiently deliver CRISPR/dCas9 technology for the activation of tumour suppressor genes, human breast adenocarcinoma cells (MCF-7) and human non-small lung carcinoma cells (H157) were transfected with a range of effector combinations targeting the activation of either MASPIN or CCN6 (FIGS. 6 and 7). Although the exact role of MASPIN as a tumour suppressor gene is debated, and the dual roles of MASPIN as both tumour suppressor and promoter depending on subcellular location and cancer type have been reported, MASPIN is involved in key processes of cancer progression. Downregulation of MASPIN has been observed in clinical studies of some breast and lung cancers, and associated with tumour progression and poor prognosis. CCN6 is a secreted tumour suppressor commonly downregulated in highly aggressive breast cancers, including triple negative breast cancers (TNBC) and metaplastic carcinomas. To achieve maximum upregulation, CRISPR/dCas9 with guides targeting either MASPIN or CCN6 were fused with either VP64 or VPR activation domains, with and without a SAM complex (FIGS. 6a and 6c for MASPIN and CCN6 respectively). Significant upregulation of MASPIN (~67-fold) and CCN6 (~19,500-fold) were observed in vitro 72 h post-transfection in MCF-7 cells with CRISPR/dCas9-VPR/SAM and CRISPR/dCas9-VPR combinations respectively.

Off-target effects of CRISPR-based technology have been a concern for its clinical application, and include off-target binding, editing and regulation. As a deactivated Cas9 is delivered in this study, the concern is for off-target regulation. CRISPR RGEN Tools (http://www.rgenome.nea/cas-offinder) was used to look at potential binding sites for each guide, and the UCSC Genome Browser (https://genome.ucsc.edu) was then used to determine whether the potential off-target site was located within the promoter region of a gene. Two potential off-target sites with the fewest mismatches and closest proximity to a promoter region were chosen for each of the target genes, and regulation checked by PCR (FIG. 6g). No significant regulation of the potential off-target genes was observed 72 h post-transfection.

Figure 8:
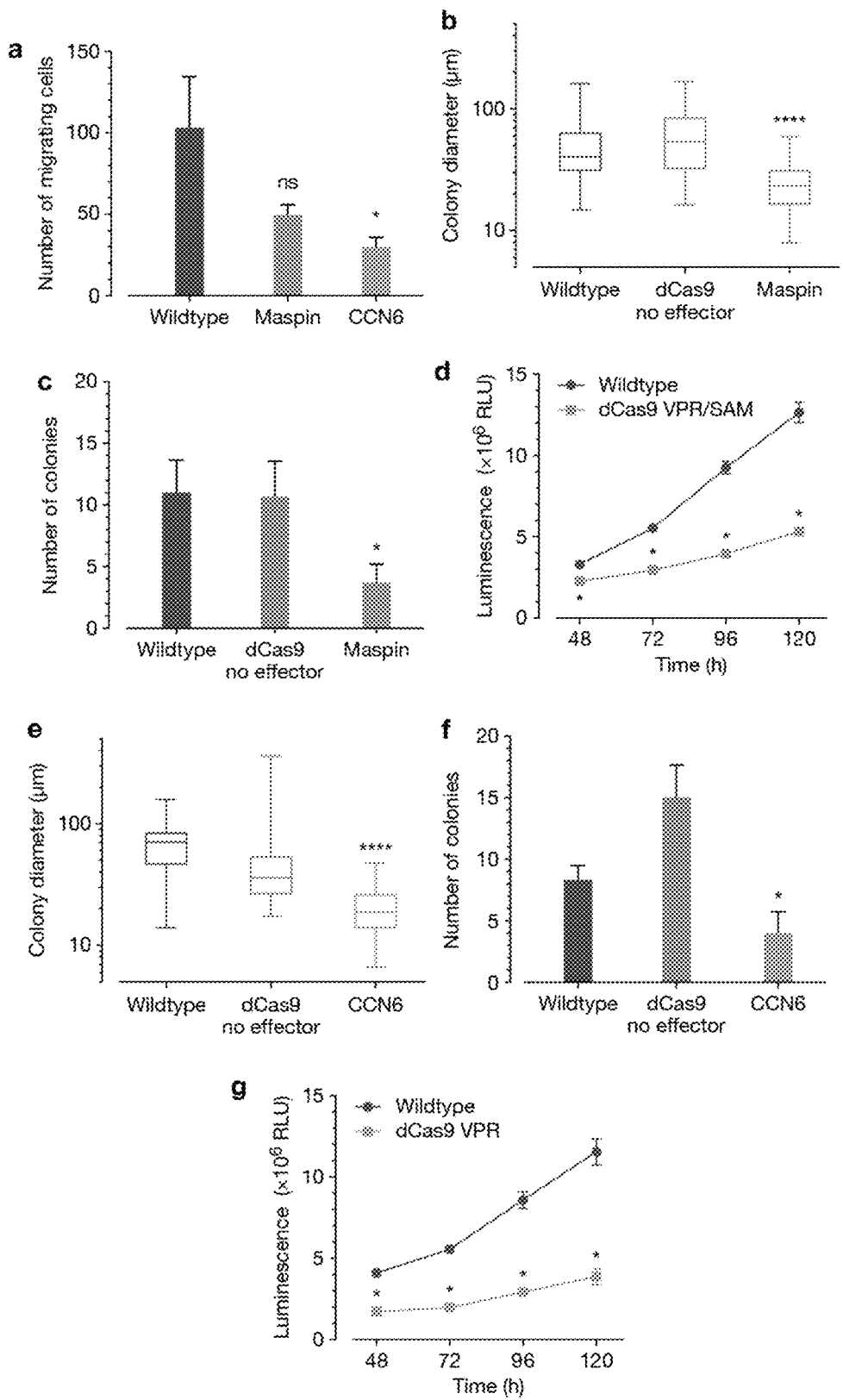
FIG. 8 shows graphs illustrating the loss of tumorigenic properties in MCF-7 cells after activation of MASPIN and CCN6, where the figures shows: (a) Significantly decreased migratory potential of MCF-7 cells 48 h after transfection for MASPIN and CCN6 activation, demonstrated using a transwell migration assay. Wildtype and treated MCF-7 cells were seeded for soft agar assays and the colony diameters and numbers assessed after 3 weeks of growth as shown in (b, c) and (e, f) for MASPIN and CCN6 upregulation, respectively. Activation of both MASPIN and CCN6 resulted in significantly fewer and smaller colonies. Cell proliferation was significantly lower in MCF-7 cells after activation of MASPIN (d) and CCN6 (g) 48-120 hours post-transfection. Statistical analysis was completed against wildtype cells as a control in all cases (* p≤0.05, **** p≤0.0001, ns p>0.05).

Downstream regulation of genes associated with the epithelial-to-mesenchymal transition (EMT) of cancer cells was checked following upregulation of both MASPIN and CCN6 (FIGS. 6b and 6d respectively). Although the MCF-7 model is not highly mesenchymal, activation of MASPIN caused an increase in E-cadherin expression, and activation of CCN6 resulted in significant downregulation of ZEB2, TWIST1 and SLUG 48 h after a single treatment. While downstream target gene regulation can be highly variable and hard to 'pinpoint', cells demonstrated significant decreases in tumorigenic properties such as migration, colony formation and proliferation after activation of both MASPIN and CCN6 as demonstrated in FIG. 8. Since silencing of MASPIN and CCN6 in cancer cell lines has previously been associated with increased cellular invasiveness, we investigated the in vitro migration potential of MCF-7 cells using a Boyden chamber with serum as the chemoattractant. Our results show a significant decrease in the number of migrating cells when CCN6 is highly expressed as shown in FIG. 8a.

Cells transfected for the activation of MASPIN and CCN6 were tested in a soft agar assay, which measures anchorage-independent growth, and is a standard assay for detecting malignant transformation of cells in in vitro conditions. Colonies were analyzed morphologically (for colony diameter) and quantified after 3 weeks of growth. Cells with higher levels of MASPIN and CCN6 demonstrated significantly smaller colonies (FIGS. 8b and 8e) and fewer colonies (FIGS. 8c and 8f) than wildtype MCF-7 cells. Additionally, cell viability and proliferation was monitored 48-120 h post transfection. At 48 h cells there were significantly fewer cells in conditions expressing high levels of both MASPIN and CCN6, and the ensuing proliferation rate remained suppressed (FIGS. 8d and 8g for MASPIN and CCN6 respectively).

Functionalised Dendronised Polymer

Following the promising in vitro characterisation, functionalised dendronised polymer formulations obtained through modification by the attachment of polyethylene glycol (PEG) and either Cyanine-7 (Cy7) fluorescent dye (non-targeted), or cyclic RGD peptide with Cy7 attached (cRDG-Cy7, targeted) were then investigated.

PEG decoration confers 'stealth' properties to the polyplex. By shielding the majority of the positive charge it allows for longer circulation time, minimizing non-specific uptake. formulation through binding with $\alpha_v\beta$-family integrins that are overexpressed on the surface of many cancer cells, including MCF-7. While RGD is typically used to target overexpression of $\alpha_v\beta_3$ integrins, MCF-7 cells express $\alpha_v\beta_5$ and $\alpha_v\beta_6$ integrins which are further overexpressed in the stimulated tumour microenvironment.

Polyplex size and charge before and after PEG-cRGD-Cy7 attachment was assessed using dynamic light scattering and zeta potential measurements in phosphate buffered saline solution (PBS). The measurements show that effective binding of pDNA was maintained, with an accompanying increase in polyplex size and decrease in charge with attachment of PEG-cRGD-Cy7, as expected with the inclusion of PEG.

In Vivo Experiments

Figure 9:
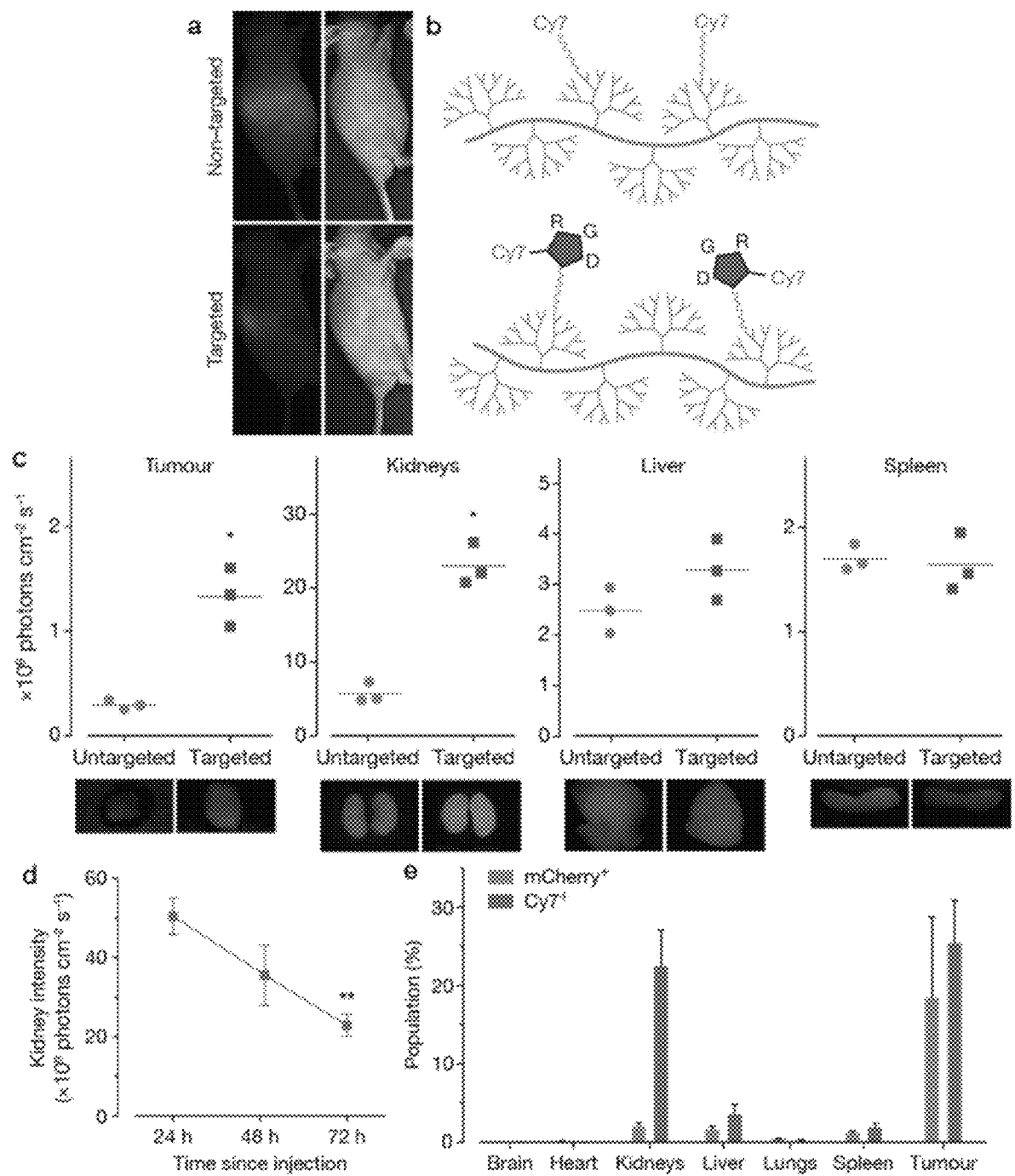
FIG. 9 illustrates: (a) whole animal imaging showing distribution of targeted and non-targeted Cy7 labelled polyplexes 24 h after single i.v. injection, (b) dendronised polymer surface decorated with PMG12 chains and either Cy7 (non-targeted formulation) or cRGD-Cy7 (targeted formulation). (c) cRGD-Cy7 targeted dendronised polymer formulation demonstrated increased tumour uptake 72 h after i.v. injection (N=3), measured by normalized photon flux of tumours ex vivo, with the cRGD-Cy7 targeted polymer demonstrating significant kidney clearance from 48 h to 72 h as measured by ex vivo measurements (total N=7), (e) flow cytometry of harvested tissue demonstrating Cy7+ and mCherry$^+$ cell populations 72 h after single i.v. injection delivered using cRGD-targeted formulation, where mCherry expression was localized to the tumour, with low expression in off-target tissue. (* p<0.05, ** p<0.01).

To confirm targeting, in vivo BALB/c nude mice with MCF-7 luciferase xenograft in the right flank received a single intravenous injection of either the non-targeted or targeted formulation bound with mCherry-encoding plasmid. Distribution of each formulation was monitored over 72 h using whole body live animal imaging, which indicated faster clearance of the targeted formulation through the kidney, and higher accumulation in tumour (FIG. 9a). These mice were sacrificed at 72 h, with additional animals sacrificed at 24 and 48 h time points, and both Cy7 and mCherry fluorescence quantified using ex vivo imaging (FIG. 9d), confocal microscopy (FIG. 9f) and flow cytometry (FIG. 9f). Overall the targeted formulation 16 demonstrated significant kidney clearance over 72 h and low plasmid expression in off-target tissue, as shown through the confocal imaging (FIG. 9f) and flow cytometry experiments (FIG. 9g).

In Vivo Activation of Tumour Suppressor Genes Suppresses Tumour Growth in MCF-7 Xenograft BALB/c Mice.

Figure 10:
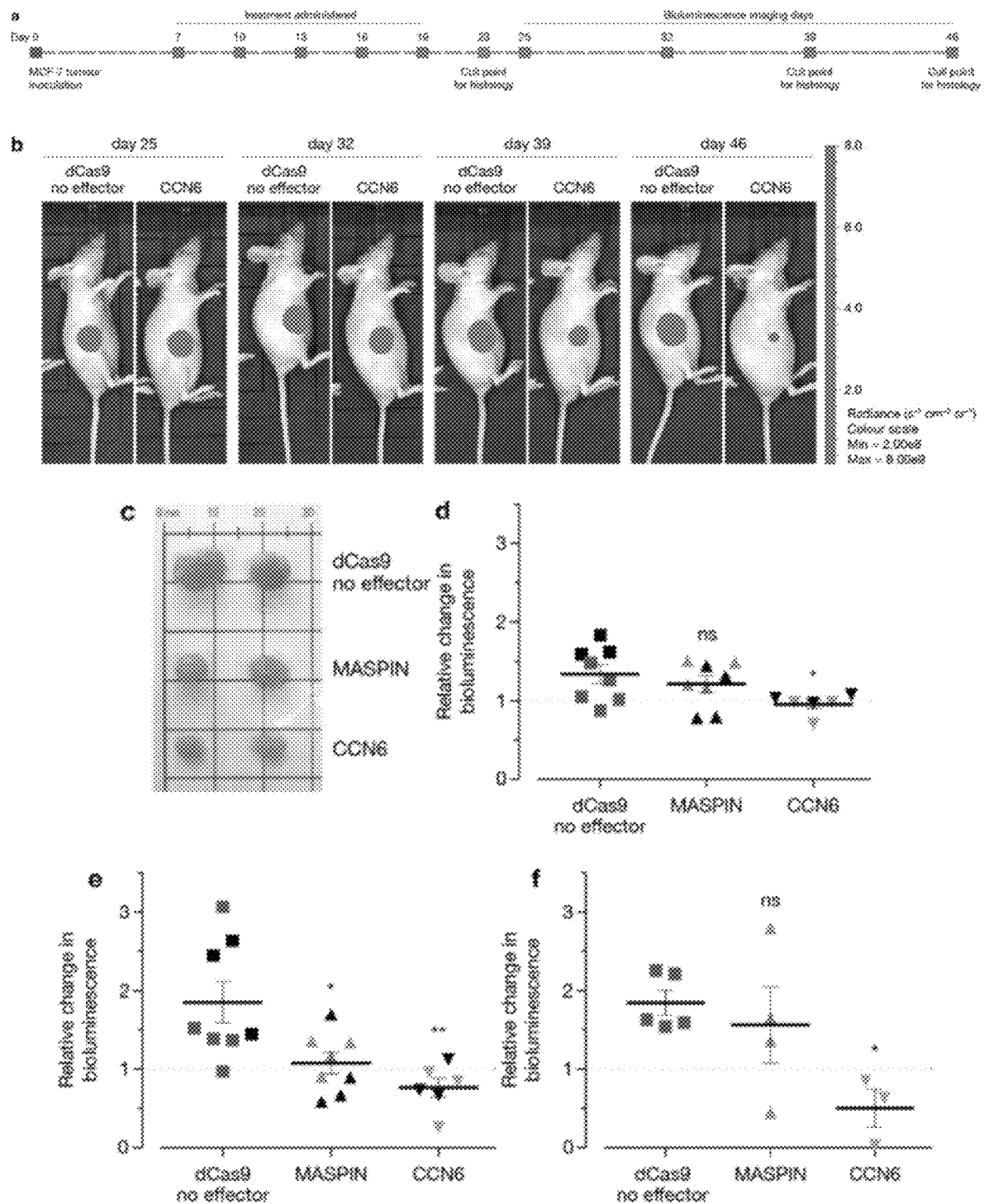
FIG. 10 illustrates results of activation of tumour suppressor genes in vivo by targeted polymeric delivery of CRISPR/dCas9 components, where the figure shows: (a) MCF-7-luciferase tumours were inoculated at day 0 by subcutaneous injection into the right flank of BALB/c nude mice (N=11 per group). Mice received one i.v. injection every 72 h, for a total of 5 injections between day 7 and day 19. Mice were culled at day 23 for histological assessment (N=3 per group), and remaining mice were imaged on days 25, 32 and 39 for tumour burden assessment (N=8), more mice were sacrificed for histological assessment on day 39 after imaging (N=3). Final imaging for tumour burden was conducted on day 46, and all remaining mice were sacrificed for histological assessment, (b) bioluminescence images of mice treated with either dCas9 no effector (control) or dCas9-VPR for the activation of CCN6 from days 25 to 46, (c) representative ex vivo MCF-7-luci tumours excised at day 46 of experiment; and (d, e and f) tumour growth shown as a fold change in size comparing days 25 vs 32, 25 vs 39 and 25 vs 46 respectively. At day 39 MASPIN- and CCN6-treated tumours demonstrated significant tumour suppression compared to dCas9 no effector control. At day 46 significant tumour repression was observed in CCN6 tumours. Each point represents an individual animal, while coloured points represent animals which remained for the entire experiment. (* $p \leq 0.05$, ** $p \leq 0.01$, ns $p > 0.05$).
Figure 12:
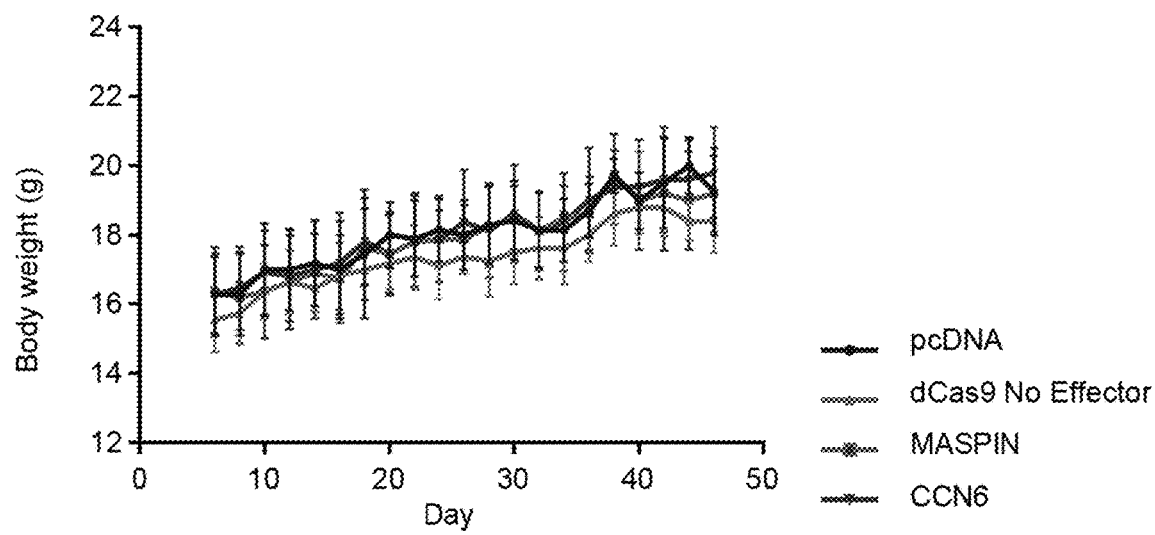
FIG. 12 illustrates graphs showing the results of body weight and tumour volume measurements of BALB/c nude mice with MCF-7 luciferase xenograft tumour monitored throughout a 46 day experiment. (a) Mice were 5-8 weeks old at baseline, body weight measurements were taken every 48 h during the course of the experiment. (b) Tumour length and width were measured every 48 h with a vernier caliper. Tumour volume was calculated as volume=0.5 (length× width$^2$). Animals receiving treatments for the activation of MASPIN and CCN6 demonstrated significantly smaller tumours compared to dCas9 no effector control. Animals receiving treatment for CCN6 activation demonstrated significant tumour regression from day 30 (****$p<0.0001$). Data was analysed using two-way ANOVA, comparing across each treatment group over time. Significance is given for the comparison of the final time point.
Figure 12:
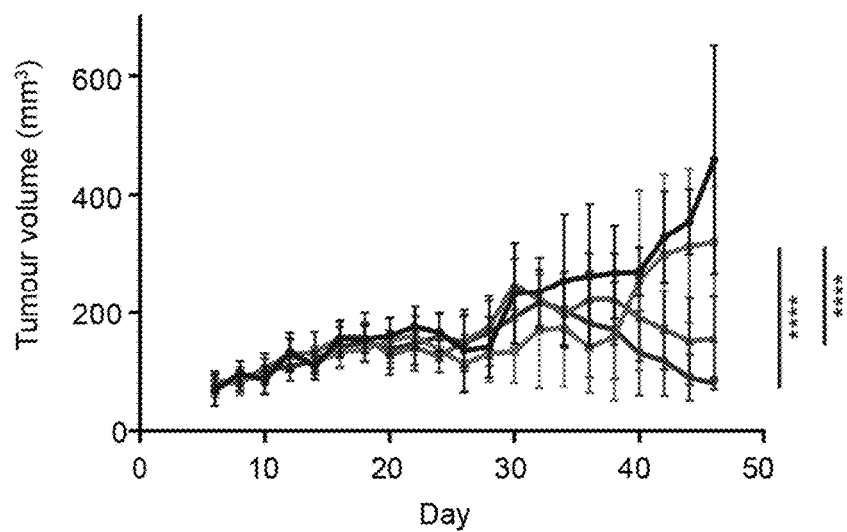

Following confirmation of tumour targeting and uptake in the BALB/c MCF-7 luciferase xenograft model with the targeted polymer formulation 15 (without Cy7 fluorescent tag), we attempted delivery of CRISPR-based technology to yield a functional outcome. The experimental timeline is depicted in FIG. 10a. Mice received a total of five intravenous injections (one injection every 72 h), from days 7 to 19, with each dosage approximately 0.3 mg/kg of plasmid. Mice received polymer delivering either non-coding pcDNA, CRISPR/dCas9 no effector, CRISPR/dCas9-VPR/SAM targeting MASPIN activation or CRISPR/dCas9-VPR targeting CCN6 activation. Mice were sacrificed 72 h after last injection (day 23) to assess tissue for histology and toxicity. Preliminary assessments showed that kidneys looked normal. Mouse body weight and tumour volume were measured every 2 days, where no significant difference in animal body weight was observed (FIG. 12a), and tumour volume for MASPIN and CCN6 treatment mice demonstrated significantly smaller tumours than the no effector control (FIG. 12b). Animals were imaged in days 25, 32, 39 and 46 and tumour size assessed by bioluminescent intensity (FIG. 10b). Tumour progression was monitored and normalised to bioluminescent reading taken on day 25 (FIG. 10d-f). At day 32, mice treated with activation of CCN6 were showing significant tumour suppression (FIG. 10d), and by day 39 and 46 (FIGS. 10e and 10f respectively), some individual mice were demonstrating tumour regression as well as significant suppression across the group. Mice treated with MASPIN activation demonstrated a more delayed tumour suppression effect at day 39 (FIG. 10e), and by day 46, while two mice with activated MASPIN demonstrated continued tumour suppression (0.44-fold and 1.35-fold changes in size), two tumours demonstrated 1.6-fold and 2.8-fold growth over the course of the week. The difference in tumour response could be due to variations in tumour vascularisation and therefore variations to which regions and how many cells received the treatment. We hypothesize that since CCN6 protein is excreted, even if only select regions of the tumour received the treatment for CCN6 activation, the effect is spread throughout the whole tumour, making it a more successful tumour suppressor target. All remaining mice were sacrificed at day 46 for histological assessment of tumours (photographed FIG. 10c).

Figure 11:
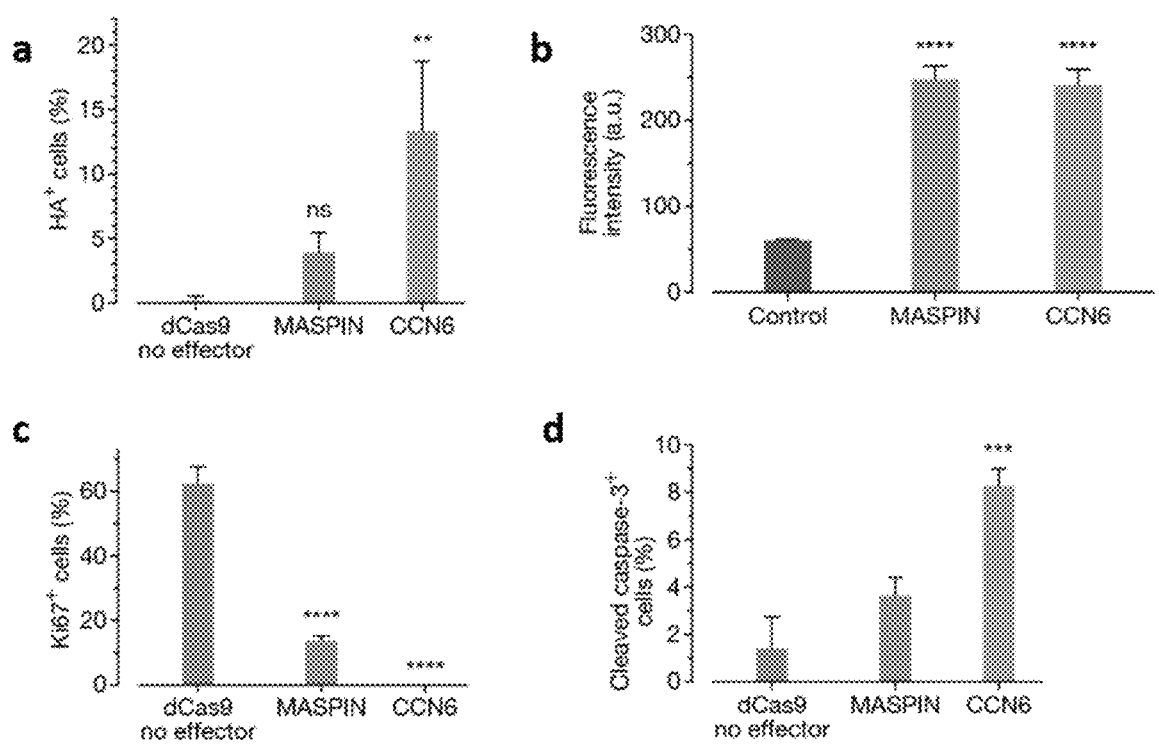
FIG. 11 illustrates graphs showing results from the immunofluorescent assessment of MCF-7-luci tumour sections. Tumour sections taken from day 23 were stained for HA11 epitope, to assess expression of the CRISPR/dCas9 and effectors. (a) Quantification of HA11-positive cells; tumours which received CRISPR/dCas9-VPR targeting CCN6 demonstrated a significant increase in the number of HA11-positive cells compared to no effector control. Tumour sections from day 23 were stained using anti-MASPIN and anti-CCN6 antibodies, and demonstrated significant upregulation of the target gene (b) when compared to tissue which received non-coding pcDNA. Tumour sections taken from day 46 were stained for proliferation marker Ki67 and apoptosis marker cleaved caspase-3. MASPIN and CCN6 upregulation in tumours caused significant decreases in proliferation (c), while upregulation of CCN6 also demonstrated significant levels of apoptosis (d) when compared to the dCas9 no effector control. ( $p \leq 0.01$, * $p \leq 0.001$, **** $p \leq 0.0001$, ns $p > 0.05$).

Animals were sacrificed at days 23, 39, and 46 for immunofluorescent assessment of processes occurring in the tissue at different stages. At day 23 animals treated for the activation of MASPIN and CCN6 demonstrated expression of the CRISPR/dCas9-VPR protein (FIG. 11a). CCN6 demonstrated significantly greater presence of the HA11-tagged protein than the control CRISPR/dCas9 no effector tissue. MASPIN-treated tissue did not show a significantly higher expression, but this may be due to lower levels of the VPR effector being delivered, as it was co-delivered with the SAM complex. Nevertheless, both MASPIN and CCN6 protein expression was observed to be significantly higher in the tumours of the treated animals compared to control tissue (FIG. 11b). At day 46 tumours in the no effector control group were still proliferating at a significantly higher rate than that in treated tissue, as assessed by immunofluorescent staining for Ki67 proliferation marker (FIG. 11c). In addition to the low proliferation level, tumours treated by activation of CCN6 also displayed apoptosis in approximately 8% of cells at day 46, as assessed using cleaved caspase-3 assay (FIG. 11d). Therefore, the activation of CCN6 resulted in long-term tumour suppression and regression, with effects ongoing 4 weeks after treatment had ceased.

The results in this study showed that dendronised polymers functionalised with a targeting ligand enabled the targeted in vivo delivery of CRISPR/dCas9 technology for the activation of tumour suppressor genes efficiently, and with no observable toxicity or off-target effects.

Collectively, these results demonstrate polymeric delivery of CRISPR technology for the activation of tumour suppressor genes is a viable platform for alternative cancer therapeutics.

Example 3

Dendronised Polymer Prepared by Divergent Synthetic Method

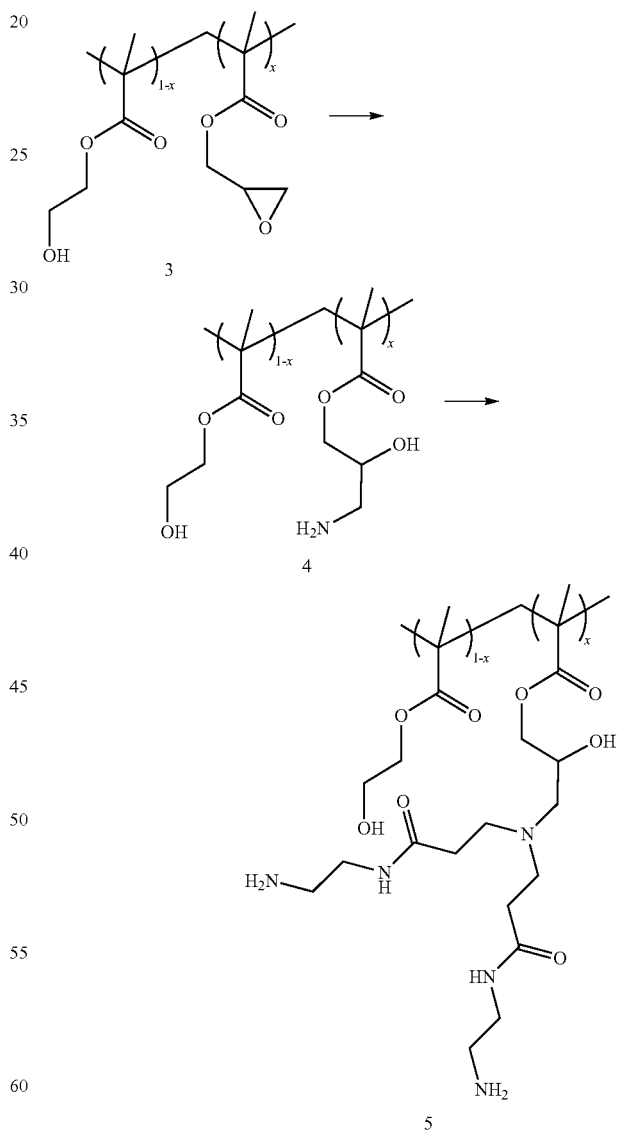

A typical synthesis involved the dissolution of P(HEMA$_a$-ran-GMA$_b$) copolymer (~2 g, 14 mmol, 3) in MeOH (15 mL). Aqueous ammonia (30% NH$_3$ $_{(aq)}$, (4 mL, 0.1 mol) was added to the stirring reaction solution followed by TEA (4 mL, 29 mmol). Reaction was conducted at 50-55° C. for 72 hours. Product (P(HEMA$_a$-ran-GMA$_b$)-AM, 4) was collected under reduced pressure, dissolved in distilled water (20 mL) and purified via 48 hour dialysis. Pure product was collected once lyophilised at ~87% yield. Successful reaction was verified via $^1$H NMR (400 MHz, CD$_3$OD) by the disappearance of peaks $\delta_H$ 2.70, 1H, br, 2.87, 1H, br, which indicate opening of the epoxide moiety.

Typical synthesis of the further generation dendron involves a two-step addition adapted from Lee, J. W. et al. Convergent Synthesis of Symmetrical and Unsymmetrical PAMAM Dendrimers. *Macromolecules* 39, 2418-2422 (2006). Initially, copolymer 4 was dissolved in minimum MeOH (5-10 mL). Methyl acrylate (MA, 2-8 mL, 22-88 mmol) was added to the stirring reaction solution. Reaction flask was then flushed with nitrogen and stoppered. Reaction was conducted over the period of a week at room temperature, the product collected under reduced pressure. Reaction success was verified by $^1$H NMR (400 MHz, CD$_3$OD) where the ester singlet appears at $\delta_H$ 3.74 ppm. The second stage of the synthesis involves the dissolution of the ester product in MeOH (5-10 mL). Ethylene diamine (10 mL, 0.15 mol) was added dropwise to the stirring reaction solution before flask was stoppered and flushed with nitrogen. Reaction was conducted over the period of a week at room temperature. Product 5 was purified via 48 hour dialysis in distilled water and collected after lyophilisation at 70-85% yield. Reaction was confirmed by the disappearance of the aforementioned ester singlet. Repetition of the two-step addition reactions can be completed to afford higher generation dendrons.

Example 4

In Vitro Delivery of Protein Using Dendronised Polymeric Formulation
Materials and Methods
Dendronised Polymer Preparation

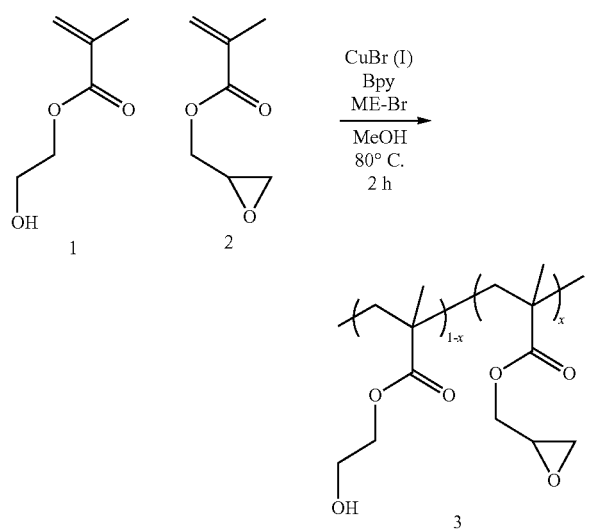

P(HEMA$_{0.75}$-ran-GMA$_{0.25}$) copolymer was synthesized as previously described (adapted from Weaver J. V. M. et al. Stimulus-Responsive Water-Soluble Polymers Based on 2-Hydroxyethyl Methacrylate. *Macromolecues* 37, 2395-2403 (2004)). Briefly, inhibitors for hydroxyethyl methacrylate (HEMA, 1, 30 mmol) and glycidyl methacrylate (GMA, 2, 10 mmol) were removed via passage through a plug of basic alumina and reacted using an atom-transfer radical polymerization method to afford copolymer 3. Copolymer composition was determined by $^1$H NMR (500 MHz, CD$_3$OD), where integration of peaks $\delta$H 2.70 (1H, br) and 2.87 (1H, br) corresponding to the epoxide moiety was used to determine copolymer consists of 25 mol % GMA 2. Polymer molecular weight (21.5 kDa) and PDI (1.30) of the polymer measured using GPC.

Modification of the copolymer and the synthesis of propargyl 5G PAMAM dendrons and attachment of dendrons and fluorination was performed in the same manner as previously described in Examples 1 and 2.

Transfection

HeLa (human cervical adenocarcinoma, ATCC) were cultured in Dulbecco's Modified Essential Medium (DMEM, Gibco), supplemented with 10% PBS and 1× antibiotics/antimycotics, in a humidified incubator at 37° C. with 5% CO$_2$. Cells were seeded in 24-well plates in full media at 1.2×10$^5$ cells/mL.

Figure 13:
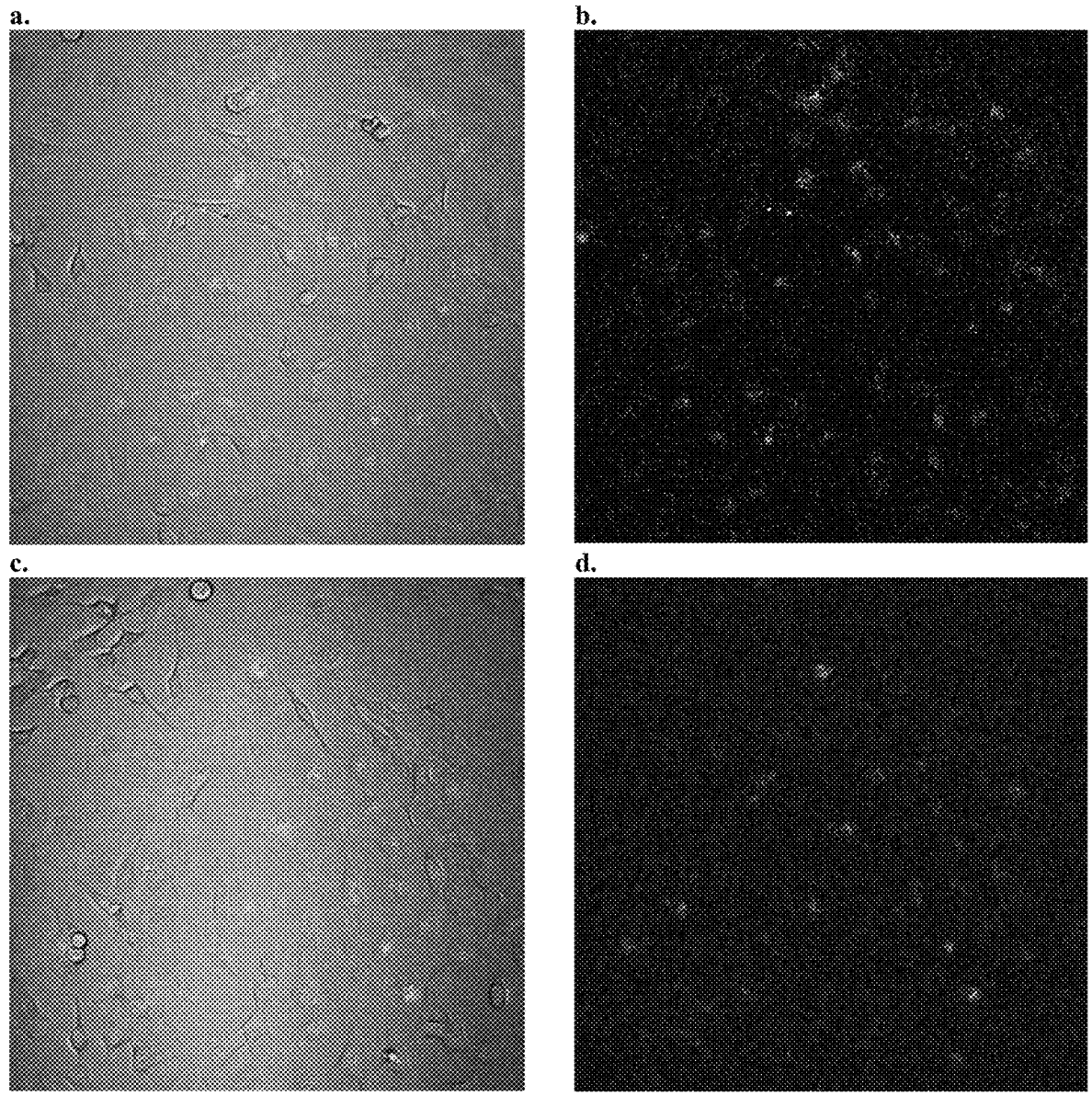
FIG. 13 illustrates transfection of HeLa cells using the fluorescent protein GFP-E20. Shown are (a) a merged GFP and phase image and (b) a GFP image of cells transfected with mass ratio 12:1 dendronised polymer:GFP-E20, with a final concentration of 125 nm GFP-E20; as well as (c) a merged GFP and phase image and (d) a GFP image of cells transfected with mass ratio 12:1 fluorinated dendronised polymer:GFP-E20, with a final concentration of 125 nM GFP-E20 following incubation for 3 hours.

Transfections were performed by first diluting polymer solution and modified GFP-E20 (E-tagged green fluorescent protein, modified as per Mout, R. et al. General strategy for direct cytosolic protein delivery via protein-nanoparticle co-engineering. *ACS Nano* 11, 6416-6421 (2017)) to the required concentration in PBS. For a 24-well standard plate format, polymer solution was prepared as 5 mg/mL in filter sterilised Milli-Q water, and 4.1-16.2 µL of polymer solution was diluted to a total of 50 µL in PBS. 2.5-5 µM GFPE20 was prepared in PBS, and then 50 µL was mixed thoroughly with 50 µL of polymer solution (testing mass ratios of 6:1 and 12:1 polymer:GFP-E20 for two different protein concentrations). The mixture was then incubated at r.t. for 2 h, before 100 µL was transferred to the appropriate well, which had been washed twice with PBS and had 150 µL of serum-free media added. Additional 250 µL of prGFPE20 protein delivery was then assessed using a confocal microscope at 3 hours (FIG. 13), 8 hours and 24 hours (FIG. 14).

Results

Figure 14:
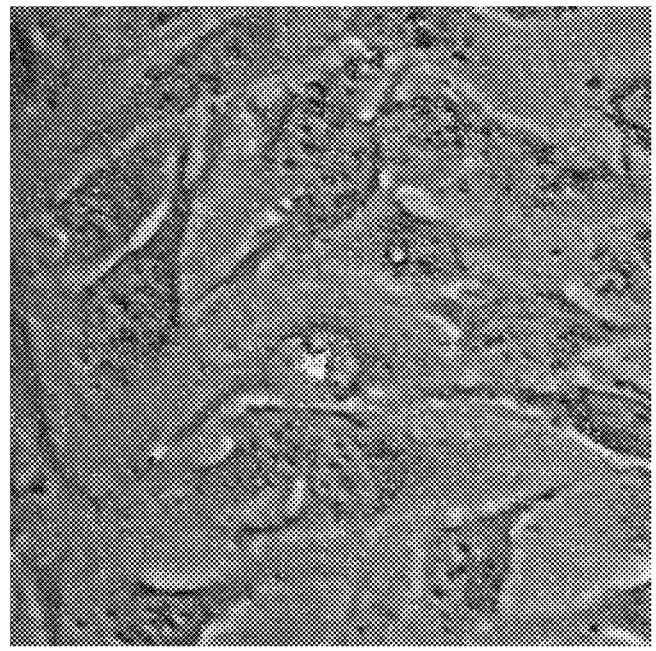
FIG. 14 illustrates transfection of HeLa cells using the fluorescent protein GFP-E20. Cells were transfected with mass ratio 12:1 dendronised polymer:GFP-E20, with a final concentration of 125 nM GFP-E20 following incubation for 24 hours.

The results in this study showed that dendronised polymers (FIG. 13a) and fluorinated dendronised polymers with a targeting ligand (FIG. 13b) enabled the targeted in vitro delivery of a protein molecule efficiently, and with no observable toxicity following incubation for 3 h (FIG. 13) and 24 h (FIG. 14). The results also showed that at least 27% of cells were positive for GFP following delivery by a non-fluorinated or fluorinated dendronised polymer.

Collectively, these results demonstrate the polymeric delivery of protein molecules is a viable platform for the delivery of protein-based therapeutics.

It is to be understood that various other modifications and/or alterations may be made without departing from the spirit of the present invention as outlined herein.

The invention claimed is:

1. A hydrophilic, biocompatible dendronised polymer comprising:
   a linear aliphatic copolymer backbone; and
   a plurality of dendrons pendant from and coupled to the copolymer backbone.

2. A dendronised polymer according to claim 1, wherein each dendron is coupled to the copolymer backbone via a covalent reaction product.

3. A dendronised polymer according to claim 2, wherein each dendron is coupled to the copolymer backbone via a triazole moiety.

4. A dendronised polymer according to claim 1, wherein the copolymer backbone comprises polymerised residues derived from at least two ethylenically unsaturated monomers selected from the group consisting of 2-hydroxyethyl acrylate, 2-methoxyethyl acrylate, N-acryloylamido-ethoxyethanol, N,N-dimethylacrylamide, N,N-diethylacrylamide, N-(2-hydroxyethyl)acrylamide, N-(hydroxymethyl)acrylamide, acrylamide, N-isopropyl acrylamide, methacrylamide, 2-hydroxyethyl methacrylate, 2-(dimethylamino)ethyl acrylate, 3-(dimethylamino)propyl acrylate, acrylic acid, methacrylic acid, 2-(dimethylamino)ethyl methacrylate, glycidyl methacrylate, 2-azido-1-hydroxyethyl methacrylate, and combinations thereof.

5. A dendronised polymer according to claim 1, wherein each dendron is a poly(amido amine) (PAMAM) dendron.

6. A dendronised polymer according to claim 5, wherein each PAMAM dendron is a full generation G4 dendron or a full generation G5 dendron.

7. A dendronised polymer according to claim 1 wherein each dendron comprises at least one terminal functionality selected from the group consisting of fluoro groups, stealth groups, fluorescent groups, and targeting ligands.

8. A dendronised polymer according to claim 7, comprising from 20 to 60 mol % terminal fluoro groups.

9. A method of preparing a hydrophilic, biocompatible dendronised polymer comprising the steps of:
providing a linear aliphatic copolymer backbone comprising a plurality of pendant functional groups capable of participating in a click coupling reaction;
providing a plurality of dendrons, each dendron comprising a functional group at its focal point that is capable of reacting with a pendant functional group via a click coupling reaction; and
reacting the pendant functional groups on the copolymer backbone with the functional groups at the focal point of the dendrons under click chemistry conditions to form a click reaction product that couples each dendron to the copolymer backbone.

10. A method according to claim 9, wherein the click reaction product is a triazole moiety.

11. A method according to claim 9, wherein the linear copolymer backbone is provided by polymerising at least two ethylenically unsaturated co-monomers under a controlled free radical polymerisation process, wherein at least one of the at least two ethylenically unsaturated co-monomers comprises a pendant functional group that, when the co-monomers are polymerized, (i) provides the plurality of pendant functional groups, or
(ii) is modified to provide the plurality of pendant functional groups.

12. A method according to claim 11, wherein the linear polymer backbone is provided by polymerising at least two ethylenically unsaturated monomers selected from the group consisting of 2-hydroxyethyl acrylate, 2-methoxyethyl acrylate, N-acryloylamido-ethoxyethanol, N,N-dimethylacrylamide, N,N-diethylacrylamide, N-(2-hydroxyethyl)acrylamide, N-(hydroxymethyl)acrylamide, acrylamide, N-isopropyl acrylamide, methacrylamide, 2-hydroxyethyl methacrylate, 2-(dimethylamino)ethyl acrylate, 3-(dimethylamino)propyl acrylate, acrylic acid, methacrylic acid, 2-(dimethylamino)ethyl methacrylate, glycidyl methacrylate, 2-azido-1-hydroxyethyl methacrylate, and combinations thereof.

13. A method according to claim 9, wherein each dendron is a poly(amido amine) (PAMAM) dendron.

14. A method according to claim 9, further comprising the step of reacting at least one terminal functional group on each dendron with an agent selected from the group consisting of a fluorination agent, a stealth agent, a fluorescent agent, and a targeting agent to thereby provide a plurality of dendrons with at least one terminal functionality.

15. A complex comprising a biomolecule and dendronised polymer of claim 1.

16. A complex according to claim 15, wherein the biomolecule is selected from the group consisting of a zinc finger nuclease (ZFN), transcription activator-like effector based nuclease (TALEN), CRISPR-mediated gene editing system, a ribonucleoprotein (RNP), and a protein molecule.

17. A method of delivering a biomolecule into a cell comprising exposing the cell to the complex of claim 15.

18. A composition for modulating the expression of at least one gene product in a subject, the composition comprising a complex of a nuclease and a dendronised polymer of claim 1.

19. A method for the treatment of breast adenocarcinoma comprising administering an effective amount of the complex of claim 15 to a subject in need thereof, wherein the biomolecule is CRISPR/dCas9-VPR/SAM or CRISPR/dCas9-VPR.

* * * * *